US010323097B2

(12) United States Patent
Kjaergaard et al.

(10) Patent No.: US 10,323,097 B2
(45) Date of Patent: *Jun. 18, 2019

(54) ANTI-C5A RECEPTOR ANTIBODIES

(71) Applicant: Novo Nordisk A/S, Bagsvaerd (DK)

(72) Inventors: Kristian Kjaergaard, Ballerup (DK); Soeren Lund, Copenhagen SV (DK); Stefan Zahn, Stenloese (DK); Louise H. Zeuthen, Birkeroed (DK); Anker J. Hansen, Charlottenlund (DK)

(73) Assignee: Novo Nordisk A/S, Bagsvaerd (DK)

( * ) Notice: Subject to any disclaimer, the term of this patent is extended or adjusted under 35 U.S.C. 154(b) by 291 days.

This patent is subject to a terminal disclaimer.

(21) Appl. No.: 15/341,550

(22) Filed: Nov. 2, 2016

(65) Prior Publication Data

US 2017/0073421 A1 Mar. 16, 2017

Related U.S. Application Data

(63) Continuation of application No. 14/467,393, filed on Aug. 25, 2014, now abandoned, which is a continuation of application No. 13/920,585, filed on Jun. 18, 2013, now Pat. No. 8,846,045, which is a continuation of application No. 13/490,093, filed as application No. PCT/EP2012/060524 on Jun. 4, 2012, now Pat. No. 8,613,926.

(60) Provisional application No. 61/505,137, filed on Jul. 7, 2011.

(30) Foreign Application Priority Data

Jun. 6, 2011 (EP) .................................... 11168787
Mar. 13, 2012 (EP) .................................... 12159172

(51) Int. Cl.
  *C07K 16/28* (2006.01)
  *A61K 39/395* (2006.01)
  *A61K 39/00* (2006.01)

(52) U.S. Cl.
  CPC .... *C07K 16/2896* (2013.01); *A61K 2039/505* (2013.01); *C07K 2317/21* (2013.01); *C07K 2317/52* (2013.01); *C07K 2317/565* (2013.01); *C07K 2317/71* (2013.01); *C07K 2317/76* (2013.01); *C07K 2317/92* (2013.01)

(58) Field of Classification Search
  None
  See application file for complete search history.

(56) References Cited

U.S. PATENT DOCUMENTS

| | | | |
|---|---|---|---|
| 3,850,752 A | 11/1974 | Schuurs et al. | |
| 3,901,654 A | 8/1975 | Gross | |
| 4,098,876 A | 7/1978 | Piasio et al. | |
| 4,568,649 A | 2/1986 | Bertoglio-Matte | |
| 4,676,980 A | 6/1987 | Segal et al. | |
| 4,704,362 A | 11/1987 | Itakura et al. | |
| 5,194,594 A | 3/1993 | Khawli et al. | |
| 5,284,746 A | 2/1994 | Sledziewski et al. | |
| 5,304,489 A | 4/1994 | Rosen | |
| 5,354,678 A | 10/1994 | Lebowski et al. | |
| 5,480,974 A | 1/1996 | Morgan et al. | |
| 5,741,957 A | 4/1998 | Deboer et al. | |
| 5,849,992 A | 12/1998 | Meade et al. | |
| 5,861,272 A | 1/1999 | Li et al. | |
| 8,007,798 B2 | 8/2011 | Ashkenazi et al. | |
| 8,071,096 B2 | 12/2011 | MacKay et al. | |
| 8,071,839 B2 | 12/2011 | Mackay | |
| 8,221,757 B2 | 7/2012 | MacKay | |
| 8,268,972 B2 | 9/2012 | Whitfeld et al. | |
| 8,337,852 B2 | 12/2012 | Mackay | |
| 8,361,468 B2 | 1/2013 | Whitfeld et al. | |
| 8,445,515 B2 | 5/2013 | Fan et al. | |
| 8,613,926 B2 | 12/2013 | Kjaergaard et al. | |
| 8,846,045 B2 | 9/2014 | Kjaergaard et al. | |
| 2001/0036650 A1 | 11/2001 | Li et al. | |
| 2002/0161201 A1 | 10/2002 | Filpula et al. | |
| 2003/0113798 A1 | 6/2003 | Burmer et al. | |
| 2004/0110226 A1 | 6/2004 | Lazar et al. | |
| 2005/0084906 A1 | 4/2005 | Goetsch et al. | |
| 2005/0238646 A1 | 10/2005 | Ledbetter et al. | |
| 2006/0240436 A1 | 10/2006 | Golz et al. | |
| 2006/0275834 A1 | 12/2006 | Ritchlin et al. | |
| 2008/0233137 A1 | 9/2008 | Van Strijp et al. | |
| 2009/0053240 A1 | 2/2009 | Lazar et al. | |
| 2009/0252743 A1 | 10/2009 | Heavner et al. | |
| 2009/0312526 A1 | 12/2009 | Mackay | |

(Continued)

FOREIGN PATENT DOCUMENTS

| | | |
|---|---|---|
| CN | 1553813 A | 12/2004 |
| EA | 201101009 A1 | 1/2012 |

(Continued)

OTHER PUBLICATIONS

Altschul et al., Journal of Molecular Biology., "BLASTP, BLASTN, and FASTA", 1990, vol. 215, No. -, pp. 403-410.

(Continued)

*Primary Examiner* — Phillip Gambel

(74) *Attorney, Agent, or Firm* — Knobbe, Martens, Olson & Bear LLP

(57) ABSTRACT

The present invention concerns human antibodies recognizing the human C5a receptor. By binding to C5aR the antibodies inhibit C5a signalling, whereby the pro-inflammatory signal is inhibited. Based on the role of C5a and its receptor in stimulation of inflammation the invention further relates to therapeutic use of said human anti-C5aR antibodies and in particular in relation to treatment of immunological disorders.

19 Claims, 6 Drawing Sheets

Specification includes a Sequence Listing.

(56) References Cited

U.S. PATENT DOCUMENTS

| | | | |
|---|---|---|---|
| 2009/0324585 | A1 | 12/2009 | Robinson et al. |
| 2010/0129346 | A1 | 5/2010 | Mackay |
| 2011/0082126 | A1 | 4/2011 | Bansal |
| 2011/0190477 | A1 | 8/2011 | Whitfeld et al. |
| 2013/0004514 | A1 | 1/2013 | Zahn et al. |
| 2013/0129717 | A1 | 5/2013 | Mac |
| 2013/0129721 | A1 | 5/2013 | Whitfeld et al. |
| 2013/0142804 | A1 | 6/2013 | Hilden et al. |
| 2013/0183280 | A1 | 7/2013 | Oestergaard et al. |
| 2015/0044231 | A1 | 2/2015 | Kjaergaard et al. |
| 2016/0060351 | A1 | 3/2016 | Andersson et al. |

FOREIGN PATENT DOCUMENTS

| | | | |
|---|---|---|---|
| EP | | 0377489 | 7/1990 |
| EP | | 0586505 | 3/1994 |
| EP | | 1476469 A1 | 11/2004 |
| JP | | 8109200 | 4/1996 |
| WO | | 1991000360 | 1/1991 |
| WO | | 1992020373 | 11/1992 |
| WO | | 19940007921 | 4/1994 |
| WO | | 1994011026 | 5/1994 |
| WO | | 1994020142 | 9/1994 |
| WO | | 1995000164 | 1/1995 |
| WO | | 1996039511 | 12/1996 |
| WO | | 1998024893 A2 | 6/1998 |
| WO | | 1998033908 | 8/1998 |
| WO | | 1998044001 | 10/1998 |
| WO | | 2002038767 | 5/2002 |
| WO | | 2002059263 A2 | 8/2002 |
| WO | | 2002061087 A2 | 8/2002 |
| WO | | 2003027252 A2 | 4/2003 |
| WO | | 2003062278 | 7/2003 |
| WO | WO 2004/035079 | | 4/2004 |
| WO | | 2004040000 A2 | 5/2004 |
| WO | | 2004/050683 A2 | 6/2004 |
| WO | | 2005/040219 A1 | 5/2005 |
| WO | | 2005060739 | 7/2005 |
| WO | | 2006/099875 A1 | 9/2006 |
| WO | WO 2007/055374 | | 5/2007 |
| WO | | 2008022390 | 2/2008 |
| WO | | 2008022391 | 2/2008 |
| WO | | 2008/030564 A2 | 3/2008 |
| WO | | 2009/053368 A1 | 4/2009 |
| WO | | 2009/103113 A1 | 8/2009 |
| WO | | 2010/000864 A1 | 1/2010 |
| WO | WO 2011/100477 | | 8/2011 |
| WO | | 2011/104381 A2 | 9/2011 |
| WO | | 2011/147921 A1 | 12/2011 |
| WO | | 2012/088247 A2 | 6/2012 |
| WO | WO 2012/168199 | | 12/2012 |

OTHER PUBLICATIONS

Bird et al, Science, "Single Chain Antigen-Binding Proteins", 1988, vol. 242, No. -, pp. 425-426.

Caceci et al, Byte, "Fitting Curves to Data", 1984, vol. 9, No. -, pp. 340-362.

Carillo et al., -, "Sequence Analysis Primer", 1988, vol. 48, No. -, pp. 1073.

Chu et al, Molecular Inmunology, "Inhibition of B Cell Receptor-Mediated Activation of Primary Human B Cells by Coengagement of CD19 and FC RIIB With FC-Engineered Antibodies", 2008, vol. 45, No. 15, pp. 3926-3933.

D.M.Glover and B.D.Hames, -, "DNA Cloning: A Practical Approach, IRL Press", 1996, vol. , No. -, pp. -.

Dayhoff et al., Atlas of Protein Sequence and Structure, "A Model of Evolutionary Change in Proteins", 1978, vol. 5, No. 3, pp. 345-352.

Devereux et al., Nucleic Acids Research, "Gap", 1984, vol. 12, No. -, pp. 387.

Ed Harlow and David Lane, "Antibodies: A Laboratory Manual, Cold Spring Harbour Laboratory", 1988, p. 76.

Elvin Abraham Kabat et al., -, "Sequences of Proteins of Immunological Interest Fifth Edition, U.S. Department of Health and Human Services, NIH Publication No. 91-3242", 1991, vol. -, No. -, pp. -.

F.M., Ausubel et al, -, "Current Protocols in Molecular Biology, Green Publishers and Associates and Wiley Interscience", 1988, vol. -, No. -, pp. -.

M. Gribskov, J. Devereux, Sequence Analysis Primer, Stockton Press, NewYork and Macmillan, Basingstroke (1991), pp. 90-157.

Griffin, A. M., and Griffin, H. G., Humana Press, "Computer Analysis of Sequence Data", 1994, vol. 1, pp. 1-8.

Henikoff et al, Proceedings of the National Academy of Sciences of the USA, "Amino Acid Substitution Matrices From Protein Blocks", 1992, vol. 89, No. -, pp. 10915-10919.

Holliger et al, Nature Biotechnology (Continuation of Bio/Technology), "Engineered Antibody Fragments and the Rise of Single Domains", 2005, vol. 23, No. 9, pp. 1126-1136.

Huang Lili et al, Journal of Molecular Recognition, "Discovery of Human Antibodies Against the C5AR Target Using Phage Display Technology", 2005, vol. 18, No. 4, pp. 327-333.

Huston et al, Proceedings of the National Academy of Sciences of the USA, "Protein Engineering of Antibody Binding Sites: Recovery of Specific Activity in an Anti-Digoxin Single-Chain Fv Analogue Produced in *Escherichia coli*", 1988, vol. 85, No. , pp. 5879-5883.

Ill et al, Protein Engineering, "Design and Construction of a Hybrid Immunoglobulin Domain With",1997 , vol. 10 , No. 8 , pp. 949.

J.E.Coligan et al, -, "Current Protocols in Immunology, John Wiley and Sons", -, vol. -, No. -, pp -.

J.Perbal, -, "A Practical Guide to Molecular Cloning, John Wiley & Sons", 1984, vol. -, No. -, pp. -.

J.Sambrook et al, "Molecular Cloning: A Laboratory Manual, Cold Spring Harbour Laboratory Press", 1989, pp. 16.1-17.1.

Lesk, A. M. "Computational Molecular Biology", 1988, pp. 249-254.

Mckay Brown et al, Journal of Immunology, "Tolerance to Single, But Not Multiple, Amino Acid Replacements in Antibody V, CDR2", 1996, vol. 156, No. 9, pp. 3285-3291.

Smith, D. W., Academic Press, "Biocomputing: Informatics and Genome Projects", 1993, vol. -, No. -, pp. -.

T.A.Brown, -, "Essential Molecular Biology: A Practical Approach, IRL Press", 1991, vol. 1&2, No. -, pp. -.

Von Heinje, G., Academic Press, "Sequence Analysis in Molecular Biology", 1987, p. 188.

William R Strohl, Current Opinion in Biotechnology, "Optimization of Fc-Mediated Effector Functions of Monoclonal Antibodies", 2009, vol. 20, No. 6, pp. 685-691.

Wong et al, Proceedings of the National Academy of Sciences of the USA, "A Double-Filter Method for Nitrocellulose-Filter Binding: Applicatioto Protein-Nucleic Acid Interactions", 1993, vol. 90, No. -, pp. 5428-5432.

Barry, et al. 1994, "Sequencing and Modeling of Anti-DNA Immunoglobulin Fv Domains Comparison with Crystal Structures", Journal Biol. Chem. 269(5):3623-3632.

Berman, et al. 1988, "Lymphocyte Motility and Lymphocyte Chemoattractant Factors", Immunol. Invest. 17 (8-9):625-677.

Cain, et al. 2001, "Mapping the Ligand-Binding Site on the C5a Receptor: Arginine 74 of C5a Contacts Aspartate282 of the C5a Receptor", Biochemistry. 40(46):14047-14052.

Cain, et al. 2001, "Modilation of Ligand Selectivity by Mutation of the First Extracellular Loop of the Human C5a Receptor", Biochem. Pharmacol. 61(12):1571-1579.

Caldas, et al. 2000, "Design and Synthesis of Germline-Based Hemi-Humanized Single-Chain Fv Against the CD18 Surface Antigen", Protein Eng. 13(5):353-360.

Caldas, et al. 2003, "Humanization of the Anti-CD18 Antibody 6.7: An Unexpected Effect of a Framework Residue in Binding to Antigen", Mol. Immunol. 39(15):941-952.

Caron, et al. 1992, "Engineered Humanized Dimeric Forms of IgG Are More Effective Antibodies", Journal Exp. Med. 176(4):1191-1195.

(56) References Cited

OTHER PUBLICATIONS

Casset, et al. 2003, "A Peptide Mimetic of an Anti-CD4 Monoclonal Antibody by Rational Design", Biochem. Biophys. Res. Commun. 307(1):198-205.
Charlton, et al. 1999, "The Experssion of C5A Receptor (C5AR) (CD88) Is Associated with the Progression of Inflammation in Human Disease", Journal Pathol. 187(Suppl):36A.
Chen, et al. 1995, "Enhancement and Destruction of Antibody Funcation by Somatic Mutation: Unequal Occurence Is Controlled by V Gene Combinatorial Associations" Embo Journal, 14(12):2784-2794.
Chothia & Lesk, 1987, "Canonical Structures for the Hypervariable Regions of Immunglobulins", Journal Mol. Biol. 196(4):901-917.
Chothia, et al. 1989, "Conformations of Immunoglobulin Hypervariable regions", Nature, 342(6252): 877-883.
Co, et al. 1992 "Chimeric and Humanized Antibodies with Specificity for the CD33 Antigen", Journal Immunol. 148(4):1149-1154.
Colman, 1994, "Effects of Amino Acid Sequence Changes on Antibody-Antigen Interactions" Res. Immunol. 145(1):33-36.
Crass, et al. 1999, "Chimeric Receptors of the Human C3a Receptor and C5a Receptor (CD88)" Journal Biol. Chem. 274(13):8367-8370.
Crass, et al. 1999, "Receptor Activation by Human C5a des Arg74 but Not Intact C5a Is Dependent on an Interaction between Glu199 of the Receptor and Lys68 of the Ligand", Biochemistry, 38(30):9712-9717.
Curiel, et al. 1992, "High-Efficiency Gene Transfer Mediated by Adenvirus Coupled to DNA-Polylysine Complexes", Hum. Gene Ther. 3(2):147-154.
Dahinden, et al. 1994 "Monocyte Chemotactic Protein 3 Is a Most Effective Basophil- and Eosinophil-Activating Chemokine", Journal Exp. Med. 179(2):751-756.
Dai, et al. 1992, "Gene Therapy via Primary Myoblasts: Long-Term Expression of Factor IX Protein Following Transplantation in Vivo", Proc. Natl. Acad. Sci. USA, 89(22):10892-10895.
Demartino, et al. 1995, "Arginine 206 of the C5a Receptor in Critical for Ligand Recognition and Receptor Activation by C-Terminal Hexapeptide Analogs", Journal Biol. Chem. 270(27):15966-15969.
Eigenbrot, et al. 1993, "X-ray Structures of the Antigen-Binding Domains from Three Variants of Humanized Anti-p 185HER2 Antibody 4D5 and Comparison with molecular Modeling" Journal Mol. Biol. 229(4):969-995.
Elsner, et al. 1994, "C3a Activates the Respiratory Burst in Human Polymorphonuclear Neutrophilic Leukocytes viz Pertussis Toxin-Sensitive G-Proteins" Blood, 83(11):3324-3331.
Ulmer, et al. 1993, "Heterologous Protection against Influenze by Injection of DNA Encoding a Viral Protein", Science, 259(5102):1745-1749.
Van Damme,et al. 1992, "Structural and Funcational Identification of Two Human, Tumore Derived Monocyte Chemotactic Proteins (MCP-2 and MCP-3) Belonging to the Chemokine Family", Journal Exp. Med. 176(1):59-65.
Van Meerten, et al. 2006, "Complement-Induced Cell Death by Rituzimab Depends on CD20 Expression Level and Acts Complementary to Antibody-Dependent Cellular Cytoxicity", Clin. Cancer Res. 12(13):4027-4035.
Van Riper, et al. 1993, "Characterization and Species Distribution of High Affinity GTP-Coupled Receptors for Human Rantes and Monocyte Chemoattractant Protein 1", Journal Exp. Med. 177(3):851-856.
Verhoeyen, et al. 1988, "Reshaping Human Antobodies: Grafting an Antilysozyme Activity", Science, 239(4847):1534-1536.
Vitetta, 1993, "Immunotoxins: Magic Bullets or Misguided Missiles?", Immunol. Today, 14(6):252-259.
Vitetta, et al. 1987, "Redesigning Nature's Poisons to Create Anti-Tumor Reagents", Science, 238(4830):1098-1104.
Watanabe, et al. 1995, "Analysis of C5a Receptor by Monoclonal Antibody", Journal Immunol. Methods, 185(1):19-29.
Whitfeld, et al. 2007, "Novel mAbs to C5aR 2nd Loop Reverse Disease in Models of Inflammatory Arthritis", Inflamm. Res. 56(Suppl. 3):S401.
Williams, et al. 1991, "Introduction of Foreign Genes into Tissues of Living Mice by DNA Coated Microprojectiles", Proc. Natl. Acad. Sci. USA, 88(7):2726-2730.
Wipke & Allen, 2001, "Essential Role of Neutrophils in the Initiation and Progression of a Murine Model of Rheumatoid Arthritis", Jounral Immunol. 167(3):1601-1608.
Wolff, et al. 1993, "Monoclonal Antibody Homodimers: Enhanced Antitumor Activity in Nude Mice", Cancer Res. 53(11):2560-2565.
Wu & Wu, 1987, "Receptor-Mediated In Vitro Gene Transformation by a Soluble DNA Carrier System", Journal Biol. Chem. 262(10):4429-4432.
Wu, 2003, "Simultaneous Humanization and Affinity Optimization of Monoclonal Antibodies", Mthods Mol. Biol. 207:197-212.
Wu, et al. 1999, "Humanization of a Murine Monoclonal Antibody by Simultaneous Optimization of Framework and CDR Residues", Journal Mol. Biol. 294(1):151-162.
Zachariae, et al. 1990, "Properties of Monocyte Chemotactic and Activating Factor (MCAF) purified from a Human Fibrosarcoma Cell Line", Journal Exp. Med. 171(6):2177-2182.
International Search Report and Written Opinion of the International Searching Authority, PCT/AU 2007/001207, dated Nov. 20, 2007.
Examiner's Report Issued by Australian Patent Office dated Dec. 22, 2011, AU Patent Application No. 2007288118.
Ohno, et al. 1985, "Antigen-Binding specificities of antibodies are primarily determined by seven residues of VH", Proc. Natl. Acad. Sci. USA, 82(9):2945-2949.
Prince, Biomarkers, "Biomarkers for Diagnosing and Monitoring Autoimmune Diseases," 2005, vol. 10, Supplement 1, pp. S44-S49.
Biomarkers Definitions Working Groups., Clin. Pharmacol. Ther. 69:89-95, 2001.
Kuby in Immunology, Second Edition, W.H. Freeman and Company, New York, 1991; see Chapter 8, Organization and Expression of Immunoglobulin Genes on pp. 175-208.
Nisonoff, Heterogeneity of Antibodies in Introduction to Molecular immunology, Second Edition, Sinauer Associates, Inc. Dunderland, MA, 1985; see Chapter 2: General Structural Properties of Antibodies on pp. 7-28.
Kuby in Immunology, Second Edition, W.H. Freeman and Company, New York, 1991; see Chapter 4, Antigens on pp. 85-108.
Gerard et al., (1993) "Human chemotaxis receptor genes cluster at 19q13.3-13.4. Characterization of the human C5a receptor gene" Biochemistry, vol. 32, No. 5, pp. 1243-1250.
Wong (1999) "Development of C5a receptor antagonists" Drugs, vol. 2, No. 7, pp. 686-693.
Kohl (2001) "Anaphylatoxins and infectious and non-infectious inflammatory diseases" Mol Immunol, vol. 38, Nos. 2-3, pp. 175-187.
Champtiaux & Changeux (2002) "Knock-out and knock-in mice to investiage the role of nicotinic receptors in teh central nervous system" Curr Drug Targets CNS Neurol Discord, vol. 1, No. 4, pp. 319-330.
Drago (2003) "Neuronal nicotinic receptors: insights gained from gene knockout and knockin mutant mice" Cellular Mol Life Sci, vol. 60, No. 7, pp. 1267-1280.
Dymecki, "Flp recombinase promotes site-specific DNA recombination in embryonic stem cells and transgenic mice" Proc Natl Acad Sci USA, Jun. 11, 1996, vol. 93, No. 12, pp. 6191-6196.
Girardi (2003) "Complement C5a receptors and neutrophils mediate fetal injury in the antiphospholipid syndrome" J Clin Invest, vol. 112, No. 11, pp. 1644-1654.
Gu (2003) "Neutropilin-1 conveys semaphorin and VEGF signalling during neutral and cardiovascular development" Dev Cell, vol. 5, No. 1, pp. 45-57.
Heller, Selection of a C5a receptor atagonist from phage libraries attenuating the inflammatory reponse in immune complex disease and ischemia/reperfusion injury, The Journal of Immunology, (1999) vol. 163, pp. 985-994.

(56) References Cited

OTHER PUBLICATIONS

Homanics (2002) "Knockout and Knockin Mice" Methods in Alcohol Related Neuroscience Research, Editor, Liu, Yuan, Chapter 2, pp. 31-61.
Hopken (1996) "The C5a chemoattractant receptor mediates mucosal defence to infection" Nature, vol. 383, No. 6595, pp. 86-89.
Hugli, "The active site of human C4a anaphylatoxin" Mol Immunol, 1983, vol. 20, pp. 637-645.
Kedmi (2003) "Loss of nicotine-induced seizures in double-knockout mice with a5 and b4 neuronal nicotinic acetylcholine receptor subunits deficiency" Society for Neuroscience, Neuroscience 2003 Abstract, Presentation No. 533.12, Nov. 10, 2003.
Labarca, Point mutant mice with hypersensitive a4 nicotinic receptors show dopaminergic deficits and increased anxiety, PNAS 2001, vol. 95, No. 5, pp. 2786-2791.
Layton, Cross-species receptor binding characteristics of human and mouse leukemia inhibitory factor suggest a complex binding interaction, J Biol Chem, 1994, vol. 269, No. 25, pp. 17048-17055.
Lester (2003) "Hypersensitive knockin mouse strains identify receptors and pathways for nicotine action" Curr Opin Drug Discov Devel, vol. 6, No. 5, pp. 633-639.
Lienenklaus et al, "Cutting edge: human anaphylatoxin C4a is a potent agonist of the guinea pig but not the human C3a receptor" J Immunol 1998, vol. 161, pp. 2089-2093.
Liu et al., "The a chain of the IL-2 receptor determines the species specificity of high-affinity IL-2 binding" Cytokine, 1996, vol. 8, No. 8, pp. 613-621.
Mosmann et al., "Species-specificity of T cell stimulating activities of IL 2 and BSF-1 (IL 4): comparison of normal recombinant, mouse and human IL 2 and BSF-1 (IL 4)" J Immunol, 1987, vol. 138, pp. 1813-1816.
Mukherjee et al., "The role of complement anaphylatoxin C5a in neurodegradation: implications in Alzheimer's Disease", J Neuroimmunol, 2000, vol. 105, No. 2, pp. 124-130.
Muller, "Ten years of gene targeting: targeted mouse mutants, from vector design to phenotype analysis", Mech Dev, 1999, vol. 82, pp. 3-21.
Prosser et al., (2002), "Targeted replacement of rodent CCR2 with the human orthologue CCR2B: a mouse model for in vivo analysis of human target-selective small molecule MCP-1 receptor antagonists", Drug Devel Research, vol. 55, No. 4, pp. 197-209.
Roebroek (2003) "Knockin approaches" Methods Mol Biol, vol. 209, pp. 187-200.
Rozmahel (1997) "Incomplete rescue of cystic fibrosis transmembrane conductance regulator deficient mice by the human CFTR cDNA" Hum Mol Genet, vol. 6, No. 7, pp. 1153-1162.
Sato (1999), "Gene trap, gene knockout, gene knock-in, and transgenics in vascular development", Thromb Haemost, vol. 82, No. 2, pp. 865-869.
Smith et al., "Species Specificity of Human and Murine Tumor Necrosos Factor," J Biol Chem, 1986, vol. 261, No. 32, pp. 14871-14874.
Extended European Search Report for European Application No. 10009060.4, dated Jul. 29, 2011.
Farkas, et al. 1999, "C5a Receptor Expression by TGW Neuroblastoma Cells", Neuroreport, 10(14):3021-3025.
Fayyazi, et al. 2000, "The C5a Receptor Is Expressed in Normal Renal Promixal Tubular but Not in Normal Pulmonary or Hepatic Epithelial Cells", Immunology, 99(1):38-45.
Fitzgerald, 1987, "Construction of Immunotoxins Using Pdeudomonas Exotoxin A" Methods Enzymol. 151:139-145.
Gerard & Gerard, 1991, "The Chemotactic Receptor for Human C5a Anaphylatoxin", Nature, 349(6310):614-617.
Gerard & Gerard, 1994. "C5A Anaphylatoxin and Its Seven Transmembrane-Segment Receptor", Annual Review Immunol. 12:775-808.
Gerber, et al. 2001, "An Activation Switch in the Ligand Binding Pocket of the C5a Receptor", Journal Biol. Chem. 276(5):3394-3400.

Hansen & Balthasar, 2002, "Intravenous Immunoglobulin Mediates an Increase in Anti-Platelet Antibody Clearance via the FcRn Receptor", Thromb. Haemost. 88(6):898-899.
Hendrickson, et al. 1995, "High Sencitivity Multanalyte Immunoassay Using Covalent DNA-Labeled Antibodies and Polymerase Chain Reaction", Nucleic Acids Res. 23(3):522-529.
Jagels, et al. 1996, "Proteolytic Inactivation of the Leukocyte C5a Receptor by Proteinases Derived from Porphyomonas Gingivalis", Infect. Immun. 64(6):1984-1991.
Ji, et al. 2002, Arthritis Critically Dependent on Innate Immune System Players, Immunity, 16(2):157-168.
Jones, et al. 1986, "Replacing the Complementarity-Determining Regions in a Human Antibody with Those from a Mouse", Nature, 321(6069):522-525.
Jose, et al. 1994, "Eotaxin: A Potent Eosomophil Chemoattractant Cytokine Detected in a Guinea Pig Model of Allergic Airways Inflammation", Journal Exp. Med. 179(3):881-887.
Kaneko, et al. 1995, "Antagonistic Peptides against Human Anaphylatoxin C5a" Immunology, 86(1):149-154.
Kavanaugh, et al. 1991, "Role of CD11/CD18 in Adhesion and Transendothelial Migration of T Cells. Analysis Utilizing CD18-Deficient T Cells Clones", Journal Immunol. 146(12):4149-4156.
Konteatis, et al. 1994, "Development of C5a Receptor Antagonists. Differential Loss of Funcational Responses", Journal Immunol. 153(9):4200-4205.
Kouskoff, et al. 1996, "Organ-Specific Disease Provoked by Systemic Autoimmunity", Cell, 87(5): 811-822.
Kozlov, et al. 2004, "Efficient Strategies for the Conjugation of Oligonucleotides to Antibodies Enabling Highly Sensitive Protein Detection", Biopolymers, 73(5):621-630.
Kussie, et al. 1994, "A Single Engineered Amino Acid Substitution Changes Antibody Fine Specificity", Journal Immunol. 152(1):146-152.
Kyburz & Corr, 2003, "The KRN Mouse Model of Inflammatory Arthritis", Springer Semin. Immunopathol. 25(1):79-90.
Lebkowski, et al. 1988, "Adeno-Associated Virus: A Vector System for Efficient Introduction and Integration of DNA into a Variety of Mammalian Cell Types", Mol. Cell. Biol. 8(10):3988-3996.
Lee, et al. 2002, "Mast Cells: A Cellular Link between Autoantibodies and Inflammatory Arthritis", Science, 297(5587):1689-1692.
Lee, et al. 2006, "Human C5aR Knock-In Mice Facilitate the Production and Assessment of Anti-Inflammatory Monoclonal Antibodies", Nat. Biotechnol. 24(10):1279-1284.
Lowenstein, et al. 2006 "Different Mechanisms of Campath-1H-Mediaited Depletion for CD4 and CD8 T Cells in Peripheral Blood", Transplant International, 19(11):927-936.
Maccallum, et al. 1996, Antibody-Antigen Interactions: Contact Analysis and Binding Site Topography, Journal Mol. Biol. 262(5):732-745.
Martin, et al. 1989, "Modeling antibody Hypervariable Loops: A Combined Algorithm", Proc. Natl. Acad. Sci. USA, 86(23):9268-9272.
Mayo & Curnutte, 1990, "Kinetic Microplate Assay for Superoxide Production by Neutrophils and Other Phagocytic Cells", Methods Enzymol. 186:567-575.
Monk, et al. 1995, "Mutation of Glutamate 199 of the Human C5a Receptor Defines a Binding Site for Ligand Distinct from the Receptor N Terminus", Journal Biol. Chem. 270(28):16625-16629.
Monk, et al. 2007, "Function, Structure and Therapeutic Potential of Complement C5a Receptors", Br. Journal Pharmacol. 152(4): 429-448.
Morgan, et al. 1993, "Anti-C5a Receptor Antibodies. Characterization of Neutralizing Antibodies Specific for Peptide, C5aR-(9-29), Derived from the Predicted Amino-Terminal Sequence of the Human C5a Receptor", Journal immunol. 151(1):377-388.
Murdoch & Finn, 2000, "Chemokine Receptors and Their Role in Inflammation and Infectious Diseases", Blood, 95(10):3032-3043.
Needleman & Wunsch, 1970, "A General Method Applicable to the Search for Similarities in the Amino Acid Sequence of Two Proteins", Journal Mol. Biol. 48(3): 444-453.
Neote, et al. 1993, "Molecular Cloning, Functional Expression, and Signaling Characteristics of a C-C Chemokine Receptor", Cell, 72(3):415-425.

(56) References Cited

OTHER PUBLICATIONS

Niemeyer, et al. 2003, "Combination of DNA-Directed Immobilization and Immuno-PCR: Very Sensitive Antigen Detection by Means of Self-Assembled DNA-Protein Conjugates", Nucl. Acids Res. 31(16):e90.
Nisihara, et al. 2001, "Humanization and Epitope Mapping of Neutralizing Anti-Human Fas Ligand Monoclonal Antibodies: Structural Insights into Fas/Fas Ligand Interaction", Journal Immunol. 167(6):3266-3275.
Oppermann, et al. 1993, "Probing the Human Receptor for C5a Anaphylatoxin with Site-Directed Antibodies. Identification of the Potential Ligand Binding Site on the NH2-Terminal Domain", Journal Immunol. 151(7):3785-3794.
Pease, et al. 1994, "Generation of Chimeric C5a/Formyl Peptide Receptors: Towards the Identification of the Human C5a Receptor Binding Site", Eur. Journal Immunol. 24(1):211-215.
Pellas, et al. 1998, "Novel C5a Receptor Antagonists Regulate Neutrophil Functions in Vitro and In Vivo", Journal Immunol. 160(11):5616-5621.
Preithner, et al. 2006, "High Concentrations of Therapeutic IgG1 Antibodies Are Needed to Compensate for Inhibition of Antibody-Dependent Cellular Cytotoxicity by Excess Endogenous Immunoglobulin G", Mol. Immunol. 43(8):1183-1189.
Proctor, et al. 2006, "Recent Developments in C5/C5a Inhibitors", Expert Opinion on Therapeutic Patents, 16(4):445-458.
Pulito, et al. 1996, "Humanization and Molecular Modeling of the Anti-CD4 Monoclonal Antibody, OKT4A", Journal Immunol. 156(8):2840-2850.
Queen, et al. 1986, "Cell-Type Specific Regulation of A Kappa Immunoglobulin Gene by Promoter and Enhancer Elements", Immunol. Rev. 89:49-68.
Raffetseder, et al. 1996, "Site-Directed Mutagenesis of Conserved Charged Residues in the Helical Region of the Human C5a Receptor. Arg2O6 Determines High-Affinity Binding Sites of C5a Receptor", Eur, Journal Biochem. 235:(1-2):82-90.
Rothermel, et al. 2000, "Analysis of the Tissue Distribution of the Rat C5a Receptor and Inhibition of C5a-Mediated Effects through the Use of Two MoAbs", Scand. Journal Immunol. 52(4):401-410.
Rudikoff, et al. 1982, "Single Amino Acid Substitution Altering Antigen-Binding Spec", Proc. Natl. Acad. Sci. USA, 79(6):1979-1983.
Sayah, et al. 1999, "Expression of Cytokines by Human Astrocytomas Following Stimulation by C3a Anaphylatoxins: Specific Increase in Interleukin-6 mRNA Expression" Journal Neurochem. 72(6):2426-2436.
Schlaf, et al. 1999, "Differential Expression of the C5a Receptor on the Main Cell Types of the Rat Liver as Demonstrated with a Novel Monoclonal Antibody and by C5a Anaphylatoxin Induced Ca2+ Release", Lab. Invest. 79(10):1287-1297.
Shopes, 1992, "A Genetically Engineered Human IgG Mutant with Enhanced Cytolytic Activity", Journal immunol. 148(9):2918-2922.
Solomon, et al. 2005, "A Crucial Role for Macrophages in the Pathology of K/BxN Serum Induced Arthritis", Euro. Journal immunol. 35(10): 3064-3073.
Stevenson, et al. 1989, "A Chimeric Antibody with Dual Fc Regions (bisRabFc) Prepared by Manipulations at the IgG Hinge", Anticancer Drug Design, 3(4):219-230.
Roitt et al., [Eds], "Antigen Recognition" in Immunology. 5th Edition 1998; TOC and pp. 110-113 (15 pages).
Takeuchi et al., "Flp recombinase transgenic mice of C57BL/6 strain for conditional gene targeting" Biochem Biophys Res Commun, May 10, 2002, vol. 293, No. 3, pp. 953-957.
Wang et al., (2002) "Gain of function mutation of human erythropoietin receptor in mice decreases neointimal formation" Blood, vol. 11, No. 11: Abstract No. 2681.
Woodruff et al (2001) "Species dependence for binding of small molecule agonist and antagonists to the C5a receptor on polymorphonuclear leukocytes" Inflammation, vol. 25, No. 3, pp. 171-177.

Woodruff (2002) "Antiarthritic activity of an orally active C5a receptor antagonist against antigen-induced monarticular arthritis in the rat," Arthritis Rheum, vol. 46, No. 9, pp. 2476-2485.
Translation of Official Action issued by Russian Patent Office dated Jan. 17, 2011, Application No. 2009110154/13(013781) (3 pages).
Casadevall & Janda. Proc Natl Acad Sci USA. "Immunoglobulin isotype influences affinity and specifity." 2012. vol. 109 (31). pp. 12272-12273.
European Examination Report for European Application No. 07784844.8 dated Dec. 3, 2012.
European Examination Report for European Application No. 09713373.0 dated Jan. 8, 2013.
Extended European Search Report for European Application No. 12155157.6 dated Dec. 5, 2012.
GenBank Accession No. AB174081 "Macaca fascicularis brain cDNA clone: QmoA-12145, similar to human reelin (RELN), transcript variant 2, mRNA, RefSeq: NM_173054.1" dated Mar. 6, 2007.
Klco et al. Nat Struct Nol Biol. "Essential ROle for the Second Extracellular Loop in C5a Receptor Activation." 2005. vol. 12(4). pp. 320-326.
Lo. Methods Mol Biol. "Antibody Humanization by CDR Grafting." 2004. vol. 248. pp. 135-159.
Riedemann et al. J Clin Invest. "Increased C5a Receptor Expression in Sepsis." 2002. vol. 110(1). pp. 101-108.
Robinson et al. Drug Develop Res. "Improving Monoclonal Antibodies for Cancer Therapy." 2004. vol. 61. pp. 172-187.
Russian Office Action for Russian Application No. 2010138612 dated Feb. 5, 2013. English Translation.
Sumichika. Curr Opin Invesg Drugs. "C5a Receptor Antagonists for the Treatment of Inflammation." 2004. vol. 5(5). pp. 505-510.
Tomlinson et al. J Mol Biol. "The Repertoire of Human Germline VH Sequences Reveals about Fifty Groups og VH Segments with Different Hypervariable Loops." 1992. vol. 227(3). pp. 776-798.
Tomlinson etl. EMBO J. "The Structural REpertorie of the Human vk Domain." 1995. vol. 14(18). pp. 4628-4638.
Van Den Brink et al. Blood. "Two Classes of Germline Genes Both Derived from the VH1 Family Direct the Formation of Human Antibodies that Recognize Distinct Antigenic Sites in C2 Domain of Factor VIII." vol. 99(8). pp. 2828-2834.
http://blast.ncbi.nlm.nhi.gov/Blast.cgi "Alignment of Human and Mouse C5aR Sequences." Nov. 19, 2012, pp. 1-2.
Anonymous: "Part I: General Requirements for Deposit and Furnishing of Samples", Year Apr. 4, 2006 , XP00551 07484,Retrieved from the Internet: URL:http://www.wipo.intiexport/sites/www/treaties/en/registrationlbudapestiguide/pdf/parU.pdf [retrieved on Mar. 13, 2014.
Anonymous: "Notice from the European Patent Office dated Jul. 7, 2010 concerning inventions which involve the use of or concern biological material", 498 Amtsblatt EPA Official Journal EPO Journal officiel OEB, Year Jan. 1, 2010 (Jan. 1, 2010), pp. 498-513, XP0551 07476,Retrieved from the Internet: URL:http://archive.epo.org/epo/pubs/ojOI 011 0_1 0/10_4980.pdf [retrieved on.
Anonymous: "Part I: General Requirements for Deposit and Furnishing of Samples", Year Apr. 4, 2006 , XP00551 07484,Retrieved from the Internet:URL:http://www.wipo.intiexport/sites/www/treaties/en/registration /budapest/iguide/pdf/part_i.pdf [retrieved on Mar. 13, 2014].
Anonymous: "Notice from the European Patent Office dated Jul. 7, 2010 concerning inventions which involve the use of or concern biological material",498 Amtsblatt EPA Official Journal EPO Journal officiel OEB, Year Jan. 1, 2010 (Jan. 1, 2010), pp. 498-513, XP0551 07476, Retrieved from the internet:URL:http://archive.epo.org/epo/pubs/oj010/10-10/10_ 4980.pdf [retrieved on Mar. 13, 2014].
I. Roitt, J. Brostoff, D. Male. Immunology. Translation from English, M:Mir, 2000, p. 110-113.
Yarlin, A.A. Medicine. "Immunology Principles" 1999, pp. 330-331.
Knittler, M.R. et al. "Molecular chaperones involved in protein degradation in the endoplasmic reticulum: quantitative interaction of the heat shock cognate protein BiP with partially folded immu-

(56) References Cited

OTHER PUBLICATIONS noglobulin light chains that are degraded in the endoplasmic reticulum." Proceedings of the National Academy of Sciences (1995): 92(5): 1764-1768.

Ma Yun et al. "Research development and biological characteristics of C5a" Chinese Journal of Preventive Veterinary Medicine. 2005 vol. 27(4) pp. 317-319.

Whitfeld, P et al. "Humanised Antibodies Targeting the C5A Receptor Reverse Inflammation in the K/BXN Mouse Serum-Transfer Model of Inflammatory Arthritis." European Journal of Immunology, 2009, vol. 39, Suppl.1, S571, WSA06/4.

M Singer et al Genes and Genomes, Moscow, "Mir" 1998 vol. 1 pp. 63-64.

Johswich, K et al "Role of the C5a receptor C5aR) in acute and chronic dextran sulfate-induced models of inflammatory bowel disease" Inflamm Bowel Dis 2009 vol. 15 No. 12 pp. 1812-1823; http://www.ncbi.nlm.nih.gov/pubmed/19714742.

Jacob et al "C5a alters blood-brain barrier integrity in experimental lupus" FASEB J 2010 vol. 24 Issue 6 pp. 1682-1688; http://www.ncbi.nlm.nih.gov/pmc/articles/PMC2874478/.

Abe et al. 2012. "Local Complement-Targeted Intervention in Periodontitis: Proof-of-Concept Using a C5a Receptor (CD88) Antagonist", J Immunol. 189:5442-5448.

Andersson et al. 2012. "Peripheral and Local Effects of Anti-C5aR Treatment in the Collagen Induced Arthritis Model", Arth Reumatism 64(10) Suppl: S881 Abstract.

Andersson et al. 2014. "Rapid-onset clinical and mechanistic effects of anti-C5aR treatment in the mouse collagen-induced arthritis model", Clin Exp Immunol. 177(1):219-233.

Breivik et al. 2011. "Oral treatment with complement factor C5a receptor (CD88) antagonists inhibits experimental periodontitis in rats", J Periodont Res. 46:643-647.

Grant et al. 2002. "Essential Role for the C5a Receptor in Regulating the Effector Phase of Synovial Infiltration and Joint Destruction", Experimental Arthrities.

Hashimoto et al. 2010, "Complement drives Th17 cell differentiation and triggers autoimmune arthritis" J Exp Med. 207(6):1135-1143.

http://blast.ncbi.nlm.nhi.gov/Blast.cgi; "C5a anaphylatoxin chemotactic receptor"; Nov. 19, 2012, pp. 1-2.

Huber-Lang et al. "Structure-Function Relationships of Human C5a and C5aR", J Immunol. 2003, 170:6115-6124.

Johnson, et al., 2012, "Pitfalls and Solutions for the Validation of Novel Drugs in Animal Models of Disease", Current Immunology Reviews 8: 181-189.

Kuby J. 1991. "Organization and Expression of Immunoglobulin Genes" in Immunology, 2nd Ed., W.H. Freeman and Company, New York. Chapter 8, pp. 157-186.

Kuyinu, et al. 2016, "Animal Models of Osteoarthritis: Classification, Update and Measurement of Outcomes," Journal of Orthopaedic Surgery and Research 11:1-27.

Lee, et al. 2008, "Receptors for complement C5a. The importance of C5aR and the enigmatic role of C5L2", Immunol Cell Biol. 86(2):153-160.

Liang et al. 2011. "The C5a Receptor Impairs IL-12-Dependent Clearance of Porphyromonas gingivalis and is Required for Induction of Periodontal Bone Loss", J Immunol. 186:869-877.

Liao et al. 2011. "Clinical predictors of erosion-free status in rheumatoid arthritis: a prosepctive cohort study", Rheumatology 50:1473-1479.

Nansen et al. 2013. "Anti-C5a Receptor Antibody Treatment Aemliorates Disease Activity in Delayed-type Hypersensitivity (DTH) Arthritic Mice", Ann Rheuma Dis. 72(Suppl 3): 809-810.

Recknagel et al. 2012. "C5aR-Antagonist Significantly Reduces the Deleterious Effect of a Blunt Chest Trauma on Fracture Healing", J Ortho Res. 30(4):581-586.

Reinhardt et al. 2000. "C5a modulation of interleukin-1 beta-induced interleukin-6 production by human osteoblast-like cells", J Periodont Res 35:137-145.

Robinson et al. 2004. "Improving Monoclonal Antibodies for Cancer Therapy." Drug Develop Res. 61:172-187.

Seow et al. 2016, "Receptor residence time trumps drug-likeness and oral bioavailability in determining efficacy of complement C5a antagonists", Scientific Reports 6:24575; 13 pages.

Shushakova et al. 2002. "C5a Anapylatoxin is a major regulator of activating versus inhibitory FcGammaRs in immune complex-induced lung disease", J Clin Invest. 110(12):1823-1830.

Tokunaga et al. 2006. "Mechanism of Promotion of Osteoclast Induction by C5A and Suppression by a C5A Receptor Antagonist", Japan Bone Metabolism Society Journal 24 (suppl): Abstract O-073, p. 177.

International Preliminary Report on Patentability and Written Opinion dated Nov. 10, 2015 in PCT/EP2014/059477; 15 pages.

U.S. Office Action dated Sep. 22, 2017 in related U.S. Appl. No. 14/888,141, filed Oct. 30, 2015.

U.S. Response to Restriction filed Dec. 21, 2017 in related U.S. Appl. No. 14/888,141, filed Oct. 30, 2015.

U.S. Office Action dated Mar. 22, 2018 in related U.S. Appl. No. 14/888,141, filed Oct. 30, 2015.

U.S. Response to Office Action filed Jul. 23, 2018 in related U.S. Appl. No. 14/888,141, filed Oct. 30, 2015.

U.S. Office Action dated Nov. 9, 2018 in related U.S. Appl. No. 14/888,141, filed Oct. 30, 2015.

Fig. 1

```
Variable heavy chain regions
                                    CDR1                    CDR2
35F12A2    QVQLVESGGGVVQPGRSLRLSCVASGFTFSNYGMHWVRQAPGKGLEWVAVIWYDGINKYY
35F32A3    QVQLVESGGGLVRPGRSLRLSCAASGFTFRDYGMHWVRQAPGKSLEWVAVIWFDGINKYY
32F3A6     EVQLVQSGGGLVHPGGSLRLSCAGSGFTFSSYVMHWVRQAPGKGLEWVSAIDTGG-GTYY
35F24A3    EVKLVESGGGLVKPGGSLKLSCSASGFAFSNYDMSWVRQTPEKRLEWVAAFSSDG-YTFY
           :*:**:****:*:** **:*** .***:* .:* * ****:* * ****;.:  .* .:*
                                                       CDR3
35F12A2    ADSVKGRFTISRDNSKSTLYLQMNSLRAEDTAVYYCAG--TYYTSGSS-KHFQPWGQGTL
35F32A3    GDSVKGRFTISRDNSKNTLYLQMNSLRAEDTAMYYCVG--TYFGPGTT-EFFQHWGQGTL
32F3A6     ADSVKGRFTISRDNAKNSLYLQMNSLRAEDMAVYYCARDYYYYASGSYYKAFDIWGQGTM
35F24A3    PDSLKGRFTISRDNARNTLYLQMSSLGSEDTALYCCAR----HADYANYPVMDYWGQGTS
           **:*:**********::.:****.** :** *;* *.        .  :   ::  *****

35F12A2    VTVSS
35F32A3    VTVSS
32F3A6     VTVSS
35F24A3    VTVSS
           *****

Variable light chain regions
                                    CDR1                   CDR2
35F12A2    EIVLTQSPATLSLSPGERATLSCRASQSVSS-YLSWYQQKPGQAPRLLIYDASNRATGIP
35F32A3    EIVLTQSPATLSLSPGERATLSCRASQSVSS-YLAWYQQKPGQAPRLLIYDASNRATGIP
32F3A6     EIVLTQSPGTLSLSPGERATLSCRASQSVSSRYLAWYQQKPGQAPRLLIYGASSRATGIP
35F24A3    DIQMTQSPSSLSASVGDRVTITCRASQGISS-WLAWYQQKPEKAPKSLIYAASSLQSGVP
           :* :.****.:** * *:*.*::*****.:** :*:****** :**: *** **. .:*:*
                                CDR3
35F12A2    ARFSGSGSGTDFTLTISSLEPEDFAVYYCQQRSNWP-TFGPGTKVDIKR
35F32A3    ARFSGSGSGTDFTLTISSLEPEDFAVYYCQQRSNWP-TFGPGTKVDIKR
32F3A6     DRFSGSGSGTDFTLTISRLEPEDFAVYYCQQYGSPL-TFGQGTKLEIKR
35F24A3    SRFSGSGSGTDFTLTISSLQPEDFATYYCQQYNSYPRTFGQGTKVEIKR
           ****************  *:*****.***** ..    *** ***:;:***
```

Heavy chain

```
         1         2         3         CDR1            5         CDR2        6
1234 67890123 456789012 4567890123456789012345ABC6789012345AB67890123456789012ABC34567890
EVQL GGGL GGSLRLSC GFTFSSYVMH              WVRQ KGLEWVSAID    TGGGTYYA
EVQL GGGL GGSLRLSC GFTFSSYDMH              WVRQ KGLEWVSAIG    TAGDTYYP
                *                              *                 *

7         8         9                         10                CDR3          11
12345 67890 234567890 2ABC 567 9012345678901 ABC 56789 ABCDEFGHIJK1234567890     <- Kabat
DSVKGRFTISRDNAKNSLYLQMNSLRAEDTAVYYCAR DYTTAGSYYKAFDIWGQGTMVTVS
GSVKGRFTISRDNAKNSLYLQMNSLRAEDTAVYYCAR/ YYYGSGSYY/AFDIWGQGTMVTVS   VH3_13/D3_10/JH3
                *                             *
```

Light chain

```
         1         2         CDR1             3         4           5 CDR2        6
12345678901234567890123456789012345ABCDEF890123456789012345678901234567890123456 7890
EIVLTQSPGTLSLSPGERATLSCRASQS           VSSRYLAWYQQKPGQAPRLLIYGASSRATGIPD
EIVLTQSPGTLSLSPGERATLSCRASQS           VSSSYLAWYQQKPGQAPRLLIYGASSRATGIPD
                                            *

7         8         9 CDR3       10
12345 67890 234567890 2345AB67890123456789     <- The Kabat Scheme
RFSGSGSGTDFTLTISRLEPEDFAVYYCQQYGSP  LTFGQGTKLEIKR
RFSGSGSGTDFTLTISRLEPEDFAVYYCQQYGS   TFGQGTKLEIK     >VKIII_A27/JK2
                          *
```

Fig. 3

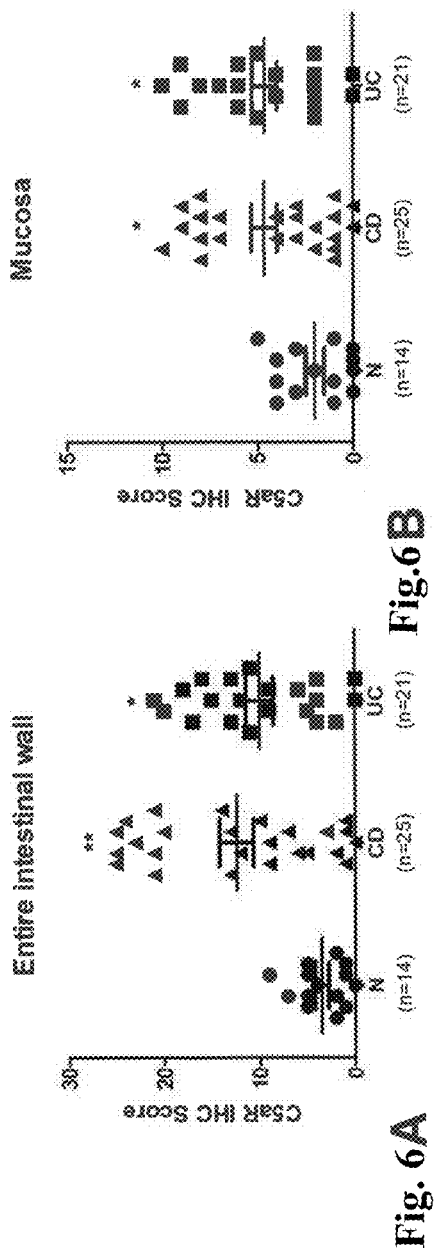
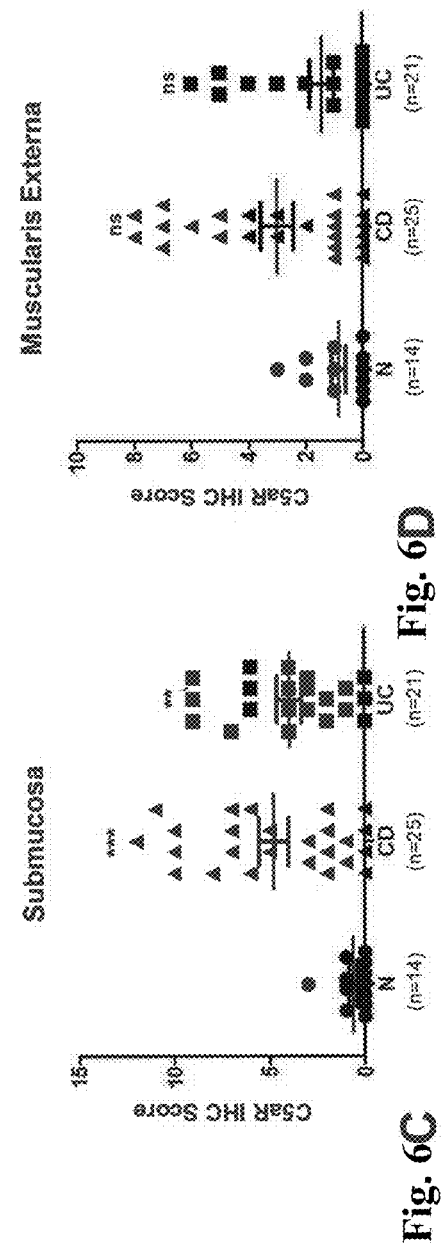
Fig. 6

ANTI-C5A RECEPTOR ANTIBODIES

CROSS-REFERENCE TO RELATED APPLICATIONS

This application is a continuation of U.S. application Ser. No. 14/467,393, filed Aug. 25, 2014 (Pending), which is a continuation of U.S. application Ser. No. 13/920,585, filed Jun. 18, 2013 (U.S. Pat. No. 8,846,045), which is a continuation of U.S. application Ser. No. 13/490,093, filed Jun. 6, 2012 (U.S. Pat. No. 8,613,926) which is a continuation of International Application No. PCT/EP2012/060524 (WO2012/168199), filed Jun. 4, 2012. This application also claims priority to U.S. Provisional Application No. 61/505,137, filed Jul. 7, 2011, and European Patent Application Nos. 11168787.7, filed Jun. 6, 2011 and 12159172.1, filed Mar. 13, 2012, respectively. The contents of all above-named applications are incorporated herein by reference.

SEQUENCE LISTING

The instant application contains a Sequence Listing which has been submitted in ASCII format via EFS-Web and is hereby incorporated by reference in its entirety. Said ASCII copy, created on Jun. 17, 2013, is named 8318214US_SeqList.txt and is 32,808 bytes in size.

TECHNICAL FIELD

The invention relates to the field of therapeutic antibodies.

BACKGROUND

Proteolysis of each of the complement proteins C3-C5 gives rise to amino-terminal cationic fragments with signalling molecules called anaphylatoxins. The most potent of these, C5a, elicits the broadest responses. Considering the components of the inflammatory response as margination and infiltration of leukocytes, release of granule-bound proteolytic enzymes, production of activated oxygen and nitrogen-derived radicals, changes in blood flow and capillary leakage, along with the ability to contract smooth muscle, the C5a molecule is the "complete" pro-inflammatory mediator. At sub-nanomolar to nanomolar levels, the C5a molecule elicits chemotaxis of all myeloid lineages (neutrophils, eosinophils and basophils, macrophages and monocytes), and causes vascular permeability which is markedly potentiated by prostaglandins and circulating leukocytes. Higher nanomolar concentrations elicit degranulation and activation of NADPH oxidase. This breadth of bioactivity contrasts with other inflammatory mediators. C5a is involved in the pathogenesis of various disorders including rheumatoid arthritis, psoriasis, sepsis, reperfusion injury, and adult respiratory distress syndrome (Gerard and Gerard, 1994; Murdoch and Finn, 2000).

The activities of C5a are mediated by the binding of the C5a to its receptor (C5aR). C5aR belongs to the family of seven transmembrane G-protein-coupled receptors. C5aR is a high affinity receptor for C5a, with a Kd of ~1 nM, and is located on a number of different cell types including leukocytes. The number of receptors per cell is extremely high, up to 200,000 sites per leukocyte. Biological activation of the receptor occurs over the range that saturates binding.

The C5aR structure conforms to the seven transmembrane receptor family, with the extracellular N-terminus being followed by seven transmembrane helices connected by interhelical domains alternating as intracellular and extracellular loops, and ending with an intracellular C-terminal domain. C5aR contains an extended N-terminal extracellular domain. This large N-terminal domain is typical of G-protein coupled receptors which bind peptides including the IL-8 and fMet-Leu-Phe (FMLP) receptor families.

Inhibition of the C5a responses with C5aR antagonists reduces the acute inflammatory response mediated via C5a without affecting other complement components. To this end, C5aR peptide antagonists and anti-C5a receptor antibodies have been previously described (Watanabe et al., 1995; Pellas et al., 1998; Konteatis et al., 1994; Kaneko et al., 1995; Morgan et al., 1993). For example, WO 95/00164 describes antibodies directed against an N-terminal peptide (residues 9-29) of C5aR. WO 03/062278 also describes antibodies directed against C5aR. Three of these mouse antibodies were termed 7F3, 6C12 and 12D4. These antibodies were shown to have excellent properties, such as being very effective at blocking C5a binding to its receptor, stopping C5a-directed migration of neutrophils in vitro, and preventing inflammation in animal models. To control chronic diseases it may be necessary to administer the antibody on successive occasions over months or years. However, one drawback from administering mouse antibodies is that the human immune system may generate its own antibodies directed against the mouse antibody (the HAMA response). The HAMA response can neutralize the mouse antibodies by rapidly clearing them from the blood, thus preventing the mouse antibody from binding to its target. To avoid development of a HAMA response one strategy that has been adopted is to "humanize" the mouse antibody by replacing as many "foreign" residues in the non-epitope binding regions with human sequences.

A major problem of humanization procedures has been a loss of affinity for the antigen (Jones et al., 1986), in some instances as much as 10-fold or more, especially when the antigen is a protein (Verhoeyen et al., 1988). Loss of any affinity is, of course, highly undesirable. At the least, it means that more of the humanized antibody will have to be injected into the patient, at higher cost and greater risk of adverse effects. Even more critically, an antibody with reduced affinity may have poorer biological functions, such as complement lysis, antibody-dependent cellular cytotoxicity, or virus neutralization. Although faced with these difficulties successful humanization of anti-human C5aR antibodies has been described in WO 2009/103113.

A plurality of strategies have been developed over the years to further minimize the risk of any unwanted side reaction from administering antibodies to patients, which includes reducing the likelihood of formation of anti-drug antibodies in the patients by generation of "fully" human antibodies.

Even today identification of antibodies suitable for therapeutic applications is a challenging task. Therefore alternative and/or improved C5aR antagonists which can be used in diagnostic and/or therapeutic methods remains of high interest.

SUMMARY

The present invention relates to anti-C5aR antibodies and their use for diagnostic and/or therapeutic methods. The inventors have identified a series of antibodies binding human C5aR which are in several aspects functionally superior to the anti-C5aR antibodies previously described.

As demonstrated herein the inventors have identified a series of human antibodies which bind human C5aR (hC5aR) and can displace hC5a binding to hC5aR and inhibit hC5a mediated neutrophil migration. In addition the inventors have successfully converted non-human residues present in the framework region of one of these anti-hC5aR antibodies to human germline residues without affecting the potency of the antibody.

Furthermore by altering the Fc region the inventors have established an anti-hC5aR antibody which does not induce phagocytosis, ADCC or CDC in vitro. The details of the invention will be apparent from the disclosure of the exemplary embodiments.

An aspect of the invention relates to an antibody wherein the variable region of the heavy chain of said antibody comprises a CDR1, a CDR2 and a CDR3 sequence, wherein said CDR sequences comprises one of the following groups of sequences; SEQ ID 1, 2 and 3, SEQ ID 9, 10 and 11, SEQ ID 17, 18 and 19, SEQ ID 25, 26 and 27 or variants of each of said sequences wherein 1, 2 or 3 amino acid(s) are substituted with a different amino acid residue.

An aspect of the invention relates to an antibody wherein the variable region of the light chain of said antibody comprises a CDR1, a CDR2 and a CDR3 sequence, wherein said CDR sequences comprises one of the following groups of sequences; SEQ ID 5, 6 and 7, SEQ ID 13, 14 and 15, SEQ ID 21, 22 and 23, SEQ ID 29, 30 and 31 or variants of each of said sequences wherein 1, 2 or 3 amino acid(s) are substituted with a different amino acid residue.

An aspect of the invention relates to a human antibody specifically binding hC5aR, wherein said antibody preferably binds the 2nd extracellular loop of hC5aR.

An aspect of the invention relates to an antibody specifically binding hC5aR, wherein the antibody Fc region has been modified compared to IgG1, IgG2, IgG4 and IgG4/G2 reference sequences reducing the ability of the antibodies to induce phagocytosis, ADCC and/or CDC via Fcgamma receptor (FcγR) interaction. In a particular embodiment the antibody Fc region is IgG1 and in further particular embodiment the Fc region comprise one or more of the following groups of point mutations I) N297Q and/or
II) L234A and L235E and/or
III) G236R and L328R and/or
IV) N297Q, L234A and L235E and/or
V) N297Q, L234A, L235E and G237A and/or
VI) L234A, L235E, G237A, A330S and P331S In a further aspect the invention relates to the use of the antibodies according to the invention for treatment of an immunological disease or disorder.

In a further aspect the invention relates to a method for treatment of a disease or disorder comprising administering to a subject in need a therapeutic amount of an antibody as described herein.

In another aspect, the present invention provides a method of treating or preventing a disorder in a subject, the method comprising administering to the subject an antibody of the invention. In one embodiment, the disorder is an immunopathological disorder such as an autoimmune disease.

Further aspect and embodiments of the invention will be apparent from the disclosure herein including exemplary embodiments. It follows from the disclosures that the invention has provided new therapeutic antibodies with various benefits and advantages as characterized herein.

BRIEF DESCRIPTION OF DRAWINGS

FIG. 1 shows alignments of the variable regions (variable heavy chain regions are beginning from the top SEQ ID Nos: 20, 4, 12, and 28, respectively; variable light chain regions are beginning from the top SEQ ID Nos: 24, 8, 16, and 32, respectively) of a selection of monoclonal antibodies isolated and characterized in the application.

FIGS. 2A-2B show binding specificity of a selection of antibodies towards mouse and human C5aR chimeras. Binding of 32F3A6, 35F12A2 and 35F32A3 to chimeric human/mouse CSaR compared to binding of Ref Ab Q. Chimeric receptors are shown schematically. Regions derived from human and mouse CSaR are shown with a fine line and with a heavy line, respectively FIG. 3 shows alignments of the variable regions (the variable heavy and light regions are SEQ ID Nos: 12 and 16, respectively) from one antibody with the nearest germ-line human antibody variable heavy and light sequences. "/" indicates a "break in the sequence, such as between V, D or J segments.

FIGS. 6A-6D Semi-quantitative analysis of the CSaR protein expression in Crohn's disease and ulcerative colitis. CSaR protein expression was investigated by immunohistochemistry and analysed by Kruskal-Wallis test with Dunn's multiple comparison post-test in GRAPHPAD PRISM 5, and P<0.05 was considered significant. * P<0.05;  P<0.01; * P<0.001.

DEFINITIONS

Figures 2, 2B:
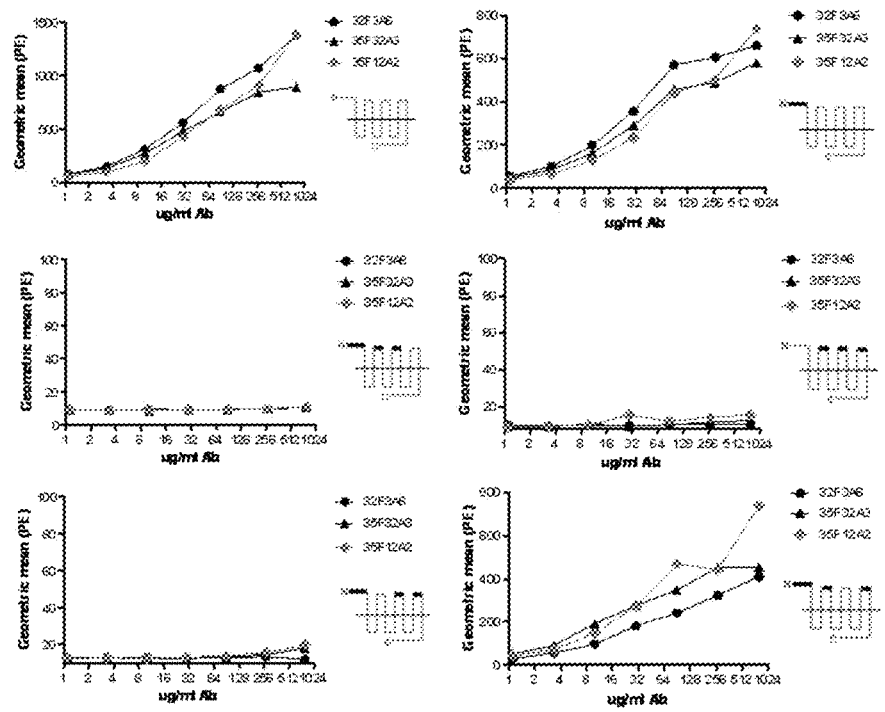

Unless otherwise indicated, the recombinant protein, cell culture, and immunological techniques utilized in the present invention are standard procedures, well known to those skilled in the art. Such techniques are described and explained throughout the literature in sources such as, J. Perbal, A Practical Guide to Molecular Cloning, John Wley and Sons (1984), J. Sambrook et al, Molecular Cloning: A Laboratory Manual, Cold Spring Harbour Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), and F. M. Ausubel et al. (editors), Current Protocols in Molecular Biology, Greene Pub. Associates and Wiley-Interscience (1988, including all updates until present), Ed Harlow and David Lane (editors) Antibodies: A Laboratory Manual, Cold Spring Harbour Laboratory, (1988), and J. E. Coligan et al. (editors) Current Protocols in Immunology, John Wiley and Sons (including all updates until present).

As used herein, "C5a receptor", "C5aR", "C5aRI" or "human C5aR" and variations thereof refers to the human complement component 5 receptor 1 which is also known in the art as the C5a anaphylatoxin receptor and the CD88 antigen. C5aR belongs to the family of seven transmembrane G-protein-coupled receptors, and binds C5a (Gerard and Gerard, 1991). An example of the amino acid sequence of a human C5aR is provided in SEQ ID NO:41, however, as the skilled person will be aware there are naturally occurring allelic variants of this molecule which are also encompassed by the term "C5aR". The various domains of human C5aR are defined as follows:

amino acids 1-37: extracellular domain N-terminus,
amino acids 38-61: transmembrane domain,
amino acids 62-71: intracellular domain,
amino acids 72-94: transmembrane domain,
amino acids 95-110: extracellular domain—extracellular loop 1,
amino acids 111-132: transmembrane domain,
amino acids 133-149: intracellular domain,
amino acids 150-174: transmembrane domain,
amino acids 175-206: extracellular domain—extracellular loop 2,
amino acids 207-227: transmembrane domain,
amino acids 228-242: intracellular domain,
amino acids 243-264: transmembrane domain,
amino acids 265-283: extracellular domain—extracellular loop 3,
amino acids 284-307: transmembrane domain,
amino acids 308-350: intracellular domain—C-terminus.

The term "treatment", as used herein, refers to the medical therapy of any human or other animal subject in need thereof. Said subject is expected to have undergone physical examination by a medical or veterinary medical practitioner, who has given a tentative or definitive diagnosis which would indicate that the use of said specific treatment is beneficial to the health of said human or other animal subject. The timing and purpose of said treatment may vary from one individual to another, according to the status quo of the subject's health. Thus, said treatment may be prophylactic, palliative, symptomatic and/or curative. In terms of the present invention, prophylactic, palliative, symptomatic and/or curative treatments may represent separate aspects of the invention.

In relation to medical treatment the term "subject" as used herein is intended to mean any animal, in particular mammals, such as humans, horses, cows, cats and dogs, and may, where appropriate, be used interchangeably with the term "patient". Preferably, the subject is a human. As used herein the terms "treating", "treat" or "treatment" and variations thereof include administering a therapeutically effective amount of an antibody of the invention sufficient to reduce or eliminate at least one symptom of the disorder.

As used herein the terms "preventing", "prevent" or "prevention" or variations thereof refers to protecting a subject from developing at least one symptom of a disease, or reducing the severity of a symptom of a disorder.

As used herein, the term "exposing the cell" refers to providing the antibody such that it is able to contact/bind human C5aR providing that C5aR is present on the cell.

The term "effective concentration 50 percent" (abbreviated as "EC50") represents the concentration of an antibody of the invention that is required for 50 percent of a given effect of the molecule the antibody targets (e.g. inhibiting/displacing binding of human C5a to human C5aR). It will be understood by one in the art that a lower EC50 value corresponds to a more potent antibody.

As used herein, the term "inhibiting" refers to a significant reduction, and possibly completely abolishing, the defined activity. Preferably, the defined activity is reduced or inhibited by at least 50 percent, more preferably at least 75 percent and even more preferably at least 90 percent.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

In an embodiment, a molecule consists essentially of the defined sequence.

In another embodiment, a molecule consists of the defined sequence.

In an embodiment the molecule such as an antibody or DNA sequence is an isolated molecule. The term "isolated antibody" refers to an antibody that has been separated and/or recovered from another/other component(s) of its natural environment and/or purified from a mixture of components in its natural environment.

The term "antibody", as referred to herein, includes whole antibodies and any antigen binding fragments (i.e., "antigen-binding portion") or single chains thereof. Full-length antibodies (or whole antibodies) comprise four polypeptide chains, two heavy (H) chains and two light (L) chains interconnected by disulfide bonds. Each heavy chain is comprised of a heavy chain variable region (VH) and a heavy chain constant region (CH). Each light chain is comprised of a light chain variable region (VL) and a light chain constant region (CL). The heavy chain constant region is comprised of three domains, CH1, CH2 and CH3. The variable regions of the heavy and light chains contain a binding domain that interacts with the antigen. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR).

Each VH and VL is composed of three CDRs and four FRs, arranged from amino-terminus to carboxy-terminus in the following order: FR1, CDR1, FR2, CDR2, FR3, CDR3, FR4. The constant regions of the antibodies may mediate the binding of the immunoglobulin to host tissues or factors, including various cells of the immune system (e.g., effector cells) and the first component (Clq) of the classical complement system.

As used herein, the term "antibody" is used to describe whole antibodies and any antigen binding fragments (i.e., "antigen-binding portion") or single chains thereof which specifically binds its corresponding antigen. Examples of antigen-binding fragments include Fab, Fab', F(ab)2, F(ab')2, F(ab)S, Fv (typically the VL and VH domains of a single arm of an antibody), single-chain Fv (scFv; see e.g. Bird et al., Science 1988; 242:42S-426; and Huston et al. PNAS 1988; 85:5879-5883), dsFv, Fd (typically the VH and CHI domain), and dAb (typically a VH domain) fragments; VH, VL, VhH, and V-NAR domains; monovalent molecules comprising a single VH and a single VL chain; minibodies, diabodies, triabodies, tetrabodies, and kappa bodies (see, e.g., Ill et al. Protein Eng 1997; 10:949-57); camel IgG; IgNAR; as well as one or more isolated CDRs or a functional paratope, where the isolated CDRs or antigen-binding residues or polypeptides can be associated or linked together so as to form a functional antibody fragment. Various types of antibody fragments have been described or reviewed in, e.g., Holliger and Hudson, Nat Biotechnol 2005; 2S:1126-1136; WO2005040219, and published U.S. Patent Applications 20050238646 and 20020161201.

The term "complementarity-determining region" ("CDR") or "hypervariable region", when used herein, refers to the amino acid residues of an antibody that are responsible for antigen binding. The CDRs are generally comprised of amino acid residues 24-34 (L1), 50-56 (L2) and 89-97 (L3) in the light-chain variable domain and 31-35 (H1), 50-65 (H2) and 95-102 (H3) in the heavy-chain variable domain; (Kabat et al. (1991) Sequences of Proteins of Immunological Interest, Fifth Edition, U.S. Department of Health and Human Services, NIH Publication No. 91-3242) and/or those residues from a "hypervariable loop" (residues 26-32 (L1), 50-52 (L2) and 91-96 (L3) in the light-chain variable domain and 26-32 (H1), 53-55 (H2) and 96-101 (H3) in the heavy-chain variable domain; Chothia and Lesk, J. Mol. Biol 1987; 196:901-917). Typically, the numbering of amino acid residues in this region is performed by the method described in Kabat et al., supra. Phrases such as "Kabat position", "Kabat residue", and "according to Kabat" herein refer to this numbering system for heavy chain variable domains or light chain variable domains. Using the Kabat numbering system, the actual linear amino acid sequence of a peptide may contain fewer or additional amino acids corresponding to a shortening of, or insertion into, a framework (FR) or CDR of the variable domain. For example, a heavy chain variable domain may include amino acid insertions (residue 52a, 52b and 52c according to Kabat) after residue 52 of CDR H2 and inserted residues (e.g. residues 82a, 82b, and 82c, etc. according to Kabat) after heavy chain FR residue 82. The Kabat numbering of residues may be determined for a given antibody by alignment at regions of homology of the sequence of the antibody with a "standard" Kabat numbered sequence.

The term "framework region" or "FR" residues refer to those VH or VL amino acid residues that are not within the CDRs, as defined herein.

The fragment crystallizable region ("Fc region"/"Fc domain") of an antibody is the "tail" region of an antibody that interacts with cell surface receptors called Fc receptors, as well as some proteins of the complement system.

Monoclonal antibodies are typically made by fusing myeloma cells with the spleen cells from a mouse that has been immunized with the desired antigen. Human monoclonal antibodies can be obtained from transgenic animals (e.g. mice or other suitable species) encoding human antibodies. Alternatively, recombinant monoclonal antibodies can be made involving technologies, referred to as repertoire cloning or phage display/yeast display. Recombinant antibody engineering involves the use of viruses or yeast to create antibodies, rather than mice.

The term "humanized antibody", as used herein, refers to a human/non-human chimeric antibody that contains sequences, usually at least the minimal complementarity-determining regions (CDR sequences) derived from a non-human germ line immunoglobulin sequence. A humanized antibody is, thus, a human immunoglobulin (recipient antibody) in which residues from a hyper-variable region of the recipient are replaced by residues from a hypervariable region of a non-human species (donor antibody) such as from a mouse, rat, rabbit, or non-human primate, which have the desired specificity, affinity, and capacity.

The humanized antibodies which comprise at least CDR regions not derived from human germ line sequences and may also be referred to as a "chimeric antibody" if the antibody light and heavy chain genes have been constructed, typically by genetic engineering, from immunoglobulin variable and constant region genes that originate from different species. For example, the variable segments of genes from a mouse monoclonal antibody may be joined to human constant segments.

The term "human antibody", as used herein, is intended to include antibodies having variable regions in which both the framework and CDR regions are derived from human germline immunoglobulin sequences. It is noted that such antibodies may none the less comprise amino acid residues which are not found in the human germline sequences due to mutations occurring due to maturation in vivo or in vitro. Furthermore, if the antibody contains a constant region, the constant region is also primarily derived from human germline immunoglobulin sequences. Human antibodies of the invention may none the less include amino acid residues not encoded by human germline immunoglobulin sequences (e.g., mutations introduced by random or site-specific mutagenesis in vitro or by somatic mutation in vivo). On the other hand, the term "human antibody", as used herein, is not intended to include antibodies or alternative antigenic binding regions in which the CDR sequences are derived from the germline of another mammalian species, such as a mouse and have subsequently been grafted onto human framework sequences (see humanized antibody above). The human antibody may be a human monoclonal antibody. Such a human monoclonal antibody may be produced by a hybridoma which includes a B cell obtained from a transgenic nonhuman animal, e.g., a transgenic mouse, having a genome comprising a human heavy chain transgene and a light chain transgene fused to an immortalized cell. Human antibodies may also be isolated from sequence libraries built on selections of human germline sequences, further diversified with natural and synthetic sequence diversity. Human antibodies may be prepared by in vitro immunisation of human lymphocytes followed by transformation of the lymphocytes with Epstein-Barr virus. The sequence of the human antibody may be identify allowing production of the antibody by recombinant methods.

Furthermore, humanized, human and fully human antibodies may comprise residues that are not found in the recipient antibody or in the donor antibody. These modifications are made to further refine antibody performance.

The term "antibody derivatives" refers to any modified form of the antibody, such as a conjugate of the antibody and another agent or antibody.

The term "antigen" refers to the molecular entity used for immunization of an immunocompetent vertebrate to produce an antibody that recognizes the antigen. Herein the term antigen is used more broadly and is generally intended to include target molecules that are specifically recognized by the antibody, thus including fragments or mimics of the molecule used in the immunization process for raising the antibody or such molecules used for screenings upon immunization and also molecules used for screening in cases where antibodies are obtained by alternative methods such as phage display screening.

The term "epitope", as used herein, is defined in the context of a molecular interaction between an "antigen binding polypeptide", such as an antibody, and its corresponding "antigen". Generally, "epitope" refers to the area or region on an antigen to which an antibody specifically binds, i.e. the area or region in physical contact with the antibody. A protein epitope may comprise amino acid residues in the antigen that are directly involved in binding to the antibody (also called the immunodominant component of the epitope) and other amino acid residues, which are not directly involved in binding, such as amino acid residues of the antigen which are effectively blocked by the Ab (in other words, the amino acid residue is within the "solvent-excluded surface" and/or the "footprint" of the antibody). A given antigen may comprise a number of different epitopes, which may include, without limitation; linear peptide antigenic determinants, conformational antigenic determinants which consist of one or more non-contiguous amino acids located near each other in the native (mature) conformation; and post-translational antigenic determinants which consist, either in whole or part, of molecular structures covalently attached to the antigen, such as carbohydrate groups.

From the fact that descriptions and definitions of epitopes, dependant on the epitope mapping method used, are obtained at different levels of detail, it follows that comparison of epitopes for different Abs on the same Ag can similarly be conducted at different levels of detail.

The terms "binding", "specifically binding" and "binding specificity" is use herein to describe the selectivity of an antibody or an antigen binding fragment thereof.

Antibodies according to the invention may specifically bind C5aR, indicating that the antibody has a significantly lover affinity for other antigens, where significantly lower may be such as at least 2 fold lower, or 5 fold lower or 10 fold lower affinity. The antibody may further be species specific, such as the antibody specifically binds human C5aR but not mouse C5aR with high affinity.

The term "binding affinity" is herein used as a measure of the strength of a non-covalent interaction between two molecules, e.g. an antibody, or fragment thereof, and an antigen. The term "binding affinity" is used to describe monovalent interactions (intrinsic activity). Binding affinity between two molecules, e.g. an antibody, or fragment thereof, and an antigen, through a monovalent interaction may be quantified by determination of the dissociation constant ($K_D$). In turn, $K_D$ can be determined by measurement of the kinetics of complex formation and dissociation, e.g. by the SPR method. The rate constants corresponding to the association and the dissociation of a monovalent complex are referred to as the association rate constant $k_a$ (or $k_{on}$) and dissociation rate constant $k_d$ (or $k_{off}$), respectively. $K_D$ is related to $k_a$ and $k_d$ through the equation $K_D = k_d / k_a$.

Furthermore, "affinity" relates to the strength of the binding between a single binding site of a molecule (e.g., an antibody) and a ligand (e.g., an antigen). The affinity of a molecule X for a ligand Y is represented by the dissociation constant ($K_d$), which is the concentration of Y that is required to occupy the combining sites of half the X molecules present in a solution. A smaller $K_d$ indicates a stronger or higher affinity interaction, and a lower concentration of ligand is needed to occupy the sites. Similarly, the specificity of an interaction may be assessed by determination and comparison of the $K_D$ value for the interaction of interest, such as a specific interaction between an antibody and an antigen, with the $K_D$ value of an interaction not of interest.

Typically, the $K_D$ for the antibody with respect to the target will be 2-fold, preferably 5-fold, more preferably 10-fold less than $K_D$ with respect to the other, non-target molecule such as unrelated material or accompanying material in the environment or control. More preferably, the $K_D$ will be 50-fold less, such as 100-fold less, or 200-fold less; even more preferably 500-fold less, such as 1,000-fold less, or 10,000-fold less.

The value of this dissociation constant can be determined directly by well-known methods, and can be computed even for complex mixtures by methods such as those, for example, set forth in Caceci et al. (Byte 9:340-362, 1984). For example, the $K_D$ may be established using a double-filter nitrocellulose filter binding assay such as that disclosed by Wong & Lohman (Proc. Natl. Acad. Sci. USA 90, 5428-5432, 1993). Other standard assays to evaluate the binding ability of ligands such as antibodies towards targets are known in the art—including, for example, ELISAs, Western blots, RIAs, and flow cytometry analysis. The binding kinetics and binding affinity of the antibody also can be assessed by standard assays known in the art, such as SPR.

A competitive binding assay can be conducted in which the binding of the antibody to the target is compared to the binding of the target by another ligand of that target, such as another antibody. The concentration at which 50% inhibition occurs is known as the Ki. Under ideal conditions, the Ki is equivalent to $K_D$. The Ki value will never be less than the $K_D$, so measurement of Ki can conveniently be substituted to provide an upper limit for $K_D$.

As the skilled person will appreciate, "avidity" relates to the overall strength of interaction between two molecules, such as an antibody and antigen. Avidity depends on both the affinity and the valency of interactions.

Further assays for determining functionality of a given antibodies may include cellular based assay which are specific for the given antigen and the effect of antibody binding.

The term "identity" as known in the art, refers to a relationship between the sequences of two or more polypeptides, as determined by comparing the sequences. In the art, "identity" also means the degree of sequence relatedness between polypeptides, as determined by the number of matches between strings of two or more amino acid residues. "Identity" measures the percent of identical matches between the smaller of two or more sequences with gap alignments (if any) addressed by a particular mathematical model or computer program (i.e., "algorithms"). Identity of related polypeptides can be readily calculated by known methods. Such methods include, but are not limited to, those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; Sequence Analysis Primer, Gribskov, M. and Devereux, J., eds., M. Stockton Press, New York, 1991; and Carillo et al., SIAM J. Applied Math. 48, 1073 (1988).

Preferred methods for determining identity are designed to give the largest match between the sequences tested. Methods of determining identity are described in publicly available computer programs. Preferred computer program methods for determining identity between two sequences include the GCG program package, including GAP (Devereux et al., Nucl. Acid. Res. 12, 387 (1984); Genetics Computer Group, University of Wisconsin, Madison, Ws.), BLASTP, BLASTN, and FASTA (Altschul et al., J. Mol. Biol. 215, 403-410 (1990)). The BLASTX program is publicly available from the National Center for Biotechnology Information (NCBI) and other sources (BLAST Manual, Altschul et al. NCB/NLM/NIH Bethesda, Md. 20894; Altschul et al., supra). The well known Smith Waterman algorithm may also be used to determine identity.

For example, using the computer algorithm GAP (Genetics Computer Group, University of Wisconsin, Madison, Ws.), two polypeptides for which the percent sequence identity is to be determined are aligned for optimal matching of their respective amino acids (the "matched span", as determined by the algorithm). A gap opening penalty (which is calculated as 3.times. the average diagonal; the "average diagonal" is the average of the diagonal of the comparison matrix being used; the "diagonal" is the score or number assigned to each perfect amino acid match by the particular comparison matrix) and a gap extension penalty (which is usually {fraction (1/10)} times the gap opening penalty), as well as a comparison matrix such as PAM 250 or BLOSUM 62 are used in conjunction with the algorithm. A standard comparison matrix (see Dayhoff et al., Atlas of Protein Sequence and Structure, vol. 5, supp.3 (1978) for the PAM 250 comparison matrix; Henikoff et al., Proc. Natl. Acad. Sci USA 89, 10915-10919 (1992) for the BLOSUM 62 comparison matrix) is also used by the algorithm.

Preferred parameters for a peptide sequence comparison include the following: Algorithm: Needleman et al., J. Mol. Biol. 48, 443-453 (1970); Comparison matrix: BLOSUM 62 from Henikoff et al., PNAS USA 89, 10915-10919 (1992); Gap Penalty: 12, Gap Length Penalty: 4, Threshold of Similarity: 0.

The GAP program is useful with the above parameters. The aforementioned parameters are the default parameters for peptide comparisons (along with no penalty for end gaps) using the GAP algorithm.

A "conservative amino acid substitution" may involve a substitution of one amino acid residue with another residue such that there is little or no effect on the polarity or charge of the amino acid residue at that position. This is exemplified by the following groups of amino acids, whereby substitutions of one amino acid with a different amino acid in the same group is considered a conservative substitution: Hydrophilic: Ala, Pro, Gly, Glu, Asp, Gin, Asn, Ser, Thr. Aliphatic: Val, Ile, Leu, Met. Basic: Lys, Arg, His. Aromatic: Phe, Tyr, Trp. Furthermore, any residue may frequently be substituted with alanine.

Furthermore, if desired, unnatural amino acids or chemical amino acid analogues can be introduced as a substitution or addition into the antibody and/or immunoglobulin chain of the present invention. Such amino acids include, but are not limited to, the D-isomers of the common amino acids, 2,4-diaminobutyric acid, a-amino isobutyric acid, 4-aminobutyric acid, 2-aminobutyric acid, 6-amino hexanoic acid, 2-amino isobutyric acid, 3-amino propionic acid, ornithine, norleucine, norvaline, hydroxyproline, sarcosine, citralline, homocitrulline, cysteic acid, t-butylglycine, t-butylalanine, phenylglycine, cyclohexylalanine, beta-alanine, fluoro-amino acids, designer amino acids such as beta-methyl amino acids, Ca-methyl amino acids, Na-methyl amino acids, and amino acid analogues in general.

Amino acid sequence mutants of the antibody and/or immunoglobulin chain of the present invention can be prepared by introducing appropriate nucleotide changes into a nucleic acid of the present invention, or by in vitro synthesis of the desired polypeptide. Such mutants include, for example, deletions, insertions or substitutions of residues within the amino acid sequence. A combination of deletion, insertion and substitution can be made to arrive at the final construct, provided that the final polypeptide product possesses the desired characteristics. Mutant (altered) polypeptides can be prepared using any technique known in the art. For example, a polynucleotide of the invention can be subjected to in vitro mutagenesis. Such in vitro mutagenesis techniques include sub-cloning the polynucleotide into a suitable vector, transforming the vector into a "mutator" strain such as the E. coli XL-I red (Stratagene) and propagating the transformed bacteria for a suitable number of generations. Products derived from mutated/altered DNA can readily be screened using techniques described herein to determine if they have receptor-binding and/or—inhibitory activity.

In designing amino acid sequence mutants, the location of the mutation site and the nature of the mutation will depend on characteristic(s) to be modified. The sites for mutation can be modified individually or in series, e.g., by (1) substituting first with conservative amino acid choices and then with more radical selections depending upon the results achieved, (2) deleting the target residue, or (3) inserting other residues adjacent to the located site.

Amino acid sequence deletions generally range from about 1 to 15 residues, more preferably about 1 to 10 residues and typically about 1 to 5 contiguous residues.

DESCRIPTION

The inventors have identified several aspects of relevance for functionality and efficacy of biological therapeutics and particular antibodies, and the main area of the present invention is antibodies for treatment of inflammatory diseases by inhibition of C5a binding to C5aR.

An aspect of the invention relates to one or more of a series of antibodies which are characterized by their functionality and/or the amino acid sequence of the CDRs, the variable region of the heavy chains and light chains and/or the sequence of the Fc domain.

In one embodiment the antibody is a full length antibody including the standard antibody domains and regions.

In one embodiment the antibody is a antibody fragment, such fragments may be obtained using conventional recombinant or protein engineering techniques. Antibody fragments of the invention may be made by truncation, e.g. by removal of one or more amino acids from the N and/or C-terminal ends of a polypeptide. Fragments may also be generated by one or more internal deletions. An antibody of the invention may be, or may comprise, a fragment of any one of the antibodies on which this invention is based. An antibody of the invention may be, or may comprise, an antigen binding portion of one of these antibodies, or variants thereof. For example, the antibody of the invention may be a Fab fragment of one of these antibodies or variants thereof, or it may be a single chain antibody derived from one of these antibodies, or a variant thereof.

The antibodies of the invention may be from different species including mammalian species such as mouse, rat, rabbit, pig or none human primate. The antibody may be a rodent antibody and more particularly a mouse antibody. Alternatively the antibody may be from a non-mammalian species such as chicken. The antibody may further be a humanized antibody or human antibody.

An antibody of the invention may have the ability to compete with another antibody of the invention for binding to C5aR as described herein. Such cross-competing antibodies can be identified based on their ability to cross-compete with a known antibody of the invention in standard binding assays. Such cross-competition may suggest that the two antibodies bind to identical, overlapping or similar epitopes.

Human Antibodies

As described in the examples herein, the inventors have identified a series of anti-C5aR antibodies derived from transgenic mice including the human immunoglobulin germ line loci. The antibodies are isolated as monoclonal hybridoma antibodies and the binding characteristics evaluated. As mentioned C5aR is a seven transmembrane GPCR and a soluble form that retains the native conformation is not possible to produce. In order to raise human antibodies which block hC5a binding to hC5aR, transgenic mice were immunized with cells expressing native hC5aR. However, blocking antibodies were very difficult to obtain and 32 fusions were performed by the inventors before a human antibody having the desired blocking properties was identified. From 35 fusions and screening of more than 100,000 hybridoma supernatants a total of 11 blocking antibodies were obtained.

Furthermore, due to the nature of hC5aR it was not possible to determine the affinity of the antibodies by standard Biacore analysis, and therefore assays were established based on functional hC5aR-dependent readouts, from which IC50 and EC50 values were determined as described in Example 2 and Example 7.

In one aspect the invention relates to a human antibody binding C5aR and it is further preferred that the antibody binds hC5aR specifically, such that the binding to hC5aR is stronger than binding to C5aR from other species such as in particular mouse C5aR. In one embodiment it is preferred that the antibody binds the 2nd extracellular loop of C5aR and more preferably the $2^{nd}$ loop of human C5aR. In an embodiment the antibody binds the 2nd extracellular loop of human C5aR but not the 2nd extracellular loop of murine C5aR. In further embodiments the antibody according to the invention antibody may bind the 2nd extracellular loop of C5aR in the native conformation only.

The functionality of an anti-C5aR antibody is dependent on the ability of said antibody to significantly inhibit or reduce binding of C5a to C5aR.

In one embodiment the invention relates to a human antibody binding C5aR or to an antibody as described herein by sequence definition (see below) wherein said antibody is capable of significantly inhibiting or reducing binding of C5a to C5aR. This may be determined by a displacement assay (SPA) as described in Example 2 herein, from which 1050 values can be determined. As is apparent from table 1 the 11 antibodies isolated and described have an IC50 concentration below 50 nM. In a further embodiment of the invention the antibody is capable of displacing hC5a in an SPA assay, with an IC50 below 50 nM, such as below 40 nM, such as below 30 nM, such as below 20 nM, such as below 10 nM, such as below 5 nM or even below 4 nM, or with and IC50 below 3 nM or even below 2.5 nM or 2.0 nM.

In further assays the ability of the anti-C5aR antibodies to inhibit C5a-dependent migration of human neutrophils was evaluated and some of the identified human antibodies were found to be more potent inhibitors of C5a-mediated neutrophil migration than a previously described C5aR antibody (Q from WO 2009/103113). In one embodiment the invention thus relates to an antibody as described herein by sequence definition (see below) or a human antibody binding C5aR, wherein said antibody is capable of significantly inhibiting migration of human neutrophils. In one embodiment the antibody inhibits migration to less than 50%, less than 40%, less than 30%, less than 20%, or less than 10% compared to the level of migration observed in the presence of 10 nM C5a and no anti-C5aR antibody. In one such embodiment migration is measured after 30 minutes in the presence of 10 nM C5a and antibody compared to the level of migration observed after 30 minutes in the presence of 10 nM C5a and no antibody. Alternatively the ability of antibody to inhibit neutrophil migration can be express using IC50 values based on the same set up. In one such embodiment the IC50 is below 2.5 µg/ml, such as below 2.5 µg/ml, such as below 1.5 µg/ml, such as below 1.2 µg/ml or even below 1.0 µg/ml.

As an alternative to standard Biacore analysis the functionality of the hC5aR antibodies may be determined by a competition binding assay on neutrophils as described in Example 7. This functionality is referred to as affinity of the antibody as measured by competition ligand binding assay but could also be considered measurement of the avidity of the interaction. The invention in an embodiment relates to an antibody as described herein by sequence definition (see below) or a human antibody binding C5aR, wherein the affinity or avidity of the antibody as measured by competition ligand binding assay on neutrophils is below 0.80 nM, 0.70 nM, 0.60 nM, such as below 0.50 nM, 0.45 nM, 0.40 nM or 0.35 nM.

A further option for characterizing the antibodies was explored using a calcium-flux assay, that measures the ability of an antibody to inhibit C5a induced neutrophil activation ex vivo, likewise described in Example 7. In a further embodiment the invention relates to an antibody as described herein by sequence definition (see below) or a human antibody binding C5aR, wherein the IC50 as determined in a calcium-flux assay is below 7.0 µg/ml, such as below 5.0 µg/ml, such as below 2.5 µg/ml.

Additional ex vivo assays can be used to determine the ability of an antibody to inhibit or neutralize C5a induced neutrophil maturation based on secondary effects such as CD11b and CD62L expression. CD11b and CD62L are maturation markers of neutrophils as they are up and down-regulated, respectively, upon activation by C5a/C5aR interaction.

The effect in a CD11b upregulation assay was determined. In one embodiment, the invention relates to an antibody as described herein by sequence definition (see below) or a human antibody binding C5aR, wherein the IC50 as determined in an CD11 b upregulation assay is below 3.5 µg/ml, such as 3.0 µg/ml, such as below 2.5 µg/ml, such as below 2.0 µg/ml or such as 1.5 µg/ml or even below 1.0 µg/ml.

Likewise, the effect of the antibody in a CD62L down-regulation assay was determined. In one embodiment, the invention relates to an antibody as described herein by sequence definition (see below) or a human antibody binding C5aR, wherein the IC50 as determined in a CD62L down-regulation assay is below 1.8 µg/ml, such as below 1.5 µg/ml, such as below 1.2 µg/ml or even below 1.0 µg/ml.

Four monoclonal antibodies were selected for sequencing to determine the sequence of the variable regions and in particular the CDR sequences. An alignment of sequences is presented in FIG. 1 and the sequences are likewise included in the accompanying sequences listing.

The sequence listing includes the following sequences relating to isolated antibodies:

| SEQ ID 1-3: | Vh 35F32A3 | CDR 1-3 |
| SEQ ID 4: | Vh 35F32A3 | |
| SEQ ID 5-7: | Vl 35F32A3 | CDR 1-3 |
| SEQ ID 8: | Vl 35F32A3 | |

In similar manner, SEQ ID 9-16 describes 32F3A6
In similar manner, SEQ ID 17-24 describes 35F12A2
In similar manner, SEQ ID 25-32 describes 35F24A3

Antibodies Defined by Variable Regions or CDR Sequences

An antibody according to the invention may thus be defined based on the CDR sequences, the sequences of the variable regions of the heavy and light chains and minor modifications hereto which can be performed by the person skilled in the art without altering the functionality of the antibody. This includes amino acid substitutions, deletions or insertions of one or more, such as one, two or three amino acid residues within each of the CDR sequences.

In one aspect the invention relates to an antibody binding C5aR defined by the sequence of the CDR regions, wherein the variable region of the heavy chain of said antibody comprises CDR1, CDR2 and CDR3 sequences selected from the following groups:

a) SEQ ID 1, 2 and 3, where none, one, two or three of said sequences comprise 1, 2 or 3 amino acid(s) substituted with a different amino acid residue; and
b) SEQ ID 9, 10 and 11, where none, one, two or three of said sequences comprise 1, 2 or 3 amino acid(s) substituted with a different amino acid residue; and
c) SEQ ID 17, 18 and 19, where none, one, two or three of said sequences comprise 1, 2 or 3 amino acid(s) substituted with a different amino acid residue; and
d) SEQ ID 25, 26 and 27, where none, one, two or three of said sequences comprise 1, 2 or 3 amino acid(s) substituted with a different amino acid residue.

In one embodiment the invention relates to an antibody binding C5aR, defined by the sequence of the CDR regions, wherein the variable region of the heavy chain of said antibody comprises CDR1, CDR2 and CDR3 sequences;
wherein said CDR1 sequence comprises SEQ ID 1, 9, 17, 25 or one of said sequences wherein 1, 2 or 3 amino acid(s) are substituted with a different amino acid residue; and
wherein said CDR2 sequence comprises SEQ ID 2, 10, 18, 26 or one of said sequence wherein 1, 2 or 3 amino acid(s) are substituted with a different amino acid residue; and
wherein said CDR3 sequence comprises SEQ ID 3, 11, 19, 27 or one of said sequence wherein 1, 2 or 3 amino acid(s) are substituted with a different amino acid residue.

In one embodiment the invention relates to an antibody binding C5aR defined by the sequence of the CDR regions, wherein the variable region of the light chain of said antibody comprises CDR1, CDR2 and CDR3 sequences selected from the following groups
a) SEQ ID 5, 6 and 7, where none, one, two or three of said sequences comprise 1, 2 or 3 amino acid(s) substituted with a different amino acid residue; and
b) SEQ ID 13, 14 and 15, where none, one, two or three of said sequences comprise 1, 2 or 3 amino acid(s) substituted with a different amino acid residue; and
c) SEQ ID 21, 22 and 23, where none, one, two or three of said sequences comprise 1, 2 or 3 amino acid(s) substituted with a different amino acid residue; and
d) SEQ ID 29, 30 and 31, where none, one, two or three of said sequences comprise 1, 2 or 3 amino acid(s) substituted with a different amino acid residue.

In one aspect the invention relates to an antibody binding C5aR, defined by the sequence of the CDR regions, wherein the variable region of the light chain of said antibody comprises CDR1, CDR2 and CDR3 sequences;
wherein said CDR1 sequence comprises SEQ ID 5, 13, 21, 29 or one of said sequences wherein 1, 2 or 3 amino acid(s) are substituted with a different amino acid residue; and
wherein said CDR2 sequence comprises SEQ ID 6, 14, 22, 30 or one of said sequence wherein 1, 2 or 3 amino acid(s) are substituted with a different amino acid residue; and
wherein said CDR3 sequence comprises SEQ ID 7, 15, 23, 31 or one of said sequence wherein 1, 2 or 3 amino acid(s) are substituted with a different amino acid residue.

In one embodiment the invention relates to an antibody where the CDRs of the variable region of the heavy chain comprise SEQ ID 1, 2 and 3 or said sequence with 1, 2 or 3 amino acid substitution(s), deletion(s) and/or insertion(s) and where the CDRs of the variable light chain comprise SEQ ID 5, 6 and 7 or said sequence with 1, 2 or 3 amino acid substitution(s), deletion(s) and/or insertion(s).

In one embodiment the invention relates to an antibody where the CDRs of the variable region of the heavy chain comprise SEQ ID 9, 10 and 11 or said sequence with 1, 2 or 3 amino acid substitution(s), deletion(s) and/or insertion(s) and where the CDRs of the variable light chain comprises SEQ ID 13, 14 and 15 or said sequence with 1, 2 or 3 amino acid substitution(s), deletion(s) and/or insertion(s).

In one embodiment the invention relates to an antibody where the CDRs of the variable region of the heavy chain comprise SEQ ID 17, 18 and 19 or said sequence with 1, 2 or 3 amino acid substitution(s), deletion(s) and/or insertion(s) and where the CDRs of the variable light chain comprises SEQ ID 21, 22 and 23 or said sequence with 1, 2 or 3 amino acid substitution(s), deletion(s) and/or insertion(s).

In one embodiment the invention relates to an antibody where the CDRs of the variable region of the heavy chain comprise SEQ ID 25, 26 and 27 or said sequence with 1, 2 or 3 amino acid substitution(s), deletion(s) and/or insertion(s) and where the CDRs of the variable light chain comprises SEQ ID 29, 30 and 31 or said sequence with 1, 2 or 3 amino acid substitution(s), deletion(s) and/or insertion(s).

An embodiment of the invention thus relates to an antibody, wherein the variable region of the heavy chain of said antibody comprises a CDR1, a CDR2 and a CDR3 sequence, wherein said CDR sequences comprise one of the following groups of sequences; SEQ ID 1, 2 and 3, SEQ ID 9, 10 and 11, SEQ ID 17, 18 and 19, SEQ ID 25, 26 and 27 or said sequences with up to two substitution, deletion and/or insertion per sequence and wherein the variable region of the light chain of said antibody comprises a CDR1, a CDR2 and a CDR3 sequence, wherein said CDR sequences comprise one of the following groups of sequences; SEQ ID 5, 6 and 7, SEQ ID 13, 14 and 15, SEQ ID 21, 22 and 23, SEQ ID 29, 30 and 31 or said sequences with up to two substitution, deletion and/or insertion per sequence.

An embodiment of the invention thus relates to an antibody, wherein the variable region of the heavy chain of said antibody comprises a CDR1, a CDR2 and a CDR3 sequence, wherein said CDR sequences comprise one of the following groups of sequences; SEQ ID 1, 2 and 3, SEQ ID 9, 10 and 11, SEQ ID 17, 18 and 19, SEQ ID 25, 26 and 27 or said sequences with up to one substitution, deletion and/or insertion per sequence and wherein the variable region of the light chain of said antibody comprises a CDR1, a CDR2 and a CDR3 sequence, wherein said CDR sequences comprise one of the following groups of sequences; SEQ ID 5, 6 and 7, SEQ ID 13, 14 and 15, SEQ ID 21, 22 and 23, SEQ ID 29, 30 and 31 or said sequences with up to one substitution, deletion and/or insertion per sequence.

An embodiment of the invention thus relates to an antibody, wherein the variable region of the heavy chain of said antibody comprises a CDR1, a CDR2 and a CDR3 sequence, wherein said CDR sequences comprise one of the following groups of sequences; SEQ ID 1, 2 and 3, SEQ ID 9, 10 and 11, SEQ ID 17, 18 and 19, SEQ ID 25, 26 and 27, and wherein the variable region of the light chain of said antibody comprises a CDR1, a CDR2 and a CDR3 sequence, wherein said CDR sequences comprise one of the following groups of sequences; SEQ ID 5, 6 and 7, SEQ ID 13, 14 and 15, SEQ ID 21, 22 and 23, SEQ ID 29, 30 and 31.

An embodiment of the invention relates to an antibody wherein the variable region of the heavy chain of said antibody comprises a sequence at least 80, 85, 90 or 94% identical to SEQ ID NO: 4, 12, 20 or 28.

In one embodiment the invention relates to an antibody wherein the variable region of the heavy chain of said antibody comprises a sequence at least 96, 97, 98 or 99% identical to SEQ ID NO: 4, 12, 20 or 28.

An aspect of the invention relates to an antibody wherein the variable region of the light chain of said antibody comprises a sequence at least 80, 85, 90 or 94% identical to SEQ ID NO 8, 16, 24 or 32.

In one embodiment of the invention relates to an antibody wherein the variable region of the light chain of said antibody comprises a sequence at least 96, 97, 98 or 99% identical to SEQ ID NO 8, 16, 24 or 32.

An embodiment of the invention thus relates to an antibody, wherein the variable region of the heavy chain of said antibody comprises a sequence at least 80, 85, 90 or 94% identical to SEQ ID NO: 4, 12, 20 or 28 and/or wherein the variable region of the light chain of said antibody comprises a sequence at least 80, 85, 90 or 94% identical to SEQ ID NO 8, 16, 24 or 32.

In one embodiment of the invention relates to an antibody, wherein the variable region of the heavy chain of said antibody comprises a sequence at least 96, 97, 98 or 99% identical to SEQ ID NO: 4 and/or wherein the variable region of the light chain of said antibody comprises a sequence at least 96, 97, 98 or 99% identical to SEQ ID NO 8.

In one embodiment of the invention relates to an antibody, wherein the variable region of the heavy chain of said antibody comprises a sequence at least 96, 97, 98 or 99% identical to SEQ ID NO: 12 and/or wherein the variable region of the light chain of said antibody comprises a sequence at least 96, 97, 98 or 99% identical to SEQ ID NO 16.

In one embodiment of the invention thus relates to an antibody, wherein the variable region of the heavy chain of said antibody comprises a sequence at least 96, 97, 98 or 99% identical to SEQ ID NO: 20 and/or wherein the variable region of the light chain of said antibody comprises a sequence at least 96, 97, 98 or 99% identical to SEQ ID NO 24.

In one embodiment of the invention thus relates to an antibody, wherein the variable region of the heavy chain of said antibody comprises a sequence at least 96, 97, 98 or 99% identical to SEQ ID NO: 28 and/or wherein the variable region of the light chain of said antibody comprises a sequence at least 96, 97, 98 or 99% identical to SEQ ID NO 32.

In one embodiment the invention relates to an antibody wherein the variable region of the heavy chain of said antibody comprises a sequence at least 96, 97, 98 or 99% identical to SEQ ID NO 39 and/or wherein the variable region of the light chain of said antibody comprises a sequence at least 96, 97, 98 or 99% identical to SEQ ID NO 40.

In one embodiment of the invention is an antibody wherein the variable region of the heavy chain of said antibody is identified by SEQ ID NO 39 and/or wherein the variable region of the light chain of said antibody is identified by SEQ ID NO 40.

During maturation of antibodies spontaneous mutations may occur in the framework region, as described herein in Example 6 and 7, the variable region of one of the monoclonal antibodies isolated was compared to human antibody germline sequences to identify the nearest human germ lines sequence for both the variable heavy and light chain. In order to minimize the risk of immunological reaction it was therefore decided to further optimize the antibodies by introducing point mutations at in the framework region to construe an antibody with human germ line sequence in the framework regions, as can be seen from the experiments this did not influence the functionality of the antibody.

In one embodiment the invention relates to an antibody defined by sequence identity to a variable region of a reference antibody as described herein above, wherein the variable region of the heavy chain and/or light chain of said antibody comprises one or more mutations in the framework region. It may, according to the invention be attractive to introduce one or more mutations to increase identity to the nearest human germ line sequence, although other mutations may also be considered. In one embodiment such mutation(s) is/are conservative mutation(s).

Antibodies Defined by Fc Region

The Fc region enables antibodies to activate the immune system and antibodies may be engineered to include modifications within the Fc region, typically to alter one or more of its functional properties, such as serum half-life, complement fixation, Fc-receptor binding, protein stability and/or antigen-dependent cellular cytotoxicity, or lack thereof. Furthermore, an antibody of the invention may be chemically modified (e.g., one or more chemical moieties can be attached to the antibody) or be modified to alter its glycosylation, again to alter one or more functional properties of the antibody.

One aspect of the invention relates to an antibody binding C5aR or an antibody as described herein by sequence definition (see below), wherein the Fc region has a reduced or abolished binding affinity to one or more FcγRs.

In on embodiment the invention relates to an antibody binding C5aR, preferably human C5aR, as described above or an antibody as described herein by sequence definition (see below), wherein the Fc region has reduced binding affinity to one or more FcγRs.

In one embodiment the antibody of the invention displays reduced binding affinity to one or more FcγRs compared to IgG1, IgG2, IgG2/4 or IgG4 Fc reference sequences as defined by SEQ ID NO 33, 34, 35 and 36 respectively. As specific amino acid residues may be responsible for FcγRs interaction and effects meditated here through, it may be advantageous to apply an antibody where such specific amino acid residues of the Fc region have been substituted by a different amino acid.

In one embodiment said Fc region includes one or more point mutations compared to IgG1, IgG2, IgG4/G2 or IgG4Fc reference sequences as defined by SEQ ID 33, 34, 35 and 36 respectively, reducing the affinity to one or more Fcγ receptors or complement components.

In order to evaluate the result of introducing point mutations in the Fc region the effector functions for a series of anti-C5aR antibodies were evaluated as described in Example 4. A phagocytosis assay was established to measure the role of the Fc region in the ability of anti-hC5aR antibodies to induce phagocytosis of neutrophils (expressing hC5aR) by human monocytes. As can be seen from Table 2 several Fc variants decrease the level of phagocytosis induced by the anti-C5aR antibodies in the described assay.

In one embodiment the antibody according to the invention the antibody does not significantly induce phagocytosis of neutrophils in vitro, meaning that the level of phagocytosis is not significantly above background as measured in the absence of an anti-C5aR antibody. In one embodiment the antibody does not give rise to any detectable induction of phagocytosis. The assay for evaluating the level of phagocytosis may be performed using human neutrophils as described in Example 4.

In alternative assays the ability of anti-hC5aR antibodies to induce ADCC (antibody dependent cellular cytotoxicity) and CDC (complement dependent cytotoxicity) were evaluated. The assays were established in order to test the ability of the Fc variants to mediate cell depletion via ADCC or CDC dependent mechanisms, and assumed to be able to mimic activities in an in vivo setting.

The assays apply hC5aR expressing cells as target cells and effector cells (monocyte-depleted PMBCs) or complement containing sera to elicit the responses as described in Example 4.

In one embodiment the antibody according to the invention the antibody does not significantly induce ADCC, meaning that the level of ADCC is not significantly above background as measured in the absence of an anti-C5aR antibody. In one embodiment the antibody does not give rise to any detectable induction of ADCC, that is, the level of ADCC is not above background.

In one embodiment the antibody according to the invention the antibody does not significantly induce CDC. In one embodiment the antibody does not give rise to any detectable induction of CDC, that is, the level of CDC is not above background.

In one embodiment the antibody according to the invention comprise and Fc region where the sequence has been modified to alter the effector cell function or functions. Modification of the Fc sequence may be obtained by point mutations in the amino acid sequence. The heavy chain Fc region may be IgG1, IgG2, IgG4 or a IgG2/4 chimeric sequence. The reference sequences are defined in the sequence listing as follows; IgG1 by SEQ ID NO: 33, IgG2 by SEQ ID NO: 34, IgG2/4 by SEQ ID NO: 35 and IgG4 by SEQ ID NO: 36.

In one embodiment the Fc region is an IgG1 (SEQ ID NO: 33), IgG2 (SEQ ID NO: 34), IgG2/4 (SEQ ID NO: 35), or IgG4 (SEQ ID NO: 36), with one or more of the following point mutations
  a. E233P
  b. L234A or V234A or F234L or F234V
  c. L235E or L235A
  d. G236R or G236A
  e. G237A
  f. S239D
  g. S254W
  h. N297Q
  i. L328R
  j. A330S
  k. P331S
  l. I332E The difference between the Fc variants resides in their ability to interact with FcγRs or components of the complement system as described above. The sequence differences in the Fc region further affects the structure and flexibility of the antibody, which may also affect antibody function. As described in Example 5 and table 3, the inventors further demonstrate that anti-hC5aR antibodies wherein the Fc region is of the IgG1 type with or without additional point mutations are more potent inhibitors of hC5aR mediated effects than corresponding antibodies with the Fc region of the IgG4 type. Accordingly, an embodiment of the invention relates to any of the antibodies defined herein with an Fc region of the IgG1 isotype or at least an Fc hinge region of the IgG1 isotype.

In one embodiment the IgG1 Fc region comprises 1 to 10 amino acid substitutions compared to the IgG1 Fc reference sequence as defined in SEQ ID NO. 33. It is preferred that the Fc regions comprise less mutations, such as 1 to 8 amino acid substitutions within AA 231 to 240, or such as 1 to 5 amino acid substitutions within AA 328 to 334. The amino acid substitutions are preferable selected among substitutions that reduce the ability of the antibody to significantly induce phagocytosis of neutrophils, ADCC and/or CDC in vitro as described above.

In one embodiment the antibody Fc region is an IgG1 comprising one or more of the following point mutations:
  a) N297Q and/or
  b) L234A and/or
  c) L235E or L235A and/or
  d) G236R or G236A and/or
  e) G237A and/or
  f) L328R and/or
  g) A330S and/or
  h) P331S.

In one embodiment the antibody Fc region is an IgG1 comprising one or more of the following groups of point mutations:
  a) N297Q and/or
  b) L234A and L235E and/or
  c) L234A and G236R and/or
  d) L235E and G236R and/or
  e) L234A, L235E and G236R and/or
  f) G236R and L328R and/or
  g) N297Q, L234A and L235E and/or
  h) N297Q, L234A, L235E and G236R and/or
  i) N297Q, L234A, L235E and G237A and/or
  j) L234A, L235E, G237A, A330S and P331 S.
  k) N297Q, L234A, L235E, G237A, A330S and P331S.

In one embodiment the antibody Fc region is an IgG1 comprising one or more of the following groups of point mutations:
  a) N297Q and/or
  b) L234A and L235E and/or
  c) G236R and L328R and/or
  d) N297Q, L234A and L235E and/or
  e) N297Q, L234A, L235E and G237A and/or
  f) L234A, L235E, G237A, A330S and P331 S.

It is clear to the skilled person that point mutations within the framework region of both heavy and light chains may be introduced based on standard criteria for substituting amino acid residues is within the scope of the invention. Functional assays as described herein may be used to confirm that such mutations do not influence functionality of the antibody.

As is apparent from the above the binding specificity of the identified antibodies is provided by the variable regions or CDRs, and is clear that different types of antibodies possessing a similar antigenic binding region are encompassed by the invention.

In one embodiment of the invention the antibody is a full length antibody. In one embodiment of the invention the antibody is an antibody fragment or a single chain antibody. In one embodiment the antibody is a monoclonal antibody. In one embodiment the antibody is a human, mouse, rat, rabbit, pig or non-human primate antibody. In one embodiment the antibody is a mouse or human antibody. In one embodiment the antibody is a human antibody. In one embodiment the antibody is a humanized antibody. As described in the definition part of the application a humanized antibody includes at least CDR regions not derived from the human germ line sequence. As is further apparent from the above a human antibody may comprise one or more point mutations compared to the germ line sequence but it is generally considered that the sequence should at least in the framework region or Fc region be at least 95% identity to human germ line sequences.

Pharmaceutical Formulations

The present invention further includes pharmaceutical compositions/formulations, comprising a pharmaceutically acceptable carrier and a polypeptide or antibody according to the invention, as well as kits comprising such compositions.

The antibody according to the invention may in an aspect of the invention be formulated in a pharmaceutical composition. Such a pharmaceutical composition may be prepared based on general knowledge in the field such as in the Pharmacopeia or Remington.

In an embodiment the pharmaceutical composition according to the invention comprise an antibody as described here in combination with a pharmaceutically acceptable carrier. The formulation may be in the form of an aqueous formulation or a dry formulation that is reconstituted in water or an aqueous buffer composition prior to administration.

A pharmaceutical composition of antibodies according to the invention may comprise a salt and/or buffer, such as the compositions described in WO2011/104381.

In further embodiment the pharmaceutical composition of antibodies according to the invention may be suitable for multiple uses, such as the compositions described in WO2011/147921

Method of Treatment

An aspect of the invention relates to a method for treating or preventing a disorder in a subject, the method comprising administering to a subject in need a therapeutic amount of an antibody as described herein. As described in previous publications such as WO 2009/103113 anti-C5aR antibodies are usable/suitable for treatment of various diseases and disorders. An embodiment of the invention thus relates to a method for treatment of an immunological disease or disorder in particular an inflammatory disease. Example 8 herein further supports this by demonstrating functionality of an anti-C5aR antibody according to the invention in a mice arthritis model. Examples 9-11 demonstrates up-regulation of C5aR in tissue samples from psoriatic arthritis, Crohn's and ulcerative colitis patients. It is further demonstrated that an anti-C5aR antibody can inhibit cell migration of PMNs induced by synovial fluid from psoriatic arthritis patients.

A method of treatment may aim at curing a disease or disorder, but in relation to some diseases including immunological and inflammatory diseases such as a chronic disease or disorder, relief of one or more symptoms is also considered a treatment, which may be a significant improvement for the subject even if only a partial relief of symptoms is obtained or the effect is only temporary or partial The method according to the invention includes treatment of one or more diseases including, but not limited to, rheumatoid arthritis (RA), psoriasis, psoriatic arthritis, systemic lupus erythematosus (SLE), lupus nephritis, type I diabetes, Grave's disease, Inflammatory bowel disease (IBD), Crohn's disease (CD), ulcerative colitis (UC), irritable bowel syndrome, multiple sclerosis (MS), autoimmune myocarditis, Kawasaki disease, coronary artery disease, chronic obstructive pulmonary disease (COPD), interstitial lung disease, autoimmune thyroiditis, scleroderma, systemic sclerosis, osteoarthritis, atoptic dermatitis, vitiligo, graft vs. host disease, Sjogren's syndrome, autoimmune nephritis, Goodpasture's syndrome, chronic inflammatory demyelinating polyneuropathy, ANCA-associated vasculitis, uveitis, scleroderma, bullous pemphigoid, Alzheimer's Disease, amyotrophic lateral sclerosis, Huntington's Chorea, cystic fibrosis, gout, age-related macular degeneration, allergy, asthma and other autoimmune diseases that are a result of either acute or chronic inflammation. In a further embodiment the disease or disorder is an acute or chronic inflammation, wherein the disorder may be an auto-immune disease. In an embodiment the disorder is rheumatoid arthritis (RA), psoriatic arthritis, systemic lupus erythematosus (SLE), lupus nephritis, Inflammatory bowel disease (IBD) including Crohn's disease (CD) or ulcerative colitis (UC) or irritable bowel syndrome. In further embodiments the disorder is RA or SLE. Apart from chronic diseases anti-C5aR antibodies may be relevant in relation to acute indications such as transplantation, ischemia/reperfusion injury (e.g. acute myocardial infarction, stroke), sepsis (e.g. SIRS, MODS, ALI), atherosclerosis and intracerebral haemorrhage (ICH).

In a further aspect the invention relates to an antibody, an isolated antibody or antibody composition as described herein, for treatment of a disease or disorder. In further embodiment said antibody, isolated antibody or antibody composition is for treatment of one or more of the diseases and disorders described herein above in relation to a method of treatment.

An aspect of the invention relates to the use of an antibody, an isolated antibody or antibody composition as described herein, for the preparation of a medicament for treatment of a disease or disorder, wherein the disease or disorder may be as described herein above in relation to a method of treatment.

Mode of Administration

An antibody of the invention may be administered parenterally, such as intravenously, such as intramuscularly, such as subcutaneously. Alternatively, an antibody of the invention may be administered via a non-parenteral route, such as per-orally or topically. An antibody of the invention may be administered prophylactically. In a preferred embodiment the antibody is administered intravenously or subcutaneously.

The dosage and timing of administration will most likely depend on various factors including the disease/disorder or symptoms of concern as well as the subject in question. In general it is expect that the antibody is administered in doses from 0.010 mg/kg up to 4-6 mg/kg. Likewise the dosage regiment of the antibody will also depend on the individual subject and disease state of said subject, but it is desirable according to the invention to employ a treatment where the antibody (or antibody composition) is administered to the subject once weekly or every 2 weeks or even at lower intervals, such as once a month.

An antibody of the invention may be administered on demand, that is the antibody may be administered based on the patients experience e.g. when particular symptoms arise or when the amount of particular biomarkers reaches a predefined level.

Specific Combination Treatments

Antibodies of the invention may be co-administered with one or other more other therapeutic agents or formulations. The other agent may be an agent that enhances the effects of antibodies of the invention. The other agent may be intended to treat other symptoms or conditions of the patient. For example, the other agent may be an analgesic, an immunosuppressant or an anti-inflammatory agent. The other agent may be another monoclonal antibody, such as one of those described in international patent applications WO 2008/022390 and WO 2009/103113

Combined administration of two or more agents may be achieved in a number of different ways. In one embodiment, the antibody and the other agent may be administered together in a single composition. In another embodiment, the antibody and the other agent may be administered in separate compositions as part of a combined therapy. For example, the modulator may be administered before, after or concurrently with the other agent.

The antibodies according to the present invention may be administered along with other drugs (e.g. methotrexate, dexamethasone, and prednisone) and/or other biological drugs. In one embodiment according to the invention an antibody may be coadministered with one or more therapeutic agent(s) selected from the ATC code M01C class of anti-rheumatic drugs and ATC code L04 of immunosuppressants as described in WO 2009/103113 including, but not limited to, azathioprine, chloroquine, hydroxychloroquine, cyclosporine, D-penicillamine, gold salts (sodium aurothiomalate, auranofm), leflunomide, methotrexate, minocycline, sulfasalazine and cyclophosphamide, glucocorticosteroids, mycophenolic acid or mycophenolate and tacrolimus and in separate embodiment one or more of Plaquenil, Azulfidine and Methotrexate, dexamethasone and/or prednisone.

In another example, the antibodies of the present invention can also be used in combination with other antibodies (e.g., in combination with antibodies which bind chemokine receptors, including, but not limited to, CCR2 and CCR3) or with anti-TNF or other anti-inflammatory agents or with existing blood plasma products, such as commercially available gamma globulin and immune globulin products used in prophylactic or therapeutic treatments. The antibodies of the present invention can be used as separately administered compositions given in conjunction with antibiotics and/or antimicrobial agents.

Antibodies may according be administered in combination with agents such as agents already in use in autoimmunity including, but are not limited to, immune modulators such as IFN-beta, Orencia™ (CTLA4-Ig), Humira™ (anti-TNF), Cimzia™ (anti-TNF, PEG Fab), Tysabri™ (a4-integrin mAb), Simponi™, Rituxan/MabThera™, Actemra/RoActemra™, Kineret™, Raptiva, Ustekimumab, Non-steroidal anti-inflammatory drugs (NSAIDS) like Asprin™ Ibuprofen™ etc, Corticosteroids, disease-modifying anti-rheumatic drugs (DMARDS) like Plaquenil™ Azulfidine™ Methotrexate™ etc, Copaxone™ (glatirimer acetate), Gilneya™ (fingolimod), antibiotics like Flagyl™, Cipro™, Topical (skin applied) medications including topical corticosteroids, vitamin D analogue creams (Dovonex™), topical retinoids (Tazorac™), moisturizers, topical immunomodulators (tacrolimus and pimecrolimus), coal tar, anthralin, and others, and additionally also light therapy like PUVA, UVB and CellCept™ (mycophenolate mofetil) may be combined with treatment using antibodies according to the invention.

It may be that the subject to be treated is already being treated with one or more other drug(s) in case the antibody of the invention may be added to said treatment regimen.

Method for Antibody Preparation

An antibody may be prepared by various methods know in the art mainly relying on either hybridoma clones for production of the antibody or expression of the antibody in a recombinant host, where the latter is described in WO2010/000864. Based on knowledge in the art a nucleotide sequence encoding a desired antibody chain can be constructed and used for recombinant expression of an antibody where the heavy and light chain may be expressed from one or two separate polynucleotides.

The present invention in a further aspect relation to one or more isolated polynucleotide(s) encoding a polypeptide sequence of an antibody chain of an antibody described herein.

A further embodiment relates to a host cell comprising one or more polynucleotide(s) encoding a polypeptide sequence(s) of an antibody chain of an antibody described herein.

The invention further relation to a process for producing an antibody according to the invention, comprising culturing a host cell described above under conditions supporting expression of one or more polypeptide sequence(s) of an antibody chain. The process may further include that the antibody chains are encoded by two separate open reading frames on one contiguous polynucleotide and optionally that the antibody is recovered from said host cell culture.

The present invention may, without being limited hereto, be described by the following embodiments.

Embodiments

1. An antibody wherein the variable region of the heavy chain of said antibody comprises a CDR1, a CDR2 and a CDR3 sequence,
   wherein said CDR1 sequence comprises SEQ ID 1 or said sequence with 1, 2 or 3 amino acid(s) substitutions, deletions or insertions and/or
   wherein said CDR2 sequence comprises SEQ ID 2 or said sequence with 1, 2 or 3 amino acid(s) substitutions, deletions or insertions and/or
   wherein said CDR3 sequence comprises SEQ ID 3 or said sequence with 1, 2 or 3 amino acid(s) substitutions, deletions or insertions.

2. An antibody wherein the variable region of the heavy chain of said antibody comprises a CDR1, a CDR2 and a CDR3 sequence, wherein said CDR sequences comprises SEQ ID 1, 2 and 3 or variants of said sequences wherein 1, 2 or 3 amino acid(s) are substituted with a different amino acid residue.

3. An antibody wherein the variable region of the heavy chain of said antibody comprises a CDR1, a CDR2 and a CDR3 sequence, wherein said CDR sequences are identical to SEQ ID 1, 2 and 3.

4. An antibody wherein the variable region of the light chain of said antibody comprises a CDR1, a CDR2 and a CDR3 sequence,
   wherein said CDR1 sequence comprises SEQ ID 5 or said sequence with 1, 2 or 3 amino acid(s) substitutions, deletions or insertions and/or
   wherein said CDR2 sequence comprises SEQ ID 6 or said sequence with 1, 2 or 3 amino acid(s) substitutions, deletions or insertions and/or
   wherein said CDR3 sequence comprises SEQ ID 7 or said sequence with 1, 2 or 3 amino acid(s) substitutions, deletions or insertions.

5. An antibody wherein the variable region of the light chain of said antibody comprises a CDR1, a CDR2 and a CDR3 sequence, wherein said CDR sequences comprises SEQ ID 5, 6 and 7 or variants of said sequences wherein 1, 2 or 3 amino acid(s) are substituted with a different amino acid residue.

6. An antibody wherein the variable region of the light chain of said antibody comprises a CDR1, a CDR2 and a CDR3 sequence, wherein said CDR sequences are identical to SEQ ID 5, 6 and 7.

7. An antibody wherein the variable region of the heavy chain is defined as in any of the embodiments 1, 2 or 3 and wherein the variable region of the light chain is defined as in any of the embodiments 4, 5 or 6.

8. An antibody wherein the variable region of the heavy chain of said antibody comprises a CDR1, a CDR2 and a CDR3 sequence, wherein said CDR1 sequence comprises SEQ ID 9 or said sequence with 1, 2 or 3 amino acid(s) substitutions, deletions or insertions and/or
wherein said CDR2 sequence comprises SEQ ID 10 or said sequence with 1, 2 or 3 amino acid(s) substitutions, deletions or insertions and/or
wherein said CDR3 sequence comprises SEQ ID 11 or said sequence with 1, 2 or 3 amino acid(s) substitutions, deletions or insertions.

9. An antibody wherein the variable region of the heavy chain of said antibody comprises a CDR1, a CDR2 and a CDR3 sequence, wherein said CDR sequences comprises SEQ ID 9, 10 and 11 or variants of said sequences wherein 1, 2 or 3 amino acid(s) are substituted with a different amino acid residue.

10. An antibody wherein the variable region of the heavy chain of said antibody comprises a CDR1, a CDR2 and a CDR3 sequence, wherein said CDR sequences are identical to SEQ ID 9, 10 and 11.

11. An antibody wherein the variable region of the light chain of said antibody comprises a CDR1, a CDR2 and a CDR3 sequence,
wherein said CDR1 sequence comprises SEQ ID 13 or said sequence with 1, 2 or 3 amino acid(s) substitutions, deletions or insertions and/or
wherein said CDR2 sequence comprises SEQ ID 14 or said sequence with 1, 2 or 3 amino acid(s) substitutions, deletions or insertions and/or
wherein said CDR3 sequence comprises SEQ ID 15 or said sequence with 1, 2 or 3 amino acid(s) substitutions, deletions or insertions.

12. An antibody wherein the variable region of the light chain of said antibody comprises a CDR1, a CDR2 and a CDR3 sequence, wherein said CDR sequences comprises SEQ ID 13, 14 and 15 or variants of said sequences wherein 1, 2 or 3 amino acid(s) are substituted with a different amino acid residue.

13. An antibody wherein the variable region of the light chain of said antibody comprises a CDR1, a CDR2 and a CDR3 sequence, wherein said CDR sequences are identical to SEQ ID 13, 14 and 15.

14. An antibody wherein the variable region of the heavy chain is defined as in any of the embodiments 8, 9 or 10 and wherein the variable region of the light chain is defined as in any of the embodiments 11, 12 or 13.

15. An antibody wherein the variable region of the heavy chain of said antibody comprises a CDR1, a CDR2 and a CDR3 sequence,
wherein said CDR1 sequence comprises SEQ ID 17 or said sequence with 1, 2 or 3 amino acid(s) substitutions, deletions or insertions and/or
wherein said CDR2 sequence comprises SEQ ID 18 or said sequence with 1, 2 or 3 amino acid(s) substitutions, deletions or insertions and/or
wherein said CDR3 sequence comprises SEQ ID 19 or said sequence with 1, 2 or 3 amino acid(s) substitutions, deletions or insertions.

16. An antibody wherein the variable region of the heavy chain of said antibody comprises a CDR1, a CDR2 and a CDR3 sequence, wherein said CDR sequences comprises SEQ ID 17, 18 and 19 or variants of said sequences wherein 1, 2 or 3 amino acid(s) are substituted with a different amino acid residue.

17. An antibody wherein the variable region of the heavy chain of said antibody comprises a CDR1, a CDR2 and a CDR3 sequence, wherein said CDR sequences are identical to SEQ ID 17, 18 and 19.

18. An antibody wherein the variable region of the light chain of said antibody comprises a CDR1, a CDR2 and a CDR3 sequence,
wherein said CDR1 sequence comprises SEQ ID 21 or said sequence with 1, 2 or 3 amino acid(s) substitutions, deletions or insertions and/or
wherein said CDR2 sequence comprises SEQ ID 22 or said sequence with 1, 2 or 3 amino acid(s) substitutions, deletions or insertions and/or
wherein said CDR3 sequence comprises SEQ ID 23 or said sequence with 1, 2 or 3 amino acid(s) substitutions, deletions or insertions.

19. An antibody wherein the variable region of the light chain of said antibody comprises a CDR1, a CDR2 and a CDR3 sequence, wherein said CDR sequences comprises SEQ ID 21, 22 and 23 or variants of said sequences wherein 1, 2 or 3 amino acid(s) are substituted with a different amino acid residue.

20. An antibody wherein the variable region of the light chain of said antibody comprises a CDR1, a CDR2 and a CDR3 sequence, wherein said CDR sequences are identical to SEQ ID 21, 22 and 23.

21. An antibody wherein the variable region of the heavy chain is defined as in any of the embodiments 15, 16 or 17 and wherein the variable region of the light chain is defined as in any of the embodiments 18, 19 or 20.

22. An antibody wherein the variable region of the heavy chain of said antibody comprises a CDR1, a CDR2 and a CDR3 sequence,
wherein said CDR1 sequence comprises SEQ ID 25 or said sequence with 1, 2 or 3 amino acid(s) substitutions, deletions or insertions and/or
wherein said CDR2 sequence comprises SEQ ID 26 or said sequence with 1, 2 or 3 amino acid(s) substitutions, deletions or insertions and/or
wherein said CDR3 sequence comprises SEQ ID 27 or said sequence with 1, 2 or 3 amino acid(s) substitutions, deletions or insertions.

23. An antibody wherein the variable region of the heavy chain of said antibody comprises a CDR1, a CDR2 and a CDR3 sequence, wherein said CDR sequences comprises SEQ ID 25, 26 and 27 or variants of said sequences wherein 1, 2 or 3 amino acid(s) are substituted with a different amino acid residue.

24. An antibody wherein the variable region of the heavy chain of said antibody comprises a CDR1, a CDR2 and a CDR3 sequence, wherein said CDR sequences are identical to SEQ ID 25, 26 and 27.

25. An antibody wherein the variable region of the light chain of said antibody comprises a CDR1, a CDR2 and a CDR3 sequence,
wherein said CDR1 sequence comprises SEQ ID 29 or said sequence with 1, 2 or 3 amino acid(s) substitutions, deletions or insertions and/or
wherein said CDR2 sequence comprises SEQ ID 30 or said sequence with 1, 2 or 3 amino acid(s) substitutions, deletions or insertions and/or
wherein said CDR3 sequence comprises SEQ ID 31 or said sequence with 1, 2 or 3 amino acid(s) substitutions, deletions or insertions.

26. An antibody wherein the variable region of the light chain of said antibody comprises a CDR1, a CDR2 and a CDR3 sequence, wherein said CDR sequences comprises SEQ ID 29, 30 and 31 or variants of said sequences wherein 1, 2 or 3 amino acid(s) are substituted with a different amino acid residue.

27. An antibody wherein the variable region of the light chain of said antibody comprises a CDR1, a CDR2 and a CDR3 sequence, wherein said CDR sequences are identical to SEQ ID 29, 30 and 31.
28. An antibody wherein the variable region of the heavy chain is defined as in any of the embodiments 22, 23 or 24 and wherein the variable region of the light chain is defined as in any of the embodiments 25, 26 or 27.
29. An antibody wherein the variable region of the heavy chain of said antibody comprises a sequence at least 80, 85, 90 or 94% identical to SEQ ID NO: 4, 12, 20 or 28.
30. The antibody according to embodiment 29, wherein the variable region of the heavy chain of said antibody comprises one or more mutations in the framework region.
31. The antibody according to embodiment 29, wherein said mutation(s) are conservative mutations.
32. The antibody according to embodiment 29, wherein said mutation(s) increase identity to the nearest human germ line sequence.
33. The antibody according to embodiment 32, wherein the variable region of the heavy chain of said antibody is identified by SEQ ID NO 39.
34. An antibody wherein the variable region of the light chain of said antibody comprises a sequence at least 80, 85, 90 or 94% identical to SEQ ID NO: 8, 16, 24 or 32.
35. The antibody according to embodiment 34, wherein the variable region of the light chain of said antibody comprises one or more mutations in the framework region.
36. The antibody according to embodiment 35, wherein said mutation(s) are conservative mutations.
37. The antibody according to embodiment 35, wherein said mutation(s) increase identity to the nearest human germ line sequence.
38. The antibody according to embodiment 34, wherein the variable region of the light chain of said antibody is identified by SEQ ID NO 40.
39. An antibody wherein the variable region of the heavy chain of said antibody comprises a sequence at least 80, 85, 90 or 94% identical to SEQ ID NO: 4, 12, 20 or 28 and wherein the variable region of the light chain of said antibody comprises a sequence at least 80, 85, 90 or 94% identical to SEQ ID NO: 8, 16, 24 or 32.
40. The antibody according to embodiment 39, wherein the sequence of said heavy chain variable regions has at least 96%, such as 97%, such as 98% or such as 99% identity to SEQ ID NO: 4, 12, 20 or 28 and wherein the sequence of said light chain variable region has at least 96%, such as 97%, such as 98% or such as 99% identity to SEQ ID NO: 8, 16, 24 or 32.
41. The antibody according to embodiment 39 or 40, wherein the variable region of the heavy chain of said antibody comprises one or more mutations in the framework region and/or wherein the variable region of the light chain of said antibody comprises one or more mutations in the framework region.
42. The antibody according to embodiment 41, wherein said mutation(s) are conservative mutations.
43. The antibody according to embodiment 41, wherein said mutation(s) increase identity to the nearest human germ line sequence.
44. The antibody according to embodiment 41, wherein the variable region of the heavy chain of said antibody is identified by SEQ ID NO 39 and/or wherein the variable region of the light chain of said antibody is identified by SEQ ID NO 40.
45. The antibody according to any of the previous embodiments, wherein said antibody binds C5aR.
46. The antibody according to any of the previous embodiments, wherein said antibody is a full length antibody or an antibody fragment or a single chain antibody.
47. The antibody according to any of the previous embodiments, wherein said antibody is a monoclonal antibody.
48. The antibody according to any of the previous embodiments wherein said antibody is a human, mouse, rat, rabbit, pig or non-human primate antibody.
49. The antibody according to any of the previous embodiments, wherein said antibody is a mouse or human antibody.
50. The antibody according to any of the previous embodiments, wherein said antibody is a human antibody or a humanized antibody.
51. The antibody according to any of the previous embodiments, wherein said antibody is a human antibody.
52. A human antibody binding C5aR.
53. The antibody according to any of the previous embodiments, wherein said antibody binds human C5aR.
54. The antibody according to any of the previous embodiments, wherein said antibody binds the 2nd extracellular loop of C5aR.
55. The antibody according to any of the previous embodiments, wherein said antibody binds the 2nd extracellular loop of human C5aR.
56. The antibody according to any of the previous embodiments, wherein said antibody binds human C5aR but not murine C5aR.
57. The antibody according to any of the previous embodiments, wherein said antibody binds the 2nd extracellular loop of human C5aR but not the 2nd extracellular loop of murine C5aR.
58. The antibody according to any of the previous embodiments wherein said antibody binds the 2nd extracellular loop of human C5aR in the native conformation only.
59. The antibody according to any of the previous embodiments wherein the antibody significantly inhibits or reduces binding of C5a to human C5aR.
60. The antibody according to any of the previous embodiments wherein the antibody is capable of displacing C5a in an SPA assay, with an IC50 below 10 nM or below 5 nM or preferably below 3 nM.
61. The antibody according to any of the previous embodiments wherein the antibody significantly inhibits migration of human neutrophils in vitro.
62. The antibody according to any of the previous embodiments, wherein the antibody reduces migration to less than 50%, less than 40%, less than 30%, less than 20%, less than 15%, or less than 10%, when measured after 30 minutes in the presence of 10 nM C5a compared to the level of migration observed after 30 minutes in the presence of 10 nM C5a and no antibody or wherein the IC50 in the same set up is below 2.5 µg/ml, such as below 2.5 µg/ml, such as below 1.5 µg/ml, such as below 1.2 µg/ml or even below 1.0 µg/ml.
63. The antibody according to any of the previous embodiments wherein the affinity of the antibody as measured by competition ligand binding assay on neutrophils is below 0.80 nM, such as below 0.50 nM or 0.35 nM.
64. The antibody according to any of the previous embodiments wherein the antibody neutralizes C5a induced neutrophil activation ex vivo with an IC50 as determined in a calcium-flux assay below 7.0 µg/ml, such as below 5.0 µg/ml, such as below 2.5 µg/ml.
65. The antibody according to any of the previous embodiments, wherein the antibody inhibits C5a induced neutrophil maturation ex vivo with
   a. an IC50 as determined in a CD11 b up-regulation assay below 3.5 µg/ml, such as below 2.5 µg/ml, such as below 1.5 µg/ml or even below 1.0 µg/m or
   b. an IC50 as determined in a CD62L down-regulation assay below 1.8 µg/ml, such as below 1.5 µg/ml, such as below 1.2 µg/ml or even below 1.0 µg/ml.
66. An antibody binding C5aR, wherein the Fc region has decreased affinity/reduced binding to one or more Fcγ receptors compared to IgG1, IgG2, IgG4 or IgG4/G2 Fc reference sequences as defined by SEQ ID NO 33, 34, 35 and 36, respectively.
67. The antibody according to any of the previous embodiments wherein the Fc region includes one or more point mutations compare to IgG1, IgG2, IgG4 or IgG4/G2 Fc reference sequences as defined by SEQ ID NO 33, 34, 35 and 36 respectively, reducing the affinity to one or more Fcγ receptors.
68. The antibody according to any of the previous embodiments wherein the antibody does not significantly induce phagocytosis of neutrophils in vitro.
69. The antibody according to any of the previous embodiments wherein the antibody does not significantly induce ADCC in vitro.
70. The antibody according to any of the previous embodiments wherein the antibody does not significantly induce CDC in vitro.
71. The antibody according to any of the previous embodiments wherein the Fc region is IgG1 (SEQ ID NO: 33), IgG2 (SEQ ID NO: 34), IgG2/4 (SEQ ID NO: 35), or IgG4 (SEQ ID NO: 36), with one or more of the following point mutations
   a. E233P
   b. L234A or V234A or F234L or F234V
   c. L235E or L235A
   d. G236R or G236A
   e. G237A
   f. N297Q
   g. L328R
   h. A330S
   i. P331S
72. The antibody according to any of the previous embodiments wherein the Fc region is IgG1 or an IgG1 mutant.
73. The antibody according to any of the previous embodiments wherein the Fc region is an IgG1 Fc mutant comprising 1 to 10 amino acid substitutions compared to the IgG1 Fc reference as defined in SEQ ID NO. 33.
74. The antibody according to any of the previous embodiments wherein the Fc region is an IgG1 Fc mutant comprising 1 to 8 amino acid substitutions in AA 231 to 240 wherein the IgG1 Fc reference sequence is as defined in SEQ ID NO. 33.
75. The antibody according to any of the previous embodiments wherein the Fc region is an IgG1 Fc mutant comprising 1 to 5 amino acid substitutions in AA 328 to 334 wherein the IgG1 Fc reference sequence is as defined in SEQ ID NO. 33.
76. The antibody according to any of the previous embodiments wherein the antibody Fc region is IgG1, with one or more of the following groups of point mutations
   a. N297Q and/or
   b. L234A and L235E and/or
   c. G236R and L328R and/or
   d. N297Q, L234A and L235E and/or
   e. N297Q, L234A, L235E and G237A and/or
   f. L234A, L235E, G237A, A330S and P331S
77. The antibody according to any of the previous embodiments 52-76, wherein said antibody is a full length antibody or an antibody fragment or a single chain antibody.
78. The antibody according to any of the previous embodiments, wherein said antibody is a monoclonal antibody.
79. The antibody according to any of the previous embodiments wherein said antibody is a human, mouse, rat, rabbit, pig or none human primate antibody.
80. The antibody according to any of the previous embodiments, wherein said antibody is a mouse or human antibody.
81. The antibody according to any of the previous embodiments, wherein said antibody is a human antibody or a humanized antibody.
82. The antibody according to any of the previous embodiments, wherein said antibody is a human antibody
83. An antibody according to any of the previous embodiments for treatment of an immunonological disease or disorder.
84. The antibody according to embodiment 83, wherein the disorder is an inflammatory disease.
85. The antibody according to embodiment 83, wherein the disorder is an acute or chronic inflammation.
86. The antibody according to embodiment 83, wherein the disorder is an auto-immune disease.
87. The antibody according to any of embodiments 83-86, wherein the antibody is administered intravenously or subcutaneous.
88. The antibody according to any of the previous embodiments 83-87, wherein the antibody is administered in doses from 0.010 mg/kg up to 6 mg/kg.
89. The antibody according to any of the previous embodiments 83-88 wherein the antibody is administered once weekly or every 2 weeks.
90. The antibody according to any of the previous embodiments 83-89 wherein the antibody is administered in combination with another drug.
91. The antibody according to any of the previous embodiments 83-90 wherein the disease or disorder is rheumatoid arthritis (RA), psoriatic arthritis, systemic lupus erythematosus (SLE), lupus nephritis, Inflammatory bowel disease (IBD), Crohn's disease (CD), ulcerative colitis (UC) or irritable bowel syndrome.
92. The antibody according to any of the previous embodiments 83-91 wherein the patient is being treated with another drug such as methotrexate.
93. A method for treating or preventing a disorder in a subject, the method comprising administering to a subject in need a therapeutic amount of an antibody according to any of the embodiments 1 to 82.
94. The method according to embodiment 93, wherein the disorder is an immunological disease or disorder.
95. The method according to embodiment 93 or 94, wherein the antibody the antibody is administered intravenously or subcutaneous.
96. The method according to any of the embodiments 93-95, wherein the antibody is administered in doses from 0.010 mg/kg up to 6 mg/kg.

97. The method according to any of the embodiments 93-96, wherein the antibody is administered once weekly or every 2 weeks.
98. The method according to any of the embodiments 93-97, wherein the antibody is administered in combination with at least one other drug.
99. The method according to any of the embodiments 93-98, wherein the disorder is an immunopathological disorder such as an autoimmune disease.
100. The method according to any of the embodiments 93-99, wherein the subject is patient suffering from rheumatoid arthritis (RA), psoriatic arthritis, systemic lupus erythematosus (SLE), lupus nephritis, Inflammatory bowel disease (IBD), Crohn's disease (CD), ulcerative colitis (UC) or irritable bowel syndrome.
101. The method according to any of the embodiments 93-101, wherein the patient is being treated with another drug.
102. A pharmaceutical composition comprising an antibody according to any of the embodiments 1 to 82 optionally in combination with a pharmaceutically acceptable carrier
103. The pharmaceutical composition according to embodiment 102, in the form of an aqueous formulation or a dry formulation that is reconstituted in water/an aqueous buffer prior to administration.
104. An isolated polynucleotide encoding a polypeptide sequence(s) of an antibody according to any of embodiments 1 to 82.
105. A host cell comprising one or more polynucleoptides according to embodiment 104.
106. A process for producing an antibody according to any of embodiments 1 to 82, comprising culturing a host cell according to embodiment 105 under conditions supporting expression of one or more polypeptide sequence(s) of said antibody.
107. The process according to embodiment 106, wherein the heavy chain and light chain are encoded by two separate open reading frames on one contiguous polynucleotide.
108. The process according to embodiment 106 or 107, further comprising recovering said antibody from the host cell culture.
109. Use of an antibody according to any of embodiments 1 to 82 for the manufacture of manufacturing of a medicament.
110. Use of an antibody according to any of embodiments 1 to 82 for manufacturing of a medicament for treatment of an immunonological disease or disorder such as rheumatoid arthritis (RA), psoriatic arthritis, systemic lupus erythematosus (SLE), lupus nephritis, Inflammatory bowel disease (IBD) or irritable bowel syndrome.

EXAMPLES

Example 1

Generation of Human Anti-hC5aR Antibodies

Immunization and Screening

In general, raising antibodies against GPCRs are difficult since soluble protein having the correct native protein conformation is very difficult if not possible to produce. Traditionally, cells over-expressing GPCRs have been used for immunization, but the resulting antibody responses tends to be very unspecific which makes it difficult to identify antibodies that have the desired profile i.e. being able to block ligand binding and GPCR signalling. Indeed, the inventors found it very challenging to develop human anti-hC5aR antibodies which could block C5a binding to C5aR, and a number of immunization strategies were applied before these antibodies were identified.

HumAb mice (Medarex) were immunized with L1.2-mouse cells (a mouse B-cell lymphoma line) with high expression of human C5aR (80,000 copies per cell) (Lee et al Nat. Biotechnol, 2006; 10:1279-1284) and splenocytes from immunized mice were used for cell fusions using standard procedures. Due to the lack of soluble hC5aR the supernatants could not be screened in a standard ELISA assay, and a cell based binding assay was therefore established. The obtained hybridoma supernatants were tested for binding to a transfected rat cell line (RBL) stably expressing a high number (~1,000,000 copies per cell) of native hC5aR by FACS analysis as described in WO2008/022390. In general the hybridoma supernatants were incubated with a mixture of un-transfected cells (labeled with CELL-TRACKER) and hC5aR-transfected cells, or neutrophils from hC5aR knock-out/knock-in (KOKI) mice (WO 2005/060739), and incubated with APC-conjugated F(ab')2 goat anti-human IgG (IgG-APC). Supernatants binding to hC5aR-transfected cells but not to un-transfected cells were identified, and the anti-hC5aR producing hybridomas were subcloned and tested for binding to human neutrophils and bone marrow derived neutrophils isolated from KOKI mice (data not shown). Anti-hC5aR antibodies were purified from hybridoma supernatants using protein A sepharose and standard protocols.

Example 2

Identification and Characterization of Anti-hC5aR Antibodies

As mentioned the process of obtaining human anti-hC5aR antibodies were problematic, and 32 fusions had to be performed before a hC5a/hC5aR blocking antibody was identified. From 35 fusions and screening of more than 100,000 hybridoma supernatants only 11 clones were identified that could block hC5a binding to hC5aR. The assays applied in the characterization of the antibodies are described in the following. The reference antibody (Ref. Ab Q) is described in WO2009/103113. In addition, further assays suited for determining affinity and functionality in a Calcium-flux assay and in CD11b upregulation is described in Example 7.

Displacement Assay

A Scintillation Proximity Assay (SPA) was applied in order to determine the potency of the anti-hC5aR antibodies to displace hC5a binding to hC5aR. A detailed description of the SPA is provided in U.S. Pat. No. 4,568,649 and protocols provided by the manufacturer (Amersham Biosciences). Briefly, receptor-carrying membrane fragments purified from RBL-hC5aR cells bind to scintillating micro particles coated with wheat germ agglutinin (WGA). After addition of radio-labelled hC5a ($^{125}$I) tracer, binding to the receptors will result in emission of light from the particles. Specific for the SPA-principle, only radio isotope and particles in immediate proximity of each other will emit light. I.e. only radio-labelled hC5a bound to a receptor is close enough to a WGA-particle to produce light. The amount of light emitted is thus an expression of the amount of receptor-bound $^{125}$I-hC5a. The assay is a competition assay, in which anti-hC5aR/unlabelled hC5a competes with the tracer on binding to the receptors. In the assay, a fixed amount of $^{125}$I-labelled C5a is added to WGA-particles and C5aR receptors resulting in emission of a certain amount of light measured as counts per minute (cpm). If unlabelled C5a or anti-C5aR is added, binding hereof to the receptors will cause a lower cpm due to displacement of $^{125}$I C5a. The % displacement was calculated as follows:

$$\frac{S - S\max}{So - S\max} \cdot 100\%$$

S: Sample $S_{max}$: Non specific binding. Measured by adding unlabelled hC5a in an amount sufficient to supersede the specifically bound $^{125}$I-hC5a.

$S_0$: Maximum binding. No unlabelled hC5a is added. The IC50 value is defined as the concentration which displaces 50% of C5a. The cpm was kept constant between experiments hence the IC50 values are relative as the tracer decades over time. The potency (IC50) of the human anti-hC5aR antibodies to displace $^{125}$I-hC5a was determined and the data is provided in table 1.

Neutrophil Migration (Chemotaxis) Assay

The potency of the antibodies to inhibit hC5a (or mC5a)-dependent neutrophil migration was analysed in a Boyden chamber. Neutrophils isolated from human or animal blood were stained with calcein and added to the upper compartment in the Boyden chamber and mixed with the antibodies. hC5a or mC5a is applied to the lower compartment in the Boyden chamber and acting as chemoattractant for the neutrophils. The ability of neutrophils to migrate to the lower chamber is determined by counting the number of calcein-stained neutrophils passing through a 3 or 5 μm FLUOROBLOK membrane.

Human PMNs (PolyMorphoNuclear leukocytes; granulocytes) were obtained from human blood samples drawn into vials containing EDTA. The blood cells were separated by centrifugation of blood (4 parts) through a Ficoll-Paque PLUS (GE Health Care) gradient (3 parts) for 30 min (400×g) at room temperature. The PMN-containing layer was suspended in PBS (phosphate buffered saline) containing dextran-500 (Sigma) for 1 h to remove contaminating erythrocytes. The supernatant was centrifuged for 5 min (250×g) at room temperature and remaining erythrocytes were osmotically lysed using 0.2% NaCl for 55 s. The solution was made isotonic by 1.2% NaCl+PBS and centrifuged at 250×g for 5 min, before the osmotic lysis was repeated. After centrifugation the PMNs were resuspended in reaction mixture (RM): HBSS (cat no 14175 Gibco) contains NaCl 137 mM, KCl 5.3 mM, $Na_2HPO_4$ 0.33 mM, $NaHCO_3$ 4 mM, $KH_2PO_4$ 0.44 mM, Glucose 5 mM; supplemented with $MgSO_4.7H_2O$ 0.4 mM, $MgCl_2$, 0.5 mM, $CaCl_2$ 0.5 mM, HEPES 20 mM. Cell density was determined by NUCLEOCOUNTER (Chemometec). The PMN suspension contained >95% neutrophils as evaluated by microscopy of Giemsa-stained samples.

Loading PMNs: Calcein, AM, (Fluka) was dissolved in DMSO (Dimethyl sulphoxide) and diluted 1000× in RM with cells (2×10$^6$ cells per ml) to yield a concentration of 10 μM. The suspension was incubated for 30 min in incubator at 37° C. and then washed 3 times with RM to remove excess Calcein. Finally the cells were resuspended in RM (4×10$^6$ cells/ml), Migration was evaluated by the Boyden chamber technique using FLUOROBLOK® 3 μm pore size 96-well (cat. No. 351161.BD Falcon (VWR)). The upper chamber i.e. the inserts containing FLUOROBLOK membrane was coated with human fibrinogen (cat no F3879-1G, Sigma) in 1 mg/ml PBS at 37° C. for 2 hrs. After washing the membranes were blocked with a solution containing 2% bovine serum albumin (BSA), in PBS. After another wash using RM, 10$^5$ Calcein-loaded PMNs with or without the hC5aR-antibodies were added to each well and placed in the receiver plate (lower chamber) which contained the control solution or the chemoattractant hC5a (Sigma, C5788). Each group comprised of at least 6 wells. Thereafter the plate was measured at 485/538 nm, 37° C. every 5 min for 60 min in a plate reader (SPECTRAMAX, Molecular devices, or FLUOROSCAN, Thermo Labsystems.). The value at 30 min in relative fluorescence units was used as a measure of migration.

Curve fitting. The ability of antibodies to inhibit migration was expressed by 1050 as determined using GRAPHPAD PRISM 5 (GRAPHPAD Software, Inc.)

Table 1 includes the data from the displacement assay and the chemotaxis assay which tested the ability of 10 μg/ml human mAbs to inhibit hC5a-dependent (10 nM) migration of human neutrophils. The value obtained in absence of antibody was set to 100. Data was compiled from 3 donors. Average values are included in table 1. The three mAbs 32F3A6, 35F12A2 and 35F32A3 showed the strongest potency in both assays, which was equal to or slightly higher than the potency of a control antibody Ref. Ab is Q described in WO2009/103113.

TABLE 1

Functional characteristics of anti-hC5aR antibodies.

| Ab | hC5a displacement (SPA) IC50 (nM) | Migration of human neutrophils (In % compared to migration in the absence of antibody). |
|---|---|---|
| 35F32A3 | 0.95 | 11 |
| 32F3A6 | 1.90 | 2 |
| 35F12A2 | 2.04 | 19 |
| 35F24A3 | 2.97 | 30 |
| 35F16A2 | 3.90 | 22 |
| 35F3A1 | 10.7 | 38 |
| 35F34A1 | 18.6 | 35 |
| 35F6A1 | 22.9 | ND |
| 34F12A5 | 32.1 | >70 |
| 35F33A1 | 33.4 | >70 |
| 34F12A3 | 46.6 | >70 |
| hC5a | 4.1 | 100 |
| Ref. Ab Q | 3.7 | 20-21 |

Characterization of Anti-hC5aR mAb CDR Sequences

The variable regions from the anti-hC5aR Abs 35F32A3, 32F3A6, 35F12A2 and 35F24A3 were cloned recombinantly and the nucleotide and amino acid sequences were characterized using standard methods. The amino acid sequences are included in FIG. 1 and the accompanying sequence list.

Characterization of Binding Specificity

Human-mouse C5aR chimeric constructs were used to determine the binding region of C5aR. The chimeric receptors were transiently expressed in HEK cells and binding of the individual antibodies was determined by FACS as previously described in WO 2008/022390 except for the change of cell line. Binding of 32F3A6, 35F32A3 and 35F12A2 were dependent on human sequence of the extracelluar loop 2, whereas the human N-terminal was dispensable (FIG. 2).

Example 3

Generation of Fc Variants

The four human IgG subclasses (IgG1, IgG2, IgG3 and IgG4) share more than 95% homology in the Fc regions, but show major differences in the hinge region. The Fc region mediates effector functions, such as Antibody-Dependent Cell-Mediated Cytotoxicity (ADCC) and Complement Dependent Cytotoxicity (CDC). In ADCC, the Fc region of an antibody binds to activating Fc receptors (FcγRs) on the surface of immune effector cells such as natural killer cells and monocytes, leading to phagocytosis or lysis of the targeted cells. In CDC, the Fc region binds to complement at a site different from the FcγR-binding sites, and the antibodies kill the targeted cells by triggering the complement cascade at the cell surface. The various IgG isoforms exert different levels of effector functions increasing in the order IgG4<IgG2<IgG1<IgG3. A number of IgG Fc variants, which all comprise the variable region of Ref Ab Q, were generated by site-directed mutagenesis using Quick-Change® Site-Directed Mutagenesis Kit (Cat no. 200518, Stratagene) and characterized as described in example 4.

seconds, and a dissociation time of 300 seconds. The other FcγRs were injected with a flow rate of 50 μl/min, a contact time of 30 seconds, and a dissociation time of 120 seconds. Chip surfaces were regenerated with a solution containing 10 mM NaOH and 500 mM NaCl. The affinities (Kd values) are listed in table 2A.

TABLE 2A

Summary of the results obtained from analysis of the Fc variants affinity towards FcγRs (Kd in M).

| IgG | Antibody Fc region | FcγRI | FcγRIIA (131R) | FcγRIIA (131H) | FcγRIIB | FcγRIII (158F) | FcγRIII (158V) |
|---|---|---|---|---|---|---|---|
| IgG1 | L234A, L235E, G237A, A330S and P331S | — | — | — | 2.10E−6 | — | — |
| | N297Q, L234A, L235E, G237A | — | — | — | — | — | — |
| | N297Q, L234A, L235E | — | — | — | — | — | — |
| | G236R, L328R | — | — | — | — | — | — |
| | L234A, L235E | nd$^a$ | nd$^a$ | nd$^a$ | nd$^a$ | nd$^a$ | 0.96E−6 |
| | N297Q | 0.36E−6 | — | — | — | — | — |
| | IgG1 reference | 6.64E−10 | 0.95E−6 | 0.64E−6 | 0.42E−6 | 0.33E−6 | 0.07E−6 |
| IgG2 | N297Q | — | nd$^a$ | nd$^a$ | — | — | — |
| | IgG2 reference | — | 2.79E−6 | 0.22E−6 | 1.54E−6 | — | 1.50E−6 |
| IgG2/4 $^{(1)}$ | N297Q | — | — | — | — | — | — |
| | V234A, G236A | — | — | — | 5.34E−6 | — | — |
| | IgG2/IgG4 reference | — | nd$^a$ | 1.03E−6 | 1.83E−6 | — | — |
| IgG4$^{(2)}$ | N297Q, F234L, L235A | nd$^a$ | — | — | — | — | — |
| | N297Q, E233P, F234V, L235A | — | — | — | — | — | — |
| | E233P, F234V, L235A | 0.38E−6 | — | — | nd$^a$ | — | nd$^a$ |
| | N297Q | 0.13E−6 | — | — | — | — | — |
| | IgG4$^{(2)}$ reference | 2.71E−9 | 0.80E−6 | 3.52E−6 | 1.08E−6 | — | nd$^a$ |

(— = no binding; 0 = no change in binding; nd$^a$ = Kd not calculated due to too weak binding).
$^{(1)}$ a IgG2/IgG4 Fc variant comprising the CH1 and lower hinge region of IgG2, and the remaining CH2—CH3 of IgG4;
$^{(2)}$IgG4 mutant including the point mutation S228P.

Example 4

Characterization of Effector Functions of Fc Variants

Binding Affinity of Fc Variants to FcgRs

The affinity of the Fc variants towards FcγRs was determined by surface plasmon resonance (SPR) measurements which were performed on a BIAcore T100 instrument using a CM5 sensor chip (GE). The Fc variants were immobilized onto flow cells using amine-coupling chemistry. For kinetic SPR measuring the affinity of FcγR to the Fc variants, His-FcγRs were used as analytes and were injected into flow cells in HBS-EP buffer. The high affinity receptor FcγRI was injected with a flow rate of 40 μl/min, a contact time of 180

Phagocytosis Assay

In order to identify Fc variants with reduced or abolished capabilities to mediate phagocytosis of neutrophils an in vitro phagocytosis assay was established. The phagocytosis assay described in the following involves labelling of human neutrophils isolated from peripheral human blood (the target cell for phagocytosis) with a fluorescent dye, CMFDA, and adding them to a culture of human monocytes, also isolated from human peripheral blood. The CMFDA-labelled neutrophils are pre-coated with test mAbs (or PBS), and after incubation with the human monocytes, the number of CD14/CMFDA double positive monocytes is determined by FACS. The results from various Fc variants are presented in table 2B.

All antibodies tested include the variable regions of the Q antibody described in WO2009/103113 and used as Ref Ab above.

Both monocytes and macrophages were found to be capable of mediating antibody dependent phagocytosis of neutrophils, and phagocytosis assays using both cell types were established. Results were qualitatively similar in both assays, but since the macrophage assay was more variable, the analysis was primarily performed using monocytes.

Preparation of Human Monocytes

Human monocytes and lymphocytes were isolated from peripheral venous blood collected from healthy human volunteers in tubes containing EDTA as anti-coagulant (K2E, BD Biosciences, Cat. No. 367525) using percoll gradient centrifugation. 100 ml blood generally gave ~8-20×10$^7$ Peripheral Blood Mononuclear Cells (PBMCs). At least 3 volumes of dPBS were added to the isolated cells that were then centrifuged at 100×g for 10 min. at room temperature (RT). After discarding the supernatant the lymphocyte/monocyte layer was resuspended in the same volume of a 50:50 mix of dPBS:Culture Medium as the previous step and centrifuged again at 100×g for 10 min. at RT. The supernatant was discarded and lymphocyte/monocyte layer resuspended at 1-2×10⁶ cells/ml in Culture Medium. The resuspended cells were plated in 6-well tissue culture plates (Corning, Costar Cat. No. 3516) at 2 ml/well with 4×10⁶ cells/well and incubated for 2 hours at 37° C. in 5% $CO_2$. Non-adherent cells (lymphocytes and dead cells) were removed by aspiration and the adhered cells (monocytes) washed four times in 1 ml Culture Medium (RPMI 1640 (Invitrogen-GIBCO, Cat. No. 11875)+10% FCS (Invitrogen-GIBCO, Cat. No. 16000) heat inactivated at 56° C. for 30 min+25 mM Hepes (Invitrogen-GIBCO, Cat. No. 15630)+1% Pen/Strep (Invitrogen-GIBCO, Cat. No. 15070)) with gentle swirling before aspiration of the wash medium. After washing the blood-derived monocytes 1 ml fresh Culture Medium was added to each well. Cells were scraped from one well and suspended in Culture Medium in order to estimate the number of monocytes per well.

Preparation of Human Neutrophils

Human neutrophils were isolated from peripheral venous blood collected from healthy volunteers) using percoll gradient centrifugation and stained with CellTracker™ Green (5-chloromethylfluorescein diacetate, CMFDA). 100 ml blood generally gave ~10-20×10⁷ neutrophils. Staining was performed by dissolving CellTracker™ Green CMFDA in DMSO to 10 mM final concentration. Neutrophils were resuspended at 1×10⁷ cells/ml in dPBS and CMFDA was added to a final concentration of 2 µM. Cells and dye were incubated for 15 min at 37° C. Excess dye was removed by washing the cells 3 times with 10 ml dPBS (by centrifugation at 300×g for 5 min at RT). A cell count was performed after the last wash step. CMFDA-labelled-neutrophils were resuspended at 2×10⁶ cells/ml in dPBS and incubated with antibody (final concentration 0.001, 0.01, 0.1, 1, 10 or 100 µg/ml) or PBS (for no antibody control). In some assays (as indicated) the neutrophil+Ab incubation step also contained 4 mg/ml human IgG. Cells plus antibody were incubated for 30 min at 37° C. Neutrophils were washed twice with dPBS after centrifugation at 300×g for 5 minutes at RT and resuspended in Culture Medium at 1×10⁷ cells/ml.

FACS Analysis

CMFDA-labelled neutrophils, pre-coated with antibody (prepared as described above) were added to monocytes (as described above) at the desired concentration in 1 ml Culture Medium. The total volume in each well of the 6-well plate was 2 ml. In some assays (as indicated) the culture medium also contained 4 mg/ml human IgG. A ratio of 5:1 (neutrophils:monocytes) was generally used. If the number of adherent monocytes was less than 4×10⁵ per well then 2×10⁶ neutrophils was added (i.e. the neutrophil:monocyte ratio exceeded 5:1). If the number of monocytes exceeded 4×10⁵ per well then five times that number of neutrophils was added to keep the neutrophil:monocyte ratio at 5:1. Cultures were incubated for 1 hour at 37° C. in a 5% $CO_2$ incubator After incubation the medium was aspirated to remove non-adherent and non-ingested neutrophils. Adherent monocytes were washed (with gentle swirling) three times with 1 ml/well Culture Medium. Monocytes were collected in 15 ml tubes by scraping the cells in Culture Medium from wells with Cell Scrapers (Corning, Cat. No. CP3010). Cells were centrifuged at 300×g for 5 min at RT and supernatant removed. The cell pellet was resuspended in 160 µl 1% (w/v) paraformaldehyde in PBS to fix prior to FACS.

Samples were analysed on a FACSCALIBUR flow cytometer (BD Biosciences). Neutrophils labelled with CMFDA were identified and measured in FL-1 (Fluorescence channel 1) using Fluorescein isothiocyanate (FITC), and monocytes identified by staining a monocyte only sample with Phycoerythrin labelled anti-CD14, which was measured in FL-2 (Fluorescence channel 2). A monocyte gate was defined using the FSC (Forward scatter) vs. SSC (Side scatter) profile of the monocyte only sample and widened (along FSC and SSC axes) so as to include monocytes whose size had increased during incubation. This gate excluded the region of the FSC vs. SSC profile containing neutrophils as defined in the FSC vs. SSC profile in a neutrophil only sample. The extent of phagocytosis was calculated to be the percentage of FL-1$^{+ve}$ monocytes in the total monocyte gate.

The background level of non-specific phagocytosis was the percentage of FL-1$^{+ve}$ monocytes in a sample containing CMFDA-labelled neutrophils not coated with antibody ("No Ab" sample). Background was subtracted from each sample with Ab before the data (% FL-1+ve Monocytes vs. Ab concentration) was entered into a Prism (v4.0c, GRAPH-PAD Software Inc) for graphing. Data was subject to non-linear regression using the sigmoidal dose-response (variable slope) i.e. 4-parameter logistic equation in order to determine EC50 values where appropriate.

The data are presented in Table 2B. "−" represents no detectable phagocytosis and "+" to "++++" represents low to high level of phagocytosis as measured in the assays.

ADCC (Antibody Dependent Cellular Cytotoxicity) and CDC (Complement Dependent Cytotoxicity) Assays The following in vitro assays were established in order to test the ability of the Fc variants to mediate cell depletion via ADCC or CDC dependent mechanisms.

Target Cells

In these assays the target cells were hC5aR expressing Ramos clone E2 or human neutrophils. The hC5aR expressing Ramos clone E2 was developed by stably transfecting Ramos clone E2 cells with a mammalian expression vector encoding hC5aR using standard procedures. The resulting cell line expresses high levels of human C5aR (5-7 times higher than on human neutrophils) and CD20. Human neutrophils were obtained as described above in relation to the phagocytosis assay.

Target cells were stained with the fluorescent cell membrane dye, PKH-26. The required number of target cells (5×10⁴/sample/well×4) were diluted to 15 ml in dPBS and centrifuged at 1,200 rpm for 5 min at RT. Cells were then resuspended in 2 µM PKH-26 (100 µl solution for every 1×10⁶ target cells). Labelling was allowed to proceed at room temperature for exactly 3 min before an equal volume of heat-inactivated FCS (or heat-inactivated human serum (Millipore)) was added to stop the labelling reaction. After exactly 1 min RPMI was added to a total volume of 15 ml. Cells were centrifuged as above and resuspended at 2×10⁶ cells/ml in Assay medium. For coating with antibody aliquots (25 µl i.e. 5×10⁴) of PKH-26 labelled target cells were dispensed into wells of a sterile U-bottom 96-well plate containing 25 µl of 200 µg/ml antibody diluted in Assay Medium (end concentration 100 µg/ml) and incubated at 37° C. in 5% $CO_2$ for 30 min.

Effector Cells

The effector cells were monocyte-depleted PMBCs from healthy donors. PMBC's were obtained as described above. The resuspended cells (lymphocyte/monocytes) were plated in E-well tissue culture plates (Corning) at 2 ml/well with ~4×10⁶ cells/well or T75 flasks (Corning) at 20 mL per flask and incubated for 2 hours at 37° C. in 5% $CO_2$. The non-adherent cells (including lymphocytes and NK cells) were removed by aspiration and centrifuged at 100×g for 10 min. at RT. Cells were resuspended in 20 mL medium containing 100 ng/ml of recombinant human IL-2 to increase the number of lymphocytes and natural killer cells. The cells were incubated overnight at 37° in 5% $CO_2$. The following day the cells were centrifuged at 1,400 rpm for 10 min at RT then resuspended in Assay medium at $2.5 \times 10^7$ cells/ml for use as effector cells in the ADCC assay.

ADCC Assay

Following labelling of target cells with PKH-26 and coating with antibody 100 μl effector cells or 100 μl Assay medium (control, target cell only) was added directly to 50 μl target cells. Samples were incubated for a further 3 hrs at 37° C. in 5% $CO_2$. The samples were transferred to 1.2 ml microtiter FACS tubes containing 10 μl 10 μM To-Pro-3 viability dye (TP-3) for a final concentration of ~625 nM and samples were analysed by FACS. On a FSC vs. SSC plot all cells excluding debris were gated. The gated cells were analysed on the FL-2 vs. FSC and the FL-2 positive cells (i.e. PKH-26 labelled target cells) were gated. FACS data was analysed using FLOWJO software (Tree Star, Inc. v6.3.4).

Specific ADCC was calculated by subtracting the average % $TP3^{+ve}$ 'Targets Only' (A) from the average % $TP3^{+ve}$ Targets+Effectors' (B) of corresponding samples after subtracting the average % $TP3^{+ve}$ 'No Ab Targets Only' (C) and average % $TP3^{+ve}$ 'No Ab Targets+Effectors' (D) respectively; i.e.

$$\text{Specific } ADCC = (B-D)-(A-C) \text{ or } =(B-A)-(D-C) \quad \text{Equation 1}$$

The results presented in table 2B, were obtained using monocyte-depleted, IL-2-stimulated human PBMCs, predominantly NK cells but including B-cells, T-cells and dendritic cells, as the effector cell population. The target cells were a transfected cell line Ramos E2 expressing both hC5aR and CD20 enabling use of the anti-CD20 antibody rituximab as the positive control. The results range from "+++" which is indicative for a Fc variant inducing ADCC with equal potency as Rituximab, "+/−" which is indicative for a Fc variant for which a high degree of donor variation was observed and "−" which is indicative for a Fc variant for which no significant induction of ADCC was detected. An Fc variant mediating increased ADCC (IgG1_S239D, 1332E) (Chu S Y, Vostiar I, Karki S et al; Mol Immunol, 2008, 45(15):3926-3933) was included as a positive control for the assay.

CDC Assay

The Fc variants were also analysed for their potency to induce CDC. The experimental set up was essentially as described for the ADCC assay except that effector cells were replaced with human serum.

Targets cells, such as Ramos E2 cells ($2 \times 10^6$ cells/ml) in medium with 3% Rabbit Complement Sera were mixed with an equal volume of 2× antibody solution (200 μg/ml), containing 3% Rabbit Complement Sera in a 96-well U-bottom tissue culture plate. A duplicate set of wells contained 25 μl Ramos E2 cells ($2 \times 10^6$ cells/ml) mixed with 25 μl 2× antibody solution (200 μg/ml) in medium without complement. A set of 3 wells contained 25 μl Ramos E2 cells ($2 \times 10^6$ cells/ml) plus 25 μl assay medium ('no Ab' samples) in 3% Rabbit Complement Sera. Another set of 3 wells contained 25 μl Ramos E2 cells ($2 \times 10^6$ cells/ml) plus 25 μl assay medium ('no Ab' samples) without complement. Before incubation, 100 μl assay medium, with or without 3% Rabbit Complement Sera as appropriate, was added to each well. Samples were incubated for 3 hrs at 37° C. in 5% $CO_2$.

Determination of Target Cell Viability

The fluorescent viability dye To-Pro-3 (Molecular Probes), was added to each sample immediately before analysis by flow cytometry. The final concentration of To-Pro-3 in each tube was ~62.5 nM. To-Pro-3 positive (TP3+) cells were defined as being non-viable or lysed.

Flow Cytometry & Data Analysis

Samples were analysed on a FACSCALIBUR (BD Biosciences) and the data acquired was analysed using FLOWJO software (v6.3.4, TreeStar Inc.). In the FSC vs. SSC scatter plot, gating on all cells excluding debris, 5,000 target cell events were collected for each sample. A histogram of the gated target cells in the FL-4 channel was created which showed the level of To-Pro-3 uptake by cells. The number of TP3+ cells (i.e. non-viable cells) in each sample was determined—these were defined as cells to the right side of the main peak—and this number was expressed as a percentage of total target cells in the sample.

Samples, assayed in triplicate, could be classified into one of 4 categories, A, B, C and D as shown in Category overview below.

Category Overview

| Categories of samples analysed | | |
|---|---|---|
| Target cells incubated with: | 100 μg/ml Ab | No Ab |
| No Complement | A | B |
| Rabbit complement sera | C | D |

For each sample that contained antibody, reactions were carried out with or without complement. Samples containing antibody without complement gave the level of antibody specific background lysis. Samples in categories B & D gave non-specific background lysis in absence of either antibody or both antibody and complement.

The percentage of TP3+ non-viable target cells (% lysis) was calculated for each sample with 3% complement and for each sample without complement. For each antibody and 'no Ab' control, data from the triplicate samples was averaged.

To calculate the Specific CDC activity for each antibody, antibody-specific lysis in absence of complement (average % lysis in 'A' samples) was subtracted from the % lysis of Ab sample with complement ($C_{1/2/3}$' samples) before subtracting non-specific background lysis. Non-specific background lysis was lysis in 'no Ab' samples with complement (average % lysis in 'D' samples) less lysis in 'no Ab' samples without complement (average % lysis in 'B' samples). Fc variant mediating increased CDC (IgG1_S254W) (WO08030564) was included as a positive control for the assay.

$$\text{Specific } CDC \text{ (\% lysis)}=(C-A)-(D-B)[\text{or}=(C-D)-(A-B)] \quad \text{Equation 2}$$

Statistical analysis was performed in GRAPHPAD Prism (v4.0) to determine whether differences between any of the groups were significant. Specific CDC activity of each sample from all 4 assays was entered into a spreadsheet according to antibody used. The groups were compared using a parametric test: one-way analysis of variance (ANOVA) followed by Tukey's multiple comparison post test.

The results are included in table 2B. The results range from "+++" which is indicative for a Fc variant inducing CDC with equal potency as the IgG1 S254W mutant. "+/−" which is indicative for a Fc variant for which a high degree of variation was observed and "−" which is indicative for a Fc variant for which no significant induction of CDC was detected.

TABLE 2B

Activity of Fc variants in cell based effector function assays.

| IgG | Antibody Fc region | Phagocytosis | ADCC | CDC |
|---|---|---|---|---|
| IgG1 | L234A_L235E_G237A_A330S_P331S | − | −/+ | − |
|  | N297Q_L234A_L235E_G237A | − | ++ | − |
|  | N297Q_L234A_L235E | − | ++ | − |
|  | G236R_L328R | − | +++ | − |
|  | L234A_L235E | + | +++ | − |
|  | N297Q | ++ | + | − |
|  | IgG1 reference | +++ | +++ | − |
|  | S239D_I332E | +++ | +++ | − |
|  | S254W | ++++ | +++ | +++ |
| IgG2 | N297Q | − | ++ | − |
|  | IgG2 reference | ++ | − | − |
| IgG2/4[1] | N297Q | − | − | − |
|  | V234A_G236A | − | − | − |
|  | IgG2/IgG4 reference | + | − | − |
| IgG4 (S228P)[2] | N297Q_F234L_L235A | − | −/+ | − |
|  | N297Q_E233P_F234V_L235A | − | − | − |
|  | E233P_F234V_L235A | + | − | − |
|  | N297Q | + | −/+ | − |
|  | L235A | ++ | + | −/+ |
|  | F234L_L235A | ++ | + | /+ |
|  | IgG4 reference | +++ | + | /+ |

Summary of the results obtained from analysis of the Fc variants in phagocytosis, ADCC and CDC assays. (− = no effector function; + = effector function).
[1]a IgG2/IgG4 Fc variant comprising the CH1 and lower hinge region of IgG2, and the remaining CH2—CH3 of IgG4;
[2]S228P mutation introduced in IgG4 Fc region in order to eliminate the formation of half-antibodies.

Example 5

Characterization of Potency of Anti-hC5aR Antibody Fc Variants

In order to test if mutations in the Fc region affect the potency of the antibodies to inhibit hC5a binding to hC5aR and hC5a-mediated neutrophil migration, respectively, the different Fc variants were tested in the displacement and migration assays described above. The Neutrophil Migration Assay was performed as described above except that the PMN's used were mouse PMNs isolated from hC5aR-KO/KI mice (mC5a-receptor knock-out/human C5aR knock-in, WO 2005 060739). The cells were obtained as follows. Bone marrow PMNs were isolated from femurs and tibias of two hC5aR-KO/KI mice. Marrow cells were flushed from the bones using PBS before the cell suspension was filtered through a Cell Strainer (BD Falcon, 352350; 70 micron nylon mesh) into a 50 ml tube and centrifuged (10 min, 1600 rpm). Cells were resuspended in medium and carefully layered on top of 3 ml Ficoll-Paque PLUS (GE Healthcare) in a sterile 15 ml tube. After centrifugation for 20 minutes at 600×g at room temperature, the neutrophil/erythrocyte pellet is isolated. The erythrocytes are lysed using Lysing Buffer (Sigma, R7757; 8.3 g/L ammonium chloride in 10 mM Tris-HCl pH 7.5) for 1 min. After two rounds of centrifugation and washing the cell pellet is resuspended in Reaction mixture. The suspension contained >95% neutrophils as evaluated by microscopy of Giemsa-stained samples. The variable region of the antibodies tested was identical to the variable region of Ref. Ab Q. Data are provided in table 3.

A significant difference in the potency to inhibit hC5a binding to hC5aR, was observed for the Fc variants in the SPA analysis (table 3, column 1). An IgG1 version of the Ref. Ab Q was analysed together with additional IgG Fc variants, and the data showed that IgG1 Fc variants in general inhibited hC5a binding more potently than both the IgG4 and IgG2/IgG4 Fc variants. A F(ab')$_2$ fragment of Ref. Ab Q was also included in the analysis and found to inhibit hC5a binding to the same extent as full length Ref. Ab Q (IgG4). These findings indicated that the hinge region is important for the ability of the antibodies to inhibit hC5a binding and this notion was supported by the fact that F(ab')$_2$ fragments were able to inhibit neutrophil migration to the same extent as Ref. Ab Q (Table 3). Also the IgG1 variants were found to be more potent in inhibiting neutrophil migration than IgGs comprising IgG2 or IgG4 hinge regions (Table 3, column 2).

The higher potency of IgG1 versions of Ref. Ab over the IgG4 versions could relate to increased avidity due to increased flexibility of the IgG hinge region. To investigate this, the binding of IgG1 and IgG4 versions of the Ref. Ab to human neutrophils was analysed by FACS. The data demonstrated that the IgG1 version bound to the neutrophils with higher avidity than the IgG4 version. Data not shown.

Taken together, these findings supports that increased flexibility in the IgG1 hinge regions contribute to increased binding to hC5aR, which leads to increased potency.

TABLE 3

Effect of Fc variants on hC5a binding (SPA) and neutrophil migration towards hC5a.
(+ = low activity, ++ = medium activity, +++/+ high).

| Antibody Fc region | hC5a displacement (SPA) | Inhibition of migration of human neutrophils |
|---|---|---|
| IgG4 | ++ | ++ |
| IgG1 | +++ | ND |
| IgG1(L234A_L235E_G237A_A330S_P331S) | +++ | +++ |
| IgG1 (S239D, I332E) | +++ | ++++ |
| IgG2/4 | + | ND |
| IgG2/4 (V234A, G236A) | + | + |
| Ref. Ab Q as F(ab)$_2$ | ++ | ++ |

Example 6

Generation and Characterization of "Fully" Human Anti-hC5aR Antibodies

From the analyses described in Example 2, antibody 32F3A6 was selected for further studies. During the recombinant cloning of this antibody, seven mutations in the VH framework region that differed from human germline sequences were identified, while no framework mutations were found in the LC (FIG. 3). The mutations were found by aligning the VH and VL sequences from 32F3A6 to all available human germline sequences.

In order to make the antibody even further human-like the seven point mutations in the VH region of 32F3A6 were mutated back to the human germline residues, and grafted onto the IgG1 Fc region comprising the five mutations L234A_L235E_G237A_A330S_P331S which were shown to abolish induction of phagocytosis, ADCC and CDC as described above. The compound is referred to as 32F3A6 GL.

The potency of the back-mutated antibody was compared to the original antibody and no difference was observed in the potency to inhibit hC5a binding to hC5aR (assayed in SPA) or in the potency to inhibit hC5a-mediated neutrophil migration between 32F3A6 or 32F3A6 GL (data not shown).

The ability of the fully human antibodies described above to induce neutrophil phagocytosis, ADCC or CDC were evaluated as described in example 4 and the results are summarized in table 4.

The results relating to the specific ADCC included in table 4 were obtained using monocyte-depleted human PBMCs as the effector cell, and human neutrophils as the target cell.

TABLE 4

Fc-mediated cellular effector functions of anti-C5aR antibodies.
"−" represents no detectable effector function
and "+" to "+++" represents low to high level of effector functions as measured in the assays described in example 4. ND (Not determined).

| Compound | | Phagocytosis | Specific ADCC | Specific CDC |
|---|---|---|---|---|
| PBS as control | | − | ND | − |
| | Variable region | Fc region | | |
| 3G12 (irrelevant antigen) | | IgG1 | − | + | − |
| 32F3A6 GL | | IgG1AEASS | − | + | − |
| 32F3A6 GL | | IgG1 | + | +++ | ND |
| Sigma | | IgG4 | ND | + | ND |

As previously observed the 5 point mutations in the Fc region of IgG1 abolish phagocytosis, ADCC and CDC compared to wild type IgG1 Fc region.

Example 7

Further Characterization of Human Anti-hC5aR Antibody (32F3A6 GL)

To further elucidate the functionality of the identified antibodies and to determine affinity and potency, additional assays were performed using one of the anti-C5aR antibodies in comparison with Ref AB Q. The affinity was determined by competition ligand binding assay on human neutrophils. This functionality is referred to as affinity of the antibody as measured by competition ligand binding assay, but could also be considered measurement of the avidity of the interaction. The ex-vivo assays measures the ability of the antibodies to neutralize C5a mediated actions in in-vitro setting. The potency assays measured the neutralization of C5a-induced Ca-flux, CD11b receptor up-regulation and CD62L down-regulation, respectively, on human neutrophils. The data obtained for 32F3A6GL are given in Table 5.

Affinity Measurements
Isolation of Neutrophils from Fresh Human Blood
Blood was diluted in 1:1 with PBS+2% FBS and layered on Ficoll-Paque PLUS (GE Healthcare #17-1440-03) at a ratio of 3 parts Ficoll and 4 parts blood (15 ml Ficoll and 20 ml blood in a 50 ml tube) and subsequently stratified by centrifugation at 400×g for 30 minutes at RT. By aspiration the intermediate PBMC band was gently removed. The granulocytes stratified on the packed red cells were aspirated with a plastic Pasteur pipette. The granulocytes and red cells were transferred and pelleted in a new 50 ml tube. The pellet was diluted to 40 ml with 1×PBS and 10 ml of a 4% DEXTRAN 500 (sigma, 31392) solution in PBS (rate 1:5) was added and mixed gently by inversion. After 20-30 min. the granulocyte rich supernatant obtained was transferred to a new tube and spun down at 250×g for 5 min at RT. The contaminating red cells were removed with osmotic lysis by resuspending the cell pellet in 7.5 ml of 0.2% NaCl and gently mixing for 55-60 seconds. Subsequently 17.5 ml of 1.2% NaCl was added and then diluted to 50 ml with PBS and spun down at 250×g for 5 min. This step was repeated once. The cell pellets were subsequently resuspended in 1 ml reaction mixture (dPBS/RPMI). The viability and cell count was monitored using NUCLEOCOUNTER®.

Competition Ligand Binding Assay on Neutrophils.
Human neutrophils were purified, washed and resuspended in binding buffer (50 mM HEPES, pH 7.5, 1 mM $CaCl_2$, 5 mM $MgCl_2$ and 0.5% bovine serum albumin (FractionV Ig G free)) at ~$5\times10^6$ cells/ml. For each sample 40 µl cell suspension ($1\times10^5$ cells/well) was seeded into a 96-well V-shaped plate (Greiner, Cat.#651101). Competition studies were done using 12 concentrations of competing unlabeled ligand in half-log dilutions starting with 1 µM as the highest concentration. 40 µl of antibody was added considering a final assay volume of 120 µl. 40 µl radioligand [$^{125}$I]-hC5a (Perkin Elmer, Cat. No. NEX250) was added to all samples except the background control. The final concentration of radioligand in the assay was 1 nM and the final volume was 120 µL. All samples were run in triplicate and incubated for 4 h at 4° C. Cells were then collected by centrifugation at 1200 rpm, at 4° C. for 2 min and washed three times in 100 µl of wash buffer (50 mM HEPES, pH 7.5, 1 mM $CaCl_2$, 5 mM $MgCl_2$, 150 mM NaCl and 0.5% bovine serum albumin (FractionV Ig G free)). Finally, cells were re-suspended in 30 µl wash buffer and transfered to an OPTIPLATE (Perkin Elmer, Cat. No. 6005290) and 150 µl of MICROSCINT 20 (Perkin Elmer, Cat. No. 6013621) was added to each well. The plates were covered, mixed well counted on a calibrated Top Counter with 1 h delay. The total amount of radioligand added to the assay was determined on a separate plate. The number of counts in each sample was expressed as normalized values in percentage were 100% is the maximum level of counts where 1 nM [$^{125}$I]-hC5a and no cold antibody is added, and 0% is unspecific binding determined in the presence of 1 µM cold hC5a. The data were analyzed by nonlinear regression using PRISM (GRAPHPAD).

Calcium-flux Assay
Staining of Human Neutrophils with FLUO-4 AM Cell Dye
Neutrophils were centrifuged and washed in PBS then resuspended at $1\times10^7$ cells/ml in Cell Dye and incubated at room temperature for 40 min in darkness. Cells were centrifuged and washed (to remove excess dye), centrifuged again and resuspended at $2\times10^6$ cell/ml in Cell Buffer. Cells (0.5 ml) were aliquoted into non-sterile glass FACS tubes—one tube for each sample—stored at room temperature and used within two hours. Each sample used $1\times10^6$ neutrophils.

Assay

The calcium flux assay was carried out as follows. Briefly, $1\times10^6$ neutrophils loaded with FLUO-4 AM in 0.5 ml Cell Buffer were analysed on a FACSCALIBUR flow cytometer (BD Biosciences) with neutrophils gated using x-axis FSC vs. y-axis SSC. The FL-1 (FITC) channel was used to measure neutrophil fluorescence following addition of various reagents to the tube (e.g. antibodies, C5a, ionomycin—dissolved at 10× final concentration in Cell Buffer rather than I-MGB or C-MGB). Sample fluorescence was measured continuously with a mean fluorescence intensity (MFI) value acquired every 1 second. This data was saved in a CELLQUEST (BD Biosciences) file and transferred to Excel (Microsoft) and PRISM (v4.0c, GRAPHPAD Software Inc.) for further processing and analysis. The order of adding reagents to the neutrophils and incubation times varied according to the type of assay carried out.

C5a Neutralization Assay

A 10× 3-fold serial dilution of antibody, with concentrations ranging from 1000 µg/ml to 1.37 µg/ml, was prepared. FLUO-4 AM loaded neutrophils ($1\times10^6$ in 0.5 ml Cell Buffer) were incubated with 50 µl 10× antibody solution (final Ab concentration in tube: 100-0.137 µg/ml) for 10 min at room temperature. Cells plus antibody were analysed by FACS for ~60 sec to establish baseline fluorescence. Then 50 µl 10 nM C5a was added to give a final concentration of ~1 nM and fluorescence measurement continued for another ~60 sec. If the antibody blocked C5a-induced $Ca^{2+}$-release there was no spike of fluorescence. If antibody did not neutralize the C5a then there was a spike in fluorescence. Lastly, 50 µl 1 µg/ml ionomycin was added to a final concentration of 0.1 µg/ml and fluorescence measurement continued for another ~60 sec to ensure cells were still responsive.

CD11b Receptor Upregulation

Assay Set-up

The following set up was designed to determine the ability of the identified antibodies to neutralize C5a-induced neutrophil activation by measuring changes in CD11 b expression.

Anti-05aR and isotype control antibody was diluted in PBS to 2× final concentration in a 3-fold serial dilution (from 600 to 0.003387 µg/ml) and 50 µl dispensed in duplicate into wells of 96-well U-bottom plates. A 50 µl aliquot of whole heparinised blood was added to each well. Four sets of control wells (in duplicate) contained 50 µl PBS plus 50 µl blood only. The plates were incubated for 20 min at 37° C. in a 5% $CO_2$ incubator. To activate neutrophils 50 µl human C5a, final concentration 10 or 100 nM as specified, was added to wells containing Ab and one set of control wells without antibody. PBS (50 µl) was added to a second set of control wells without antibody. Phorbol myristate acetate (PMA), final concentration 5 µg/ml, was added to a third set of control wells without antibody. The plates were incubated again for 20 min at 37° C. in a 5% $CO_2$ incubator. Finally 50 µl of a mix of anti-CD11b-PE (BD Biosciences, Cat. No 555388) diluted 1/50 in PBS (final concentration 1/200) was added to all wells (except the $4^{th}$ set of 2 control wells without Ab and without C5a or PMA—these samples provided baseline MFI values). The plates were incubated again for 20 min at 37° C. in a 5% $CO_2$ incubator then centrifuged for 3 min at 2,000 rpm to pellet the blood cells. The supernatant (150 µl) was removed and pellets resuspended in 200 µl 1×FACS Lysis Solution to lyse the red blood cells. After 5 min at room temperature the plates were centrifuged again, 200-225 µl supernatant removed and the pellets resuspended in 160 µl 1×FACS Lysis Solution. Cells were transferred to microtitre tubes for analysis by flow cytometry.

FACS and Data Analysis

The FACSCALIBUR flow cytometer (BD Biosciences) was setup with compensation parameters established for channels FL-2. Samples were gated to exclude dead cells and debris. Neutrophils were identified as having high FSC and SSC and gated. The mean fluorescence intensity (MFI) of the gated neutrophils in the FL-2 (CD11b-PE) channel was calculated.

Results were expressed as a percentage of maximum CD11 b expression with background subtracted. Maximum CD11 b expression (MaxCD11b) was the average MFI of the neutrophils incubated with C5a but without Ab. The minimum (background) CD11 b expression (MinCD11b) was the average MFI of the neutrophils incubated without C5a and without Ab. The formula used to calculate % of maximum CD11b expression for each samples was:

$$\% \text{ Max}_{sample}=(MFI_{sample}-MFI_{Min})/(MFI_{Max}-MFI_{Min})\times100$$

Data was entered into GRAPHPAD PRISM (v4.0) and fitted to the sigmoidal dose-response curve (variable slope) i.e. 4-parameter logistic equation using non-linear regression to calculate the EC50.

CD62L Receptor Down-regulation

Assay Set-up

The following set up was designed to determine the ability of the identified antibodies to neutralize C5a-induced neutrophil activation by measuring changes in CD62L expression.

The above CD11b assay was adapted for CD62L detection by using a conjugated antibody recognizing CD62L (BD Biosciences, Cat. No 559772). The experimental details specific for CD62L are given below.

FACS and Data Analysis

The FACSCALIBUR flow cytometer (BD Biosciences) was setup with compensation parameters established for channel FL-4. Samples were gated to exclude dead cells and debris. Neutrophils were identified as having high FSC and SSC and gated. The mean fluorescence intensity (MFI) of the gated neutrophils in the FL-4 (CD62L-APC) channel was calculated.

Results were expressed as a percentage of maximum CD62L expression with background subtracted. Maximum CD62L expression (MaxCD62L) was the average MFI of the neutrophils incubated without C5a and without Ab. The minimum (background) CD62L expression (MinCD62L) was the average MFI of the neutrophils incubated with C5a but without Ab. The formula used to calculate % of maximum CD62L expression for each samples was:

$$\% \text{ Max}_{sample}=(MFI_{sample}-MFI_{Min})/(MFI_{Max}-MFI_{Min})\times100$$

Data was entered into GRAPHPAD PRISM (v4.0) and fitted to the sigmoidal dose-response curve (variable slope) i.e. 4-parameter logistic equation using non-linear regression to calculate the EC50.

Results from the above assays are summarized in table 5 below.

TABLE 5

Data obtained in affinity assay, Calcium-flux assay, CD11b and CD62L assay.

| | Affinity Ccompetition ligand binding assay | IC50 Calcium-flux assay | IC50 CD11b up-regulation | IC50 CD62L down-regulation |
|---|---|---|---|---|
| 32F3A6 GL | 0.34 nM | 1.8 µg/ml | 0.7 µg/ml | 0.5 µg/ml |
| Ref. Ab Q | 0.84 nM | 7.3 µg/ml | 3.6 µg/ml | 1.9 µg/ml |

The data confirmed that 32F3A6 GL inhibits the action of C5a in a dose-dependent fashion. The inhibition on neutrophil $Ca^{2+}$ release increased with increasing concentrations of 32F3A6 GL and with a higher efficacy than Ref. Ab Q as seen by the lower IC50 value.

Similarly, 32F3A6 GL is also more efficient than Ref. Ab Q in the CD11b and CD62L regulation assay displaying a 4-5 fold high potency than Ref. Ab Q.

Further testing of 32F3A6 GL in the Neutrophil migration (Chemotaxis) Assay also showed dose dependency with an IC50 of 1.0 µg/ml.

Example 8

In Vivo Mice Model of Arthritis

The in vivo effect was tested in a K/BxN model in hC5aR KO/KI mice (WO 2009/103113 and Lee et al, Nat Biotechnol. 2006 October; 24(10):1279-84). The K/BxN mice spontaneously develop an autoimmune-like disease mediated by circulating Ab against GPI (auto-antigen glucose 6-phosphate isomerase). Serum from arthritic K/BxN mice induces disease in other mouse strains with many features of the hall marks of human RA including chronic progressive disease with joint destruction.

Animals

Human C5aR KO/KI transgenic mice (C57BL/6; H-2b; human C5aR+/+/mouse C5aR-/-; strain abbreviation: H5Rtg) aged from 8-27 weeks.

K/BxN Serum

To produce serum for experiments, KRNtg male mice were crossed with NOD female mice. F1 offspring (8-10 weeks of age) carrying the KRN transgene, which developed inflamed joints, were sacrificed and blood was collected by cardiac puncture. After 2 hours incubation at 37° C. and centrifugation for 10 min at 4,000 rpm the serum was collected. Serum from multiple mice was pooled, aliquoted and stored at -80° C. All mice in were injected with the same batch of K/BxN serum.

Arthritis Induction and Scoring

An inflammatory arthritis was induced in recipient H5Rtg mice by injecting 150 µl K/BxN serum i.p. on both day 0 and day 2. Disease progress was monitored daily by measuring paw size and determining a clinical score based on degree of inflammation in the front and rear paws and ankle joints. The change in average paw size from day 0 was calculated as follows. The thickness (in mm) of the ankles on each of the rear paws was measured daily using a caliper. The mean of the one or two readings from each of the rear paws was the average daily paw size (PS). The average paw size on day 0 was subtracted from the average daily paw size to give the average change in paw size (ΔPS) for each day of the experiment. A clinical score was calculated for each paw of each mouse based on the scoring system shown in Table 6.

The score from the 4 paws was summed to give the total clinical score (CS) for each mouse on each day of the experiment.

TABLE 6

Arthritis clinical scoring system

| Score | Appearance |
|---|---|
| 0 | normal joint |
| 1 | mild/moderate swelling of the ankle and/or one swollen digit |
| 2 | swollen ankle or swelling in two or more digits |
| 3 | severe swelling along all aspects of paw or all five digits |

To determine which mice entered the treatment phase on day 5, an "RA Score" was calculated for each mouse by multiplying the clinical score by the change in paw size from day 0 (in mm). Generally only mice that had an RA Score >0.7 were entered into the treatment stage of the study.

Therapeutic Treatment with 32F3A6 GL

Figure 4:
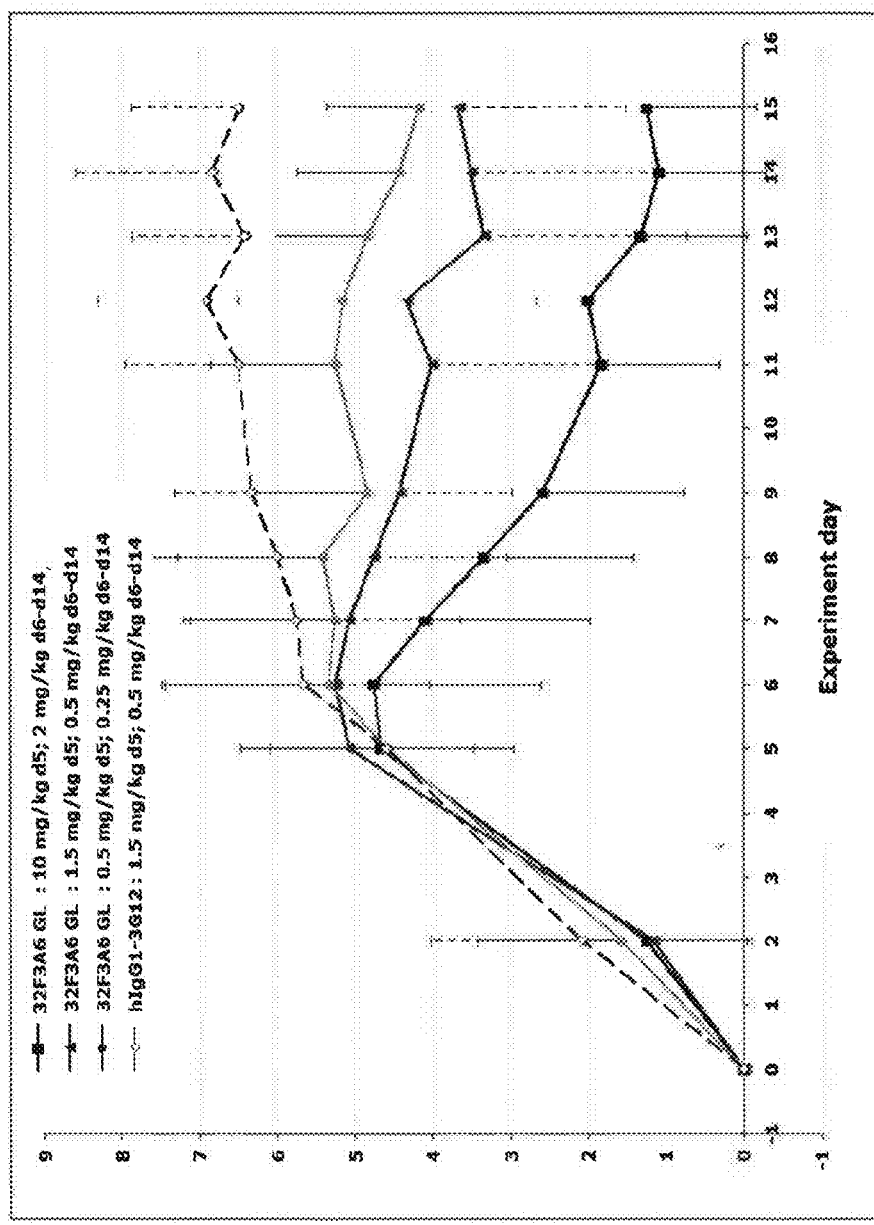
FIG. 4 Clinical scores for three treatment groups given a single loading dose (arrow) of 0.5, 1.5 or 10 mg/kg i.p. 5 days after established inflammation in the K/BxN-hC5aR-KO/KI serum transfer model, followed by 9 daily doses of 0.25, 0.5 or 2 mg/kg, respectively, with error bars representing ±SD. Controls received IgG1 3G12.

After disease onset (day 0) the KO/KI hC5aR mice were given a loading dose of 32F3A6 GL on day 5 and then 9 daily doses. The loading dosages were 10, 1.5 and 0.5 mg/kg and the daily dosages 2, 0.5 and 0.25 mg/kg. Clinical scores (mean+/-SD) for each treatment group is shown in FIG. 4. Treatment with NNC0215-0384 produced a dose-dependent reduction in inflammation compared to mice treated with an irrelevant control antibody. A similar effect was observed based on changes in average paw size (not shown)

Example 9

C5a Expression Level in Psoriatic Arthritis Patients

Figure 5:
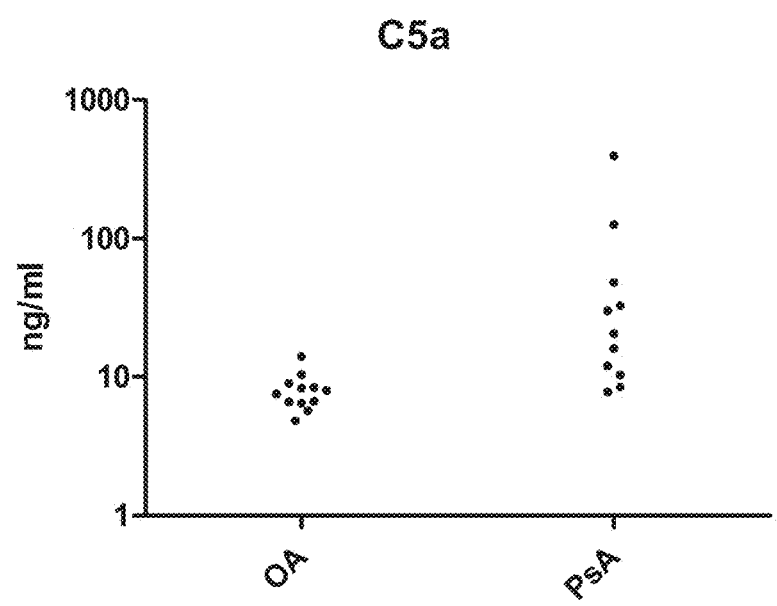
FIG. 5 C5a protein expression in synovial fluid Psoriatic Arthritis and Osteoarthritis patients (controls). The C5a level was significantly elevated in the psoriatic arthritis patient group (p=0.001; Mann-Whitney).

C5a was measured in synovial fluid samples from 11 Psoriatic Arthritis and 12 Osteoarthritis patients as controls. The protocol from a commercial C5a ELISA kit was followed (BD OptEIA™, Human C5a ELISA Kit II (BD Biosciences; cat. No. 557965)). The data are provided in FIG. 5 and summarized in table 7 below. The C5a level was significantly elevated in the psoriatic arthritis patient group (p=0.001; Mann-Whitney) indicating that C5a may be a driver of synovial inflammation in psoriatic arthritis.

TABLE 7

Detection levels of C5a in synovial fluid from controls and Psoriatic arthritis patients.

| | Controls (Osteoarthritis patients) | Psoriatic arthritis patients |
|---|---|---|
| Average C5a level (±SEM) | 7.989 ± 0.6999 | 64.17 ± 34.53 |

Example 10

C5aR Expression in Synovium from Patients with Psoriatic Arthritis

Tissue microarray (TMA) slides containing formalin fixed and paraffin embedded synovial biopsies from patients with PsA (n=9), and within normal limits (n=5) were obtained from Biochain Institute Inc./BioCat GmbH, Heidelberg, Germany. One PsA sample from the collaboration with Dr. Bliddal (Frederiksberg Hospital, Denmark) and Dr. Søe (Gentofte Hospital, Denmark). All human materials were obtained with informed consent from the donors/or close relatives, and approval from relevant local ethical committees BioCat Ge, personal communication; Cambridge BioSciences, Supplier information: Tissue Supply Network (www.bioscience. co.uk). The sample from Drs Bliddal/Søe was obtained under the ethical permit no. H-4-2009-117. The following antibodies were used: Mouse monoclonal anti-human C5aR (R&D Systems, MAB3648 clone 347214 (IgG2a)). Mouse IgG2a isotype specific control (Dako, X0943, clone DAK-GO5). Biotin conjugated Donkey anti-mouse Jackson ImmunoReseach (715-065-150).

Immunohistochemistry was performed as follows. The sections were deparaffinised in xylene and rehydrated in decreasing concentrations of alcohols. Antigen retrieval was performed in Tris-EGTA buffer (10 mM; 0.5 mM), pH 9.0 in a microwave oven for 15 min. Endogenous peroxidase activity was blocked with 3% H2O2, and endogenous biotin was blocked by incubation with Avidin and Biotin blocking solutions for 10 min, respectively, according to the manufacturer. Non-specific binding was blocked by incubation with TBS containing 3% skimmed milk, 7% donkey serum, 3% human serum, and 3.2 mg/ml Poly-L-Lysine (PLL) for 30 min. The primary and secondary antibodies were diluted in a Tris buffer containing 0.5% skimmed milk, 7% donkey and 3% human sera, and incubation was performed overnight at 4° C., and 60 min at room temperature, respectively. The first amplification step was performed by incubation with Vectastain ABC peroxidase kit, diluted in 0.1 M Tris-HCl buffer (pH 7.5) containing 0.5% Du Pont Blocking Reagent (TNB) for 30 min, followed by a second amplification step with incubation in biotinylated Tyramide for 6 min. The final amplification was performed by an additional incubation with the Vectastain ABC peroxidase kit, diluted as described above for 30 min. The chromogenic reaction was achieved with diaminobenzidin. Nuclei were counterstained with haematoxylin and the sections were rehydrated, cleared in xylene and mounted with Eukitt. Evaluation of the TMAs for C5aR protein expression in RA, OA and normal synovium was performed blinded to the observer. An Olympus BX51 microscope equipped with a DP70 digital camera (Olympus Denmark A/S; Ballerup, Denmark) was used for evaluation of the sections.

Results

C5aR-immunopositive cells were found intermingled in lymphoid aggregates in the synovial sublining layer in 8 out of 10 patients with psoriatic arthritis, and in the stroma of 10 out of 10 patients with psoriatic arthritis. The controls did not display any C5aR staining in these synovial compartments (0/5). C5aR-immunopositive synoviocytes were detected in the lining layer cells in controls 4 out of 5 as well as in 10 out of 10 patients with psoriatic arthritis. The results are summarized in table 8 below.

TABLE 8

Detection of C5aR+ cells in the normal synovium and synovium from patients with psoriatic arthritis. P-value (Fischer's exact test) for difference between C5aR expression in patients with psoriatic arthritis compared to normal synovium: 0.007 (lymphoid aggregates) and 0.0003 (stroma).

| Synovial compartment | Normal | Psoriatic arthritis patients |
|---|---|---|
| Infiltrating C5aR+ cells in lymphoid aggregates in synovial sublining tissue | 0/5 | 8/10 |
| C5aR+ cells in the stroma | 0/5 | 10/10 |
| C5aR+ synoviocytes in the lining layer | 4/5 | 10/10 |

Example 11

Inhibition of Neutrophil Migration Induced by Synovial Fluid from Psoriatic Arthritis Patients by Anti-C5aR Neutrophil Granulocyte Migration (Chemotaxis) Assay The potency of the antibodies to inhibit hC5a-dependent migration of human neutrophjl granulocytes (human PMNs (PolyMorphoNuclear leukocytes)) was analysed in a Boyden chamber assay using BD FLUOROBLOK 96-multiwell insert systems.

Human PMNs were obtained from human blood samples drawn into vials containing EDTA. The blood cells were separated by centrifugation of blood (4 parts) through a Ficoll-Paque PLUS (GE Health Care) gradient (3 parts) for 30 min (400×g) at room temperature. The PMN-containing layer was suspended in PBS (phosphate buffered saline) containing dextran-500 (Sigma) for 1 h to remove contaminating erythrocytes. The supernatant was centrifuged for 5 min (250×g) at room temperature and remaining erythrocytes were osmotically lysed using 0.2% NaCl for 55 s. The solution was made isotonic by 1.2% NaCl+PBS and centrifuged at 250×g for 5 min, before the osmotic lysis was repeated. After centrifugation the PMNs were resuspended in reaction mixture (RM): HBSS (cat no 14175 Gibco) contains NaCl 137 mM, KCl 5.3 mM, $Na_2HPO_4$ 0.33 mM, $NaHCO_3$ 4 mM, $KH_2PO_4$ 0.44 mM, Glucose 5 mM; supplemented with $MgSO_4 \cdot 7H_2O$ 0.4 mM, $MgCl_2$, 0.5 mM, $CaCl_2$ 0.5 mM, HEPES 20 mM. Cell density was determined by NUCLEOCOUNTER (Chemometec). The PMN suspension contained >95% neutrophils as evaluated by microscopy of Giemsa-stained samples.

Loading PMNs: Calcein, AM, (Fluka) was dissolved in DMSO (Dimethyl sulphoxide) and diluted 1000× in RM with cells (2×10$^6$ cells per ml) to yield a concentration of 10 µM. The suspension was incubated for 30 min in incubator at 37° C. and then washed 3 times with RM to remove excess Calcein. Finally the cells were resuspended in RM (4×10$^6$ cells/ml).

Human synovial fluid (SF) was obtained from 2 psoriatic arthritis patients by knee puncture. After removal of cells by centrifugation the samples were frozen and stored at −80° C. For migration experiments the samples were thawed and diluted 2× using RM containing 0.2% EDTA.

Migration was evaluated by the Boyden chamber technique using FLUOROBLOK® 3 µm pore size 96-well (cat. No. 351161.BD Falcon (VWR)). The upper chamber i.e. the inserts containing FLUOROBLOK membrane, was coated with human fibrinogen (cat no F3879-1G, Sigma) in 1 mg/ml PBS at 37° C. for 2 hrs. After washing the membranes were blocked with a solution containing 2% bovine serum albumin (BSA), in PBS. After another wash using RM, 10$^5$ Calcein-loaded PMNs with or without the hC5aR-antibodies (100 µg/ml) were added to each well and placed in the receiver plate (lower chamber) which contained the control solution or the chemoattractant solution (hC5a (Sigma, or samples of synovial fluid)). Each group comprised of 4-6 wells. Quantitation of cell migration is achieved by measuring the fluorescence of the cells in the lower chamber. Since the FLUOROBLOK membrane effectively blocks the passage of light from 490-700 nm, fluorescence from cells that have not entered the lower chamber is not detected at of 485/530 nm. The plate was read at 485/538 nm excitation/emission wavelengths, 37° C. every 5 min for 60 min in fluorescence plate reader with bottom reading capabilities (SPECTRAMAX, Molecular devices, or FLUOROSCAN, Thermo Labsystems).

Migration was assessed by fluorescence values at 60 min expressed as relative fluorescence values. In table 9, migration in the presence of Isotype antibody is set to 100% and the ability of the anti-C5aR antibody to inhibit migration is calculated. Migration was clearly attenuated by the hC5aR antibody. Migration elicited by 10 nM hC5a was inhibited 83%. The values for the three SF samples were: 15%, 70% and 48%. The results demonstrate that the C5aR-antibody inhibited the chemoattractive effect of SF from psoriatic arthritis patients.

TABLE 9

Migration of PMNs in response to hC5a or synovial fluid from three psoriatic arthritis patients and inhibition hereof by hC5aR antibody (Ref antibody Q). All values are normalized to migration detected when incubated with isotype antibody.

|  | hC5a (10 nM C5a) | SF sample donor 1 | SF sample donor 1 | SF sample donor 1 |
|---|---|---|---|---|
| Isotype antibody | 100 | 100 | 100 | 100 |
| Anti-C5aR | 17 | 85 | 30 | 52 |

Example 12

C5aR Expressing in the Intestine from Patients with Crohn's Disease and Ulcerative Colitis Intestinal tissue samples within normal limits (n=14), from patients with ulcerative colitis (n=21) and Crohn's disease (n=25) were obtained from Cambridge Bioscience (Cambridge, UK). All human materials were obtained with informed consent from the donors/or close relatives, and approval from relevant local ethical committees Cambridge BioSciences, Supplier information: Tissue Supply Network (www.bioscience.co.uk). The antibodies used and immunohistochemical protocol as described in Example 9.

Semi-quantitative Scoring

C5aR immunopositive (C5aR$^+$) cells were semi-quantitatively scored as follows:

The mucosa-associated lymphoid compartments were individually scored: Mucosa (M): intraepithelial lymphocyte (IEL) compartment (surface epithelium), lamina propria, and follicle-associated epithelium (FAE). Submucosa (SM): isolated (solitary) lymphoid follicles (ILF), Peyer's patches (ileum)/colonic IEL (colon) and isolated infiltrating lymphocytes. Muscularis Externa (ME): IELs and isolated infiltrating lymphocytes. Each compartment was scored on a scale from 0-4: 0, no; 1, few; 2 moderate; 3, many and 4, abundant numbers of C5aR$^+$ cells. An accumulated score was calculated for each intestinal layer (M, SM, ME) and in total (M+SM+ME) for the entire intestine. Max score: M=12, SM=12, ME=8 and for the entire intestine 32. The semi-quantitative scoring of the immunohistochemical data for C5aR protein expression were analysed by Kruskal-Wallis test with Dunn's multiple comparison post-test in GRAPH-PAD PRISM 5. $P<0.05$ was considered significant.

Results

C5aR positive neutrophils and myeloid-like cells were found in the intraepithelial lymphocyte compartment, in the follicle associated epithelium and as solitary cells in lamina propria of the mucosa in 23 out of 25 of patients with CD, 19 out of 21 patients with UC and in 7 out of 14 normal intestinal samples (P-values (Fisher's exact test) 0.005 and 0.015, respectively). In addition, C5aR positive cells were found in Peyer's patches/colonic-lymphoid follicles; isolated (solitary) lymphoid follicles and as solitary cells of the submucosa in 21 out of 25 patients with CD and 18 out of 21 UC patients compared to 7 out of 14 normal intestinal samples (P-values (Fisher's exact test) 0.03 and not significant, respectively). Finally, C5aR positive cells were found infiltrating muscularis externa from patients with CD and UC, as well as in the normal intestine. Results are presented in FIG. 6 and summarized in table 10. Based on the semi-quantitative analysis it was found that C5aR is significantly higher expressed in the intestine from patients with CD ($P<0.01$) and UC ($P<0.05$) compared to the normal intestine in the entire intestinal wall e.g. accumulated score over the three intestinal layers (mucosa, submucosa, and muscularis externa).

TABLE 10

Summary of C5aR expression in the intestine from patients with Crohn's disease and ulcerative colitis compared to normal intestine.

|  | C5aR expression in | | |
|---|---|---|---|
| Diagnosis | Mucosa | Submucosa | Muscularis Externa |
| Normal | 7/14 | 7/14 | 8/14 |
| Crohn's disease | 23/25 | 21/25 | 19/25 |
| Ulcerative colitis | 19/21 | 18/21 | 11/21 |

While certain features of the invention have been illustrated and described herein, many modifications, substitutions, changes, and equivalents will now occur to those of ordinary skill in the art. It is, therefore, to be understood that the appended embodiments are intended to cover all such modifications and changes as fall within the true spirit of the invention.

The invention claimed is:

1. An antibody that specifically binds C5aR, wherein the antibody comprises a heavy chain variable region comprising:
   a CDR1 sequence comprising SEQ ID 1, 9, 17 or 25; a CDR2 sequence comprising SEQ ID 2, 10, 18 or 26; and a CDR3 sequence comprising SEQ ID 3, 11, 19 or 27; and
   wherein the antibody comprises a light chain variable region comprising:
   a CDR1 sequence comprising SEQ ID 5, 13, 21 or 29; a CDR2 sequence comprising SEQ ID 6, 14, 22 or 30; and a CDR3 sequence comprising SEQ ID 7, 15, 23 or 31.

2. The antibody according to any claim 1, wherein the antibody is selected from:
   a. an antibody where the CDRs of the variable region of the heavy chain comprise SEQ ID 1, 2 and 3 and where the CDRs of the variable light chain comprise SEQ ID 5, 6 and 7;
   b. an antibody where the CDRs of the variable region of the heavy chain comprise SEQ ID 9,10 and 11 and where the CDRs of the variable light chain comprises SEQ ID 13, 14 and 15;
   c. an antibody where the CDRs of the variable region of the heavy chain comprise SEQ ID 17,18 and 19 and where the CDRs of the variable light chain comprises SEQ ID 21, 22 and 23;
   d. an antibody where the CDRs of the variable region of the heavy chain comprise SEQ ID 25, 26 and 27 and where the CDRs of the variable light chain comprises SEQ ID 29, 30 and 31.

3. The antibody according to claim 1, wherein the variable region of the heavy chain of said antibody comprises a sequence at least 80% identical to SEQ ID NO: 4, 12, 20 or 28 and/or wherein the variable region of the light chain of said antibody comprises a sequence at least 8094% identical to SEQ ID NO: 8, 16, 24 or 32.

4. The antibody according to claim 1, wherein the antibody is a human antibody.

5. The antibody according to claim 1, wherein said antibody binds the 2nd extracellular loop of human C5aR.

6. The antibody according to claim 1 wherein the affinity of the antibody as measured by competition ligand binding assay on neutrophils is below 0.80 nM.

7. The antibody according to claim 1 wherein the antibody significantly inhibits or reduces binding of C5a to C5aR.

8. The antibody according to claim 1 wherein the antibody significantly inhibits migration of human neutrophils in vitro.

9. The antibody according to claim 1, wherein the Fc region has decreased binding affinity to one or more Fcγ receptors compared to IgG1, IgG2, IgG4 or IgG4/G2 Fc reference sequences as defined by SEQ ID NO 33, 34, 35 and 36, respectively.

10. The antibody according to claim 1 wherein the antibody does not significantly induce antibody dependent cellular cytotoxicity (ADCC), complement dependent cytotoxicity (CDC) and/or phagocytosis of neutrophils in vitro.

11. The antibody according to claim 1 wherein the Fc region is IgG1 (SEQ ID NO: 33), IgG2 (SEQ ID NO: 34), IgG2/4 (SEQ ID NO: 35), or IgG4 (SEQ ID NO: 36), with one or more of the following point mutations:
   a. E233P;
   b. L234A or V234A or F234L or F234V;
   c. L235E or L235A;
   d. G236R or G236A;
   e. G237A;
   f. N297Q;
   g. L328R;
   h. A330S;
   i. P331S.

12. A method of inhibiting binding of C5a to C5aR in subject comprising administering the antibody of claim 1 to said subject, thereby inhibiting binding of C5a to C5aR in the subject.

13. The method of claim 12, wherein the subject has an inflammatory or immunological disease or disorder.

14. A method of inhibiting hC5a mediated neutrophil migration in a subject comprising administering the antibody of claim 1 to said subject, thereby inhibiting hC5a mediated neutrophil migration in the subject.

15. The method of claim 14, wherein the subject has an inflammatory or immunological disease or disorder.

16. A method of inhibiting binding of C5a to C5aR in subject comprising administering the antibody of claim 2 to said subject, thereby inhibiting binding of C5a to C5aR in the subject.

17. The method of claim 16, wherein the subject has an inflammatory or immunological disease or disorder.

18. A method of inhibiting hC5a mediated neutrophil migration in a subject comprising administering the antibody of claim 2 to said subject, thereby inhibiting hC5a mediated neutrophil migration in the subject.

19. The method of claim 18, wherein the subject has an inflammatory or immunological disease or disorder.

* * * * *

SEQUENCE LISTING

<160> NUMBER OF SEQ ID NOS: 41

<210> SEQ ID NO 1
<211> LENGTH: 5
<212> TYPE: PRT
<213> ORGANISM: Artificial Sequence
<220> FEATURE:
<223> OTHER INFORMATION: Synthetic sequence

<400> SEQUENCE: 1

Asp Tyr Gly Met His
1               5

<210> SEQ ID NO 2
<211> LENGTH: 16
<212> TYPE: PRT
<213> ORGANISM: Artificial Sequence
<220> FEATURE:
<223> OTHER INFORMATION: Synthetic sequence

<400> SEQUENCE: 2

Val Ile Trp Phe Asp Gly Ile Asn Lys Tyr Tyr Gly Asp Ser Val Lys
1               5                   10                  15

<210> SEQ ID NO 3
<211> LENGTH: 13
<212> TYPE: PRT
<213> ORGANISM: Artificial Sequence
<220> FEATURE:
<223> OTHER INFORMATION: Synthetic sequence

<400> SEQUENCE: 3

Thr Tyr Phe Gly Pro Gly Thr Thr Glu Phe Phe Gln His
1               5                   10

<210> SEQ ID NO 4
<211> LENGTH: 122
<212> TYPE: PRT
<213> ORGANISM: Artificial Sequence
<220> FEATURE:
<223> OTHER INFORMATION: Synthetic sequence

<400> SEQUENCE: 4

Gln Val Gln Leu Val Glu Ser Gly Gly Gly Leu Val Arg Pro Gly Arg
1               5                   10                  15

Ser Leu Arg Leu Ser Cys Ala Ala Ser Gly Phe Thr Phe Arg Asp Tyr
            20                  25                  30

Gly Met His Trp Val Arg Gln Ala Pro Gly Lys Ser Leu Glu Trp Val
        35                  40                  45

Ala Val Ile Trp Phe Asp Gly Ile Asn Lys Tyr Tyr Gly Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Met Tyr Tyr Cys
                85                  90                  95

Val Gly Thr Tyr Phe Gly Pro Gly Thr Thr Glu Phe Phe Gln His Trp
            100                 105                 110

Gly Gln Gly Thr Leu Val Thr Val Ser Ser
        115                 120

<210> SEQ ID NO 5
<211> LENGTH: 11
<212> TYPE: PRT
<213> ORGANISM: Artificial Sequence
<220> FEATURE:
<223> OTHER INFORMATION: Synthetic sequence

<400> SEQUENCE: 5

Arg Ala Ser Gln Ser Val Ser Ser Tyr Leu Ala
1               5                   10

<210> SEQ ID NO 6
<211> LENGTH: 7
<212> TYPE: PRT
<213> ORGANISM: Artificial Sequence

```
<220> FEATURE:
<223> OTHER INFORMATION: Synthetic sequence

<400> SEQUENCE: 6

Asp Ala Ser Asn Arg Ala Thr
1               5

<210> SEQ ID NO 7
<211> LENGTH: 8
<212> TYPE: PRT
<213> ORGANISM: Artificial Sequence
<220> FEATURE:
<223> OTHER INFORMATION: Synthetic sequence

<400> SEQUENCE: 7

Gln Gln Arg Ser Asn Trp Pro Thr
1               5

<210> SEQ ID NO 8
<211> LENGTH: 107
<212> TYPE: PRT
<213> ORGANISM: Artificial Sequence
<220> FEATURE:
<223> OTHER INFORMATION: Synthetic sequence

<400> SEQUENCE: 8

Glu Ile Val Leu Thr Gln Ser Pro Ala Thr Leu Ser Leu Ser Pro Gly
1               5                  10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Thr
                85                  90                  95

Phe Gly Pro Gly Thr Lys Val Asp Ile Lys Arg
            100                 105

<210> SEQ ID NO 9
<211> LENGTH: 5
<212> TYPE: PRT
<213> ORGANISM: Artificial Sequence
<220> FEATURE:
<223> OTHER INFORMATION: Synthetic sequence

<400> SEQUENCE: 9

Ser Tyr Val Met His
1               5

<210> SEQ ID NO 10
<211> LENGTH: 15
<212> TYPE: PRT
<213> ORGANISM: Artificial Sequence
<220> FEATURE:
<223> OTHER INFORMATION: Synthetic sequence

<400> SEQUENCE: 10

Ala Ile Asp Thr Gly Gly Gly Thr Tyr Tyr Ala Asp Ser Val Lys
1               5                   10                  15
```

<210> SEQ ID NO 11
<211> LENGTH: 16
<212> TYPE: PRT
<213> ORGANISM: Artificial Sequence
<220> FEATURE:
<223> OTHER INFORMATION: Synthetic sequence

<400> SEQUENCE: 11

Asp Tyr Tyr Tyr Tyr Ala Ser Gly Ser Tyr Tyr Lys Ala Phe Asp Ile
1               5                   10                  15

<210> SEQ ID NO 12
<211> LENGTH: 124
<212> TYPE: PRT
<213> ORGANISM: Artificial Sequence
<220> FEATURE:
<223> OTHER INFORMATION: Synthetic sequence

<400> SEQUENCE: 12

Glu Val Gln Leu Val Gln Ser Gly Gly Gly Leu Val His Pro Gly Gly
1               5                   10                  15

Ser Leu Arg Leu Ser Cys Ala Gly Ser Gly Phe Thr Phe Ser Ser Tyr
            20                  25                  30

Val Met His Trp Val Arg Gln Ala Pro Gly Lys Gly Leu Glu Trp Val
        35                  40                  45

Ser Ala Ile Asp Thr Gly Gly Gly Thr Tyr Tyr Ala Asp Ser Val Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Met Ala Val Tyr Tyr Cys Ala
                85                  90                  95

Arg Asp Tyr Tyr Tyr Tyr Ala Ser Gly Ser Tyr Tyr Lys Ala Phe Asp
            100                 105                 110

Ile Trp Gly Gln Gly Thr Met Val Thr Val Ser Ser
        115                 120

<210> SEQ ID NO 13
<211> LENGTH: 12
<212> TYPE: PRT
<213> ORGANISM: Artificial Sequence
<220> FEATURE:
<223> OTHER INFORMATION: Synthetic sequence

<400> SEQUENCE: 13

Arg Ala Ser Gln Ser Val Ser Ser Arg Tyr Leu Ala
1               5                   10

<210> SEQ ID NO 14
<211> LENGTH: 7
<212> TYPE: PRT
<213> ORGANISM: Artificial Sequence
<220> FEATURE:
<223> OTHER INFORMATION: Synthetic sequence

<400> SEQUENCE: 14

Gly Ala Ser Ser Arg Ala Thr
1               5

<210> SEQ ID NO 15
<211> LENGTH: 8
<212> TYPE: PRT
<213> ORGANISM: Artificial Sequence
<220> FEATURE:
<223> OTHER INFORMATION: Synthetic sequence

<400> SEQUENCE: 15

Gln Gln Tyr Gly Ser Pro Leu Thr
1               5

<210> SEQ ID NO 16
<211> LENGTH: 108
<212> TYPE: PRT
<213> ORGANISM: Artificial Sequence
<220> FEATURE:
<223> OTHER INFORMATION: Synthetic sequence

<400> SEQUENCE: 16

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Arg
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Pro Leu
                85                  90                  95

Thr Phe Gly Gln Gly Thr Lys Leu Glu Ile Lys Arg
            100                 105

<210> SEQ ID NO 17
<211> LENGTH: 5
<212> TYPE: PRT
<213> ORGANISM: Artificial Sequence
<220> FEATURE:
<223> OTHER INFORMATION: Synthetic sequence

<400> SEQUENCE: 17

Asn Tyr Gly Met His
1               5

<210> SEQ ID NO 18
<211> LENGTH: 16
<212> TYPE: PRT
<213> ORGANISM: Artificial Sequence
<220> FEATURE:
<223> OTHER INFORMATION: Synthetic sequence

<400> SEQUENCE: 18

Val Ile Trp Tyr Asp Gly Ile Asn Lys Tyr Tyr Ala Asp Ser Val Lys
1               5                   10                  15

<210> SEQ ID NO 19
<211> LENGTH: 13
<212> TYPE: PRT
<213> ORGANISM: Artificial Sequence
<220> FEATURE:
<223> OTHER INFORMATION: Synthetic sequence

<400> SEQUENCE: 19

Thr Tyr Tyr Thr Ser Gly Ser Ser Lys His Phe Gln Pro
1               5                   10

<210> SEQ ID NO 20
<211> LENGTH: 122

```
<212> TYPE: PRT
<213> ORGANISM: Artificial Sequence
<220> FEATURE:
<223> OTHER INFORMATION: Synthetic sequence

<400> SEQUENCE: 20

Gln Val Gln Leu Val Glu Ser Gly Gly Gly Val Val Gln Pro Gly Arg
1               5                   10                  15

Ser Leu Arg Leu Ser Cys Val Ala Ser Gly Phe Thr Phe Ser Asn Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ile Asn Lys Tyr Tyr Ala Asp Ser Val
    50                  55                  60

Lys Gly Arg Phe Thr Ile Ser Arg Asp Asn Ser Lys Ser Thr Leu Tyr
65                  70                  75                  80

Leu Gln Met Asn Ser Leu Arg Ala Glu Asp Thr Ala Val Tyr Tyr Cys
                85                  90                  95

Ala Gly Thr Tyr Tyr Thr Ser Gly Ser Ser Lys His Phe Gln Pro Trp
            100                 105                 110

Gly Gln Gly Thr Leu Val Thr Val Ser Ser
        115                 120

<210> SEQ ID NO 21
<211> LENGTH: 11
<212> TYPE: PRT
<213> ORGANISM: Artificial Sequence
<220> FEATURE:
<223> OTHER INFORMATION: Synthetic sequence

<400> SEQUENCE: 21

Arg Ala Ser Gln Ser Val Ser Ser Tyr Leu Ser
1               5                   10

<210> SEQ ID NO 22
<211> LENGTH: 7
<212> TYPE: PRT
<213> ORGANISM: Artificial Sequence
<220> FEATURE:
<223> OTHER INFORMATION: Synthetic sequence

<400> SEQUENCE: 22

Asp Ala Ser Asn Arg Ala Thr
1               5

<210> SEQ ID NO 23
<211> LENGTH: 8
<212> TYPE: PRT
<213> ORGANISM: Artificial Sequence
<220> FEATURE:
<223> OTHER INFORMATION: Synthetic sequence

<400> SEQUENCE: 23

Gln Gln Arg Ser Asn Trp Pro Thr
1               5

<210> SEQ ID NO 24
<211> LENGTH: 107
<212> TYPE: PRT
<213> ORGANISM: Artificial Sequence
<220> FEATURE:
<223> OTHER INFORMATION: Synthetic sequence

<400> SEQUENCE: 24
```

-continued

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ser Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Thr
                85                  90                  95

Phe Gly Pro Gly Thr Lys Val Asp Ile Lys Arg
            100                 105
```

<210> SEQ ID NO 25
<211> LENGTH: 5
<212> TYPE: PRT
<213> ORGANISM: Artificial Sequence
<220> FEATURE:
<223> OTHER INFORMATION: Synthetic sequence

<400> SEQUENCE: 25

```
Asn Tyr Asp Met Ser
1               5
```

<210> SEQ ID NO 26
<211> LENGTH: 15
<212> TYPE: PRT
<213> ORGANISM: Artificial Sequence
<220> FEATURE:
<223> OTHER INFORMATION: Synthetic sequence

<400> SEQUENCE: 26

```
Ala Phe Ser Ser Asp Gly Tyr Thr Phe Tyr Pro Asp Ser Leu Lys
1               5                   10                  15
```

<210> SEQ ID NO 27
<211> LENGTH: 12
<212> TYPE: PRT
<213> ORGANISM: Artificial Sequence
<220> FEATURE:
<223> OTHER INFORMATION: Synthetic sequence

<400> SEQUENCE: 27

```
His Ala Asp Tyr Ala Asn Tyr Pro Val Met Asp Tyr
1               5                   10
```

<210> SEQ ID NO 28
<211> LENGTH: 120
<212> TYPE: PRT
<213> ORGANISM: Artificial Sequence
<220> FEATURE:
<223> OTHER INFORMATION: Synthetic sequence

<400> SEQUENCE: 28

```
Glu Val Lys Leu Val Glu Ser Gly Gly Gly Leu Val Lys Pro Gly Gly
1               5                   10                  15

Ser Leu Lys Leu Ser Cys Ser Ala Ser Gly Phe Ala Phe Ser Asn Tyr
            20                  25                  30

Asp Met Ser Trp Val Arg Gln Thr Pro Glu Lys Arg Leu Glu Trp Val
        35                  40                  45
```

Ala Ala Phe Ser Ser Asp Gly Tyr Thr Phe Tyr Pro Asp Ser Leu Lys
    50                  55                  60

Gly Arg Phe Thr Ile Ser Arg Asp Asn Ala Arg Asn Thr Leu Tyr Leu
65                  70                  75                  80

Gln Met Ser Ser Leu Gly Ser Glu Asp Thr Ala Leu Tyr Cys Cys Ala
                85                  90                  95

Arg His Ala Asp Tyr Ala Asn Tyr Pro Val Met Asp Tyr Trp Gly Gln
            100                 105                 110

Gly Thr Ser Val Thr Val Ser Ser
            115                 120

<210> SEQ ID NO 29
<211> LENGTH: 11
<212> TYPE: PRT
<213> ORGANISM: Artificial Sequence
<220> FEATURE:
<223> OTHER INFORMATION: Synthetic sequence

<400> SEQUENCE: 29

Arg Ala Ser Gln Gly Ile Ser Ser Trp Leu Ala
1               5                   10

<210> SEQ ID NO 30
<211> LENGTH: 7
<212> TYPE: PRT
<213> ORGANISM: Artificial Sequence
<220> FEATURE:
<223> OTHER INFORMATION: Synthetic sequence

<400> SEQUENCE: 30

Ala Ala Ser Ser Leu Gln Ser
1               5

<210> SEQ ID NO 31
<211> LENGTH: 9
<212> TYPE: PRT
<213> ORGANISM: Artificial Sequence
<220> FEATURE:
<223> OTHER INFORMATION: Synthetic sequence

<400> SEQUENCE: 31

Gln Gln Tyr Asn Ser Tyr Pro Arg Thr
1               5

<210> SEQ ID NO 32
<211> LENGTH: 108
<212> TYPE: PRT
<213> ORGANISM: Artificial Sequence
<220> FEATURE:
<223> OTHER INFORMATION: Synthetic sequence

<400> SEQUENCE: 32

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

```
Glu Asp Phe Ala Thr Tyr Tyr Cys Gln Gln Tyr Asn Ser Tyr Pro Arg
                85                  90                  95

Thr Phe Gly Gln Gly Thr Lys Val Glu Ile Lys Arg
            100                 105

<210> SEQ ID NO 33
<211> LENGTH: 330
<212> TYPE: PRT
<213> ORGANISM: Homo sapiens

<400> SEQUENCE: 33

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 34
<211> LENGTH: 326
<212> TYPE: PRT
<213> ORGANISM: Homo Sapiens

<400> SEQUENCE: 34

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325
```

<210> SEQ ID NO 35
<211> LENGTH: 326
<212> TYPE: PRT
<213> ORGANISM: Artificial Sequence
<220> FEATURE:
<223> OTHER INFORMATION: Synthetic sequence

<400> SEQUENCE: 35

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser Gln Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Tyr Arg Val Val Ser Val Leu Thr Val Leu His Gln Asp Trp
            180                 185                 190

Leu Asn Gly Lys Glu Tyr Lys Cys Lys Val Ser Asn Lys Gly Leu Pro
        195                 200                 205

Ser Ser Ile Glu Lys Thr Ile Ser Lys Ala Lys Gly Gln Pro Arg Glu
    210                 215                 220

Pro Gln Val Tyr Thr Leu Pro Pro Ser Gln Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Val Leu Asp Ser Asp Gly Ser Phe Phe Leu Tyr Ser Arg
        275                 280                 285

Leu Thr Val Asp Lys Ser Arg Trp Gln Glu Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Leu Gly Lys
            325

<210> SEQ ID NO 36
<211> LENGTH: 327
<212> TYPE: PRT
<213> ORGANISM: Artificial Sequence
<220> FEATURE:
<223> OTHER INFORMATION: Synthetic sequence

<400> SEQUENCE: 36

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

```
Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Ser Leu Gly Thr Lys Thr
 65                  70                  75                  80

Tyr Thr Cys Asn Val Asp His Lys Pro Ser Asn Thr Lys Val Asp Lys
                 85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
        130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 37
<211> LENGTH: 120
<212> TYPE: PRT
<213> ORGANISM: Homo sapiens

<400> SEQUENCE: 37

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met His Trp Val Arg Gln Ala Thr Gly Lys Gly Leu Glu Trp Val
        35                  40                  45

Ser Ala Ile Gly Thr Ala Gly Asp Thr Tyr Tyr Pro Gly Ser Val Lys
    50                  55                  60

Gly Arg Phe Thr Ile Ser Arg Glu Asn Ala Lys Asn Ser Leu Tyr Leu
```

```
65                  70                  75                  80

Gln Met Asn Ser Leu Arg Ala Gly Asp Thr Ala Val Tyr Tyr Cys Ala
                85                  90                  95

Arg Tyr Tyr Tyr Gly Ser Gly Ser Tyr Tyr Ala Phe Asp Ile Trp Gly
            100                 105                 110

Gln Gly Thr Met Val Thr Val Ser
        115                 120

<210> SEQ ID NO 38
<211> LENGTH: 105
<212> TYPE: PRT
<213> ORGANISM: Homo Sapiens

<400> SEQUENCE: 38

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Thr Phe
                85                  90                  95

Gly Gln Gly Thr Lys Leu Glu Ile Lys
            100                 105

<210> SEQ ID NO 39
<211> LENGTH: 124
<212> TYPE: PRT
<213> ORGANISM: Artificial Sequence
<220> FEATURE:
<223> OTHER INFORMATION: Synthetic sequence

<400> SEQUENCE: 39

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Val Met His Trp Val Arg Gln Ala Thr Gly Lys Gly Leu Glu Trp Val
        35                  40                  45

Ser Ala Ile Asp Thr Gly Gly Thr Tyr Tyr Ala Asp Ser Val Lys
    50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg Asp Tyr Tyr Tyr Tyr Ala Ser Gly Ser Tyr Tyr Lys Ala Phe Asp
            100                 105                 110

Ile Trp Gly Gln Gly Thr Met Val Thr Val Ser Ser
        115                 120

<210> SEQ ID NO 40
<211> LENGTH: 108
<212> TYPE: PRT
<213> ORGANISM: Artificial Sequence
```

<220> FEATURE:
<223> OTHER INFORMATION: Synthetic sequence

<400> SEQUENCE: 40

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Arg
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Pro Leu
                85                  90                  95

Thr Phe Gly Gln Gly Thr Lys Leu Glu Ile Lys Arg
            100                 105

<210> SEQ ID NO 41
<211> LENGTH: 350
<212> TYPE: PRT
<213> ORGANISM: Homo sapiens

<400> SEQUENCE: 41

Met Asp Ser Phe Asn Tyr Thr Thr Pro Asp Tyr Gly His Tyr Asp Asp
1               5                   10                  15

Lys Asp Thr Leu Asp Leu Asn Thr Pro Val Asp Lys Thr Ser Asn Thr
            20                  25                  30

Leu Arg Val Pro Asp Ile Leu Ala Leu Val Ile Phe Ala Val Val Phe
        35                  40                  45

Leu Val Gly Val Leu Gly Asn Ala Leu Val Val Trp Val Thr Ala Phe
    50                  55                  60

Glu Ala Lys Arg Thr Ile Asn Ala Ile Trp Phe Leu Asn Leu Ala Val
65                  70                  75                  80

Ala Asp Phe Leu Ser Cys Leu Ala Leu Pro Ile Leu Phe Thr Ser Ile
                85                  90                  95

Val Gln His His His Trp Pro Phe Gly Gly Ala Ala Cys Ser Ile Leu
            100                 105                 110

Pro Ser Leu Ile Leu Leu Asn Met Tyr Ala Ser Ile Leu Leu Leu Ala
        115                 120                 125

Thr Ile Ser Ala Asp Arg Phe Leu Leu Val Phe Lys Pro Ile Trp Cys
    130                 135                 140

Gln Asn Phe Arg Gly Ala Gly Leu Ala Trp Ile Ala Cys Ala Val Ala
145                 150                 155                 160

Trp Gly Leu Ala Leu Leu Leu Thr Ile Pro Ser Phe Leu Tyr Arg Val
                165                 170                 175

Val Arg Glu Glu Tyr Phe Pro Pro Lys Val Leu Cys Gly Val Asp Tyr
            180                 185                 190

Ser His Asp Lys Arg Arg Glu Arg Ala Val Ala Ile Val Arg Leu Val
        195                 200                 205

Leu Gly Phe Leu Trp Pro Leu Leu Thr Leu Thr Ile Cys Tyr Thr Phe
    210                 215                 220

Ile Leu Leu Arg Thr Trp Ser Arg Arg Ala Thr Arg Ser Thr Lys Thr
225                 230                 235                 240

-continued

```
Leu Lys Val Val Val Ala Val Val Ala Ser Phe Phe Ile Phe Trp Leu
            245                 250                 255

Pro Tyr Gln Val Thr Gly Ile Met Met Ser Phe Leu Glu Pro Ser Ser
            260                 265                 270

Pro Thr Phe Leu Leu Leu Lys Lys Leu Asp Ser Leu Cys Val Ser Phe
            275                 280                 285

Ala Tyr Ile Asn Cys Cys Ile Asn Pro Ile Ile Tyr Val Val Ala Gly
            290                 295                 300

Gln Gly Phe Gln Gly Arg Leu Arg Lys Ser Leu Pro Ser Leu Leu Arg
305                 310                 315                 320

Asn Val Leu Thr Glu Glu Ser Val Val Arg Glu Ser Lys Ser Phe Thr
            325                 330                 335

Arg Ser Thr Val Asp Thr Met Ala Gln Lys Thr Gln Ala Val
            340                 345                 350
```